(12) United States Patent
Fruland et al.

(10) Patent No.: US 9,211,155 B2
(45) Date of Patent: Dec. 15, 2015

(54) NON-THERMAL ABLATION SYSTEM FOR TREATING BPH AND OTHER GROWTHS

(75) Inventors: Benjamin R. Fruland, Plymouth, MN (US); Kai Kroll, Plymouth, MN (US); Tom A. Nelson, Elk River, MN (US); Stephen K. Sundquist, Minnetonka, MN (US); Michael C. Holtz, Elk River, MN (US)

(73) Assignee: Prostacare Pty Ltd. (AU)

( * ) Notice: Subject to any disclaimer, the term of this patent is extended or adjusted under 35 U.S.C. 154(b) by 639 days.

(21) Appl. No.: 12/544,112

(22) Filed: Aug. 19, 2009

(65) Prior Publication Data

US 2010/0049031 A1    Feb. 25, 2010

Related U.S. Application Data

(60) Provisional application No. 61/090,519, filed on Aug. 20, 2008, provisional application No. 61/090,594, filed on Aug. 20, 2008, provisional application No. 61/090,589, filed on Aug. 20, 2008, provisional application No. 61/090,600, filed on Aug. 20, 2008.

(51) Int. Cl.
*A61B 18/18* (2006.01)
*A61B 18/14* (2006.01)
(Continued)

(52) U.S. Cl.
CPC ............. *A61B 18/1492* (2013.01); *A61B 5/055* (2013.01); *A61B 8/08* (2013.01); *A61B 19/56* (2013.01);
(Continued)

(58) Field of Classification Search
CPC .......... A61B 2017/00274; A61B 2018/00547; A61B 10/0241; A61B 2018/1266; A61B 2018/1475; A61B 2018/143

USPC ...................................................... 606/46, 48
See application file for complete search history.

(56) References Cited

U.S. PATENT DOCUMENTS 3,698,394 A   10/1972   Piper et al.
3,933,616 A   1/1976    Beer
(Continued)

FOREIGN PATENT DOCUMENTS

EP   1080731 A2   3/2001
EP   2 326 273    6/2011
(Continued)

OTHER PUBLICATIONS

Taylor, T.V., et al. "Ablation of neoplasia by direct current." British Journal of Cancer. 70 (1994): 342-345. Print.*
(Continued)

*Primary Examiner* — Jaymi Della
(74) *Attorney, Agent, or Firm* — Patterson Thuente Pedersen, P.A.

(57) ABSTRACT

Systems and methods for non-thermal ablation of tissue are provided. A non-implantable minimally invasive system for treatment of tissue in a body via direct current ablation is provided including a catheter, a plurality of electrodes for deployment through the catheter, a power source for applying power to the electrodes, and a fixation element for maintaining the catheter in a treatment position during treatment of the tissue. A minimally invasive method for treating tissue in a body via direct current ablation is provided including inserting a catheter into the body such that a portion of the catheter remains outside of the body, deploying a fixation element to fix the catheter in a treatment position, deploying a plurality of electrodes through the catheter, applying power to the plurality of electrodes, using the electrodes to apply a current to the tissue, and removing the catheter from the body.

29 Claims, 45 Drawing Sheets

(51) Int. Cl.
  *A61B 5/055* (2006.01)
  *A61B 8/08* (2006.01)
  *A61B 19/00* (2006.01)
  *A61B 18/00* (2006.01)
  *A61B 18/12* (2006.01)

(52) U.S. Cl.
  CPC ............. *A61B 2018/00285* (2013.01); *A61B 2018/00547* (2013.01); *A61B 2018/00577* (2013.01); *A61B 2018/1266* (2013.01); *A61B 2018/143* (2013.01); *A61B 2018/1475* (2013.01); *A61B 2019/5276* (2013.01)

(56) References Cited

U.S. PATENT DOCUMENTS

| | | | |
|---|---|---|---|
| 4,003,379 A | 1/1977 | Ellinwood, Jr. | |
| 4,026,304 A | 5/1977 | Levy | |
| 4,289,135 A | 9/1981 | Nordenstrom et al. | |
| 4,572,214 A | 2/1986 | Nordenstrom et al. | |
| 4,639,244 A | 1/1987 | Rizk et al. | |
| 4,679,561 A | 7/1987 | Doss | |
| 4,682,596 A | 7/1987 | Bales et al. | |
| 4,721,123 A | 1/1988 | Cosentino et al. | |
| 4,919,138 A | 4/1990 | Nordenstrom | |
| 4,974,595 A | 12/1990 | Nordenstrom | |
| 5,026,371 A | 6/1991 | Rydell et al. | |
| 5,058,605 A | 10/1991 | Slovak | |
| 5,098,843 A | 3/1992 | Calvin | |
| 5,281,218 A | 1/1994 | Imran | |
| 5,314,451 A | 5/1994 | Mulier | |
| 5,314,457 A | 5/1994 | Jeutter et al. | |
| 5,370,675 A | 12/1994 | Edwards et al. | |
| 5,431,625 A * | 7/1995 | Fabian et al. | 604/20 |
| 5,458,627 A | 10/1995 | Baranowski | |
| 5,482,054 A | 1/1996 | Slater et al. | |
| 5,501,662 A | 3/1996 | Hofmann | |
| 5,507,724 A | 4/1996 | Hofmann et al. | |
| 5,529,574 A * | 6/1996 | Frackelton | 604/22 |
| 5,536,267 A | 7/1996 | Edwards et al. | |
| 5,584,872 A | 12/1996 | LaFontaine et al. | |
| 5,611,350 A | 3/1997 | John | |
| 5,630,426 A | 5/1997 | Eggers et al. | |
| 5,674,267 A | 10/1997 | Mir et al. | |
| 5,701,895 A | 12/1997 | Prutchi et al. | |
| 5,807,306 A | 9/1998 | Shapland et al. | |
| 5,810,764 A | 9/1998 | Eggers et al. | |
| 5,820,548 A | 10/1998 | Sieben et al. | |
| 5,868,741 A | 2/1999 | Chia et al. | |
| 5,869,326 A | 2/1999 | Hofmann | |
| 5,919,187 A | 7/1999 | Guglielmi et al. | |
| 5,983,131 A | 11/1999 | Weaver et al. | |
| 5,985,305 A | 11/1999 | Peery et al. | |
| 5,993,434 A | 11/1999 | Dev et al. | |
| 6,009,345 A | 12/1999 | Hofmann | |
| 6,016,452 A | 1/2000 | Kasevich | |
| 6,021,347 A | 2/2000 | Herbst et al. | |
| 6,023,638 A | 2/2000 | Swanson | |
| 6,049,733 A | 4/2000 | Phipps et al. | |
| 6,051,017 A | 4/2000 | Loeb et al. | |
| 6,162,219 A | 12/2000 | Nilsson et al. | |
| 6,165,206 A | 12/2000 | Tu | |
| 6,169,924 B1 | 1/2001 | Meloy et al. | |
| 6,171,787 B1 | 1/2001 | Wiley | |
| 6,174,309 B1 | 1/2001 | Wrublewski et al. | |
| 6,238,393 B1 | 5/2001 | Mulier et al. | |
| 6,245,068 B1 | 6/2001 | Olson et al. | |
| 6,269,270 B1 | 7/2001 | Boveja | |
| 6,273,886 B1 | 8/2001 | Edwards | |
| 6,278,895 B1 | 8/2001 | Bernard | |
| 6,366,808 B1 | 4/2002 | Schroeppel et al. | |
| 6,387,075 B1 | 5/2002 | Stivland et al. | |
| 6,391,026 B1 | 5/2002 | Hung et al. | |
| 6,402,745 B1 | 6/2002 | Wilk | |
| 6,419,673 B1 | 7/2002 | Edwards et al. | |
| 6,464,699 B1 | 10/2002 | Swanson | |
| 6,591,133 B1 | 7/2003 | Joshi | |
| 6,595,989 B1 | 7/2003 | Schaer | |
| 6,599,274 B1 | 7/2003 | Kucharczyk et al. | |
| 6,600,953 B2 | 7/2003 | Flesler et al. | |
| 6,607,528 B1 | 8/2003 | Quick et al. | |
| 6,626,899 B2 | 9/2003 | Houser et al. | |
| 6,638,273 B1 | 10/2003 | Farley et al. | |
| 6,638,275 B1 * | 10/2003 | McGaffigan et al. | 606/41 |
| 6,708,066 B2 | 3/2004 | Herbst et al. | |
| 6,713,291 B2 | 3/2004 | King et al. | |
| 6,733,485 B1 | 5/2004 | Whitehurst et al. | |
| 6,738,663 B2 | 5/2004 | Schroeppel et al. | |
| 6,901,296 B1 | 5/2005 | Whitehurst et al. | |
| 6,952,615 B2 | 10/2005 | Satake | |
| 7,079,890 B2 | 7/2006 | Ahn et al. | |
| 7,412,285 B2 | 8/2008 | Schroeppel et al. | |
| 7,556,624 B2 | 7/2009 | Laufer et al. | |
| 7,720,549 B2 | 5/2010 | Schroeppel et al. | |
| 7,742,811 B2 | 6/2010 | Schroeppel et al. | |
| 8,014,854 B2 | 9/2011 | Schroeppel et al. | |
| 8,024,048 B2 | 9/2011 | Schroeppel et al. | |
| 2001/0001314 A1 | 5/2001 | Davison et al. | |
| 2001/0021868 A1 | 9/2001 | Herbst et al. | |
| 2001/0034518 A1 | 10/2001 | Edwards et al. | |
| 2002/0026188 A1 | 2/2002 | Balbierz et al. | |
| 2002/0077676 A1 | 6/2002 | Schroeppel et al. | |
| 2002/0115957 A1 | 8/2002 | Sun et al. | |
| 2002/0183735 A1 | 12/2002 | Edwards et al. | |
| 2003/0130711 A1 | 7/2003 | Pearson et al. | |
| 2003/0191504 A1 | 10/2003 | Meadows et al. | |
| 2003/0212394 A1 * | 11/2003 | Pearson et al. | 606/41 |
| 2004/0010290 A1 | 1/2004 | Schroeppel et al. | |
| 2004/0030334 A1 | 2/2004 | Quick et al. | |
| 2004/0059326 A1 | 3/2004 | Flores | |
| 2004/0172089 A1 | 9/2004 | Whitehurst et al. | |
| 2004/0254618 A1 | 12/2004 | Schroeppel et al. | |
| 2005/0004507 A1 | 1/2005 | Schroeppel et al. | |
| 2005/0010203 A1 * | 1/2005 | Edwards et al. | 606/32 |
| 2005/0054994 A1 | 3/2005 | Cioanta et al. | |
| 2005/0159742 A1 | 7/2005 | Lesh | |
| 2005/0182449 A1 | 8/2005 | Auge et al. | |
| 2005/0222623 A1 | 10/2005 | Kroll et al. | |
| 2005/0222646 A1 * | 10/2005 | Kroll et al. | 607/72 |
| 2005/0228373 A1 * | 10/2005 | Kelly et al. | 606/41 |
| 2005/0283125 A1 | 12/2005 | Barkhahn et al. | |
| 2005/0288730 A1 | 12/2005 | Deem et al. | |
| 2006/0025756 A1 | 2/2006 | Francischelli et al. | |
| 2006/0095032 A1 | 5/2006 | Jackson et al. | |
| 2006/0235286 A1 * | 10/2006 | Stone et al. | 600/381 |
| 2006/0259027 A1 | 11/2006 | Kwan et al. | |
| 2007/0073391 A1 | 3/2007 | Bourang et al. | |
| 2007/0191925 A1 | 8/2007 | Dorn | |
| 2007/0255207 A1 | 11/2007 | Hangai et al. | |
| 2008/0021275 A1 | 1/2008 | Tearney et al. | |
| 2008/0021445 A1 | 1/2008 | Elmouelhi et al. | |
| 2008/0027379 A1 | 1/2008 | Wilkins | |
| 2008/0071262 A1 | 3/2008 | Azure | |
| 2009/0024075 A1 | 1/2009 | Schroeppel et al. | |
| 2010/0049188 A1 | 2/2010 | Nelson et al. | |
| 2010/0049192 A1 | 2/2010 | Holtz et al. | |
| 2011/0106072 A1 | 5/2011 | Sundquist et al. | |
| 2012/0203307 A1 | 8/2012 | Schroeppel et al. | |

FOREIGN PATENT DOCUMENTS

| | | |
|---|---|---|
| EP | 2 326 274 | 6/2011 |
| WO | WO 98/47562 A1 | 10/1998 |
| WO | WO 01/52931 A1 | 7/2001 |
| WO | WO 01/62336 A1 | 8/2001 |
| WO | WO 02/098501 A2 | 12/2002 |
| WO | WO 2006/042117 A2 | 4/2006 |
| WO | WO 2006042117 A2 * | 4/2006 |
| WO | WO 2008/083407 A1 | 7/2008 |

(56) References Cited

FOREIGN PATENT DOCUMENTS

WO    WO 2010/022275 A1    2/2010
WO    WO 2010/022278 A1    2/2010

OTHER PUBLICATIONS

Reis A, Henninger T. Zerstorung maligner Wachstumsenergie durch anodische Oxydation. Kim Wochenschrift 1951;_: 39.
Nordenstrom B. Preliminary clinical trials of electrophoretic ionization in the treatment of malignant tumors. IRCS Med Sc 1978; 6: 537.
Schauble MK, Mutaz HB, Gallick HD. Inbitition of experimental tumor growth In hamsters by small direct currents. Arch Pathol Lab Med 1977; 101: 294.
Srinivasan S, Gahen Jr. GL, Stoner GE. Electrochemistry in the biomedical sciences. In: Bloom H, Gutmann F (eds): Electrochemistry the last thirty and the next thirty years. New York: Plenum Press, 1977.
Nordenstrom BEW. Biologically closed electric circuits: clinical, experimental and theoretical evidence for an additional circulatory system. Stockholm: Nordic Medical Publications, 1983.
Nordenstrom B. Biologically closed electric circuits: activation of vascular interstitial closed electric circuits for treatment of inoperable cancer. Journal of Bioelectricity 1984; 3(162): 137-153.
Lao, Y., Ge, T., Zheng, X., Zhang, J. Hua, Y., Mao, S., Feng, X. Electrochemical therapy for intermediate and advanced liver cancer: a report of 50 cases. Eur J Surg 1994; Suppl 574: 51-53.
Mir Lm, Orlowski S, Belehradek Jr J, Paoletti C. Electrochemotherapy potentiation of antitumour effect of bleomycin by local electric pulses. Eur J. Cancer 1991; 27:68-72.
Wolf B, Kraus M, and Sieben U, Potential of microsensor-based feedback bioactuators for biophysical cancer treatment, Biosensors and Bioelectronics, vol. 12, No. 4, pp. 301-309, 1997.
Kirsch DL, Lerner FN. Electromedicine: the other side of physiology. In: Innovations in pain management: a practical guide for clinicians. Winter Park, FL: GR Press, 1995.
Li K, Xin Y, Gu Y, Xu B, Fan D. Ni B. Effects of direct current on dog liver: possible mechanisms for tumor electrochemical treatment . Bioelectromagnetics 1997; 18: 2-7.
Berendson J. Simonsson D. Electrochemical aspects of treatment of tissue with direct current. Eur J Surg 1994: Suppl 574: 111-115.
Song Y, Li C, Li Y, Song Q. Chang B, Song L. Liu C. Wang T. Electrochemical therapy in the treatment of malignant tumors on the body surface. Eur J Surg 1994; Suppl 574: 41-43.
Matsushima Y, Takahashi E, Hagiwara K, Konaka C, Miura H, Kato H, Koshiishi Y. Clinical and experimental studies of anti-tumoural effects of electrochemical therapy (ECT) alone or in combination with chemotherapy. Eur J Surg 1994; Suppl 574: 59-67.
Xin Y, Xue F, Ge B, Zhao F, Shi B, Zhang W. Electrochemical treatment of lung cancer. Bioelectromagnetics 1997; 18: 8-13.
Nordenstrom BEW. Electrochemical treatment of cancer. I: variable response to anodic and cathodic fields. Am J Clin Oncol (CCT) 1989; 12(6): 530-536.
Nordenstrom BEW. Survey of mechanisms in electrochemical treatment (ECT) of cancer. Eur J Surg 1994: Suppl 574: 93-109.
Chen B, Xie Z, Zhu F. Experimental study on electrochemical treatment of cancer in mice. Eur J Surg 1994; Suppl 574: 75-77.
Chou C, McDougall JA, Ahn C, Vora N. Electrochemical treatment of mouse and rat fibrosarcomas with direct current. Bioelectromagnetics 1997; 18: 14-24.
Nordenstrom BEW, Eksborg, S., Beving, H. Electrochemical treatment of cancer. II: effect of electrophoretic influence on adriamycin. Am J Clin Oncol (CCT)1990; 13(1): 75-88.
Xin, Y. Organisation and spread of electrochemical therapy (ECT) in China. Eur J Surg 1994; Suppl 577: 25-30.
Quan, K. Analysis of the clinical effectiveness of 144 cases of soft tissue and superficial malignant tumors treated with electrochemical therapy. Eur J Surg 1994; Suppl 574: 37-40.
Wang, H. Electrochemical therapy of 74 cases of liver cancer. Eur J Surg 1994; Suppl 574: 55-57.
Song, L., Liu, C., Zhang, B., Wang, T., Song, Y., Li, Y. Electrochemical therapy (ECT) for thyroid adenoma during acupuncture anaesthesia: analysis of 46 patients. Eur J Surg 1994; Suppl 574: 79-81.
Yokoyama, M., Itaoka, T., Nakajima, H., Ikeda, T., Ishikura, T., Nitta, S. [The use of direct current in the local destruction of cancer tissues]. Gan to Kagaku Ryoho Apr. 1989; 16(4 Pt 2-2): 1412-1417.
Okino, M. and Mohri, H. Effects of high voltage electrical impulse and an anti-cancer drug on growing tumors. Japanese Journal of Cancer Research, vol. 78, pp. 1319-1321, 1987.
Orlowski, S., Belehradek, J.J., Paoletti,C. and Mir, L.M. "Transient electropermeabilization of cells in culture increase of the cytotoxicity of anti-cancer drugs", Biochem, vol. 37, No. 24, pp. 4727-4733, 1988.
Belahradek, J.J., Orlowski, S., Raimiriz, L.H., Pron, G., Poddevin, B. and Mir, L.M., "Electropermeabilization of cells and tissues assessed by the qualitative and quantitative electroloading of bleomycin", Biochem. Biophys. Acta, vol. 1190, pp. 155-163, 1994.
Hofmann, G.A., Dev. S.B., Dimmer, S. and Nanda, G.S., "Electroporation Therapy: A new approach to the treatment of head and neck cancer, IEEE Transactions on Biomedical Engineering", vol. 46, No. 6, pp. 752-759, 1999.
Schecter, DC. "Containment of Tumors Through Electricity." PACE 1979. vol. 2, pp. 100-114.
Sersa, et al. Improvement of Combined modality therapy with cisplatin and radiation using electroporation of tumors. Int J. Radiation Oncology Biol. Phys. vol. 46, No. 4:1037-1041. (2000).
Hofmann, Dev, Nanda, and Rabussay. electroporation therapy of solid tumors. Critical Reviews in therapeutic Drug Carrier Systems 16(6):523-569 (1999).
Samuelsson, Harnek, Ewers, Jonsson. Electrochemical and megavolt treatment of rat tumors. Eur J Surg Suppl 574:69-70. (1994).
Habal and Schauble. An implantable DC power unit for control of experimental tumor growth in hamsters. Medical Instrumentation 7 No. 5: 305-306. (1973).
Semrov and Miklacic. Calculation of the electrical parameters inn electrochemistry of solid tumors in mice. Comp Biol Med 28:439-448. (2000).
Turler, Schaefer, et al. Local treatment of hepatic metastases with low level direct electrical current: experimental results. Scand J Gastroenterol. 3:322-328. (2000).
http://www.genetronics, retrieved Jul. 29, 2003.
Electro-Cancer Treatment, http://www.st-georg.com/ect.html, retrieved Oct. 25, 1999.
M. Belehradek, C. Domenge, B. Luboinski, S. Orlowski, J. Belehradek, Jr., L.M. Mir. Abstract of Electrochemotherapy, A new antitumor treatment. First clinical phase I-II trial. Cancer Dec. 15, 1993; 72(12):3694-700.
K. Brandisky, I. Daskalov. Abstract of Electrical Field and Current Distributions in Electrochemotherapy, Bioelectrochemistry and Bioenergetics Feb. 1999; 48(1):201-8.
M. Cemazar, G. Sersa and D. Miklavcic. Electrochemotherapy with Cisplatin in the Treatment of Tumor Cells Resistant to Cisplatin, Anticancer Research 18: 44563-4466 (1998).
S.L. David, D.R. Absolom, C.R. Smith, J. Gams, and M.A. Herbert. Effect of Low Level Direct Current on In Vivo Tumor Growth in Hamsters, Cancer Research 45, 5625-5631, Nov. 1985.
D. Liu, Y.L. Xin, B. Ge, F. Zhao, H.C. Zhso. Experimental Studies on Electrolytic Dosage of ECT for Dog's Oesophageal Injury and Clinical Effects of ECT for Oesopohageal Anastomotic Opening Stenosis and Oesophageal Carcinoma, European Journal of Surgery 1994; Suppl 574: 71-72.
R.A. Gatenby. Abstract of Mathematical Models of Tumour Invasion Mediated by Transformation-Induced Alteration of Microenvironment pH, Symposium 240: The Tumour Microenvironment: Causes and Consequences of Hypoxia and Acidity, p. 2-3, held at the Novartis Foundation, London, 240 Oct. 10-12, 2000.
L.F. Glass, N.A. Fenske, M. Jaroszeski, R. Perrott, D.T. Harvey, D.S. Reintgen, R. Heller. Abstract of Bleomycin-Mediated Electrochemotherapy of Basal Cell Carcinoma, Journal of the American Academy of Dermatology Jan. 1996; 34(1):82-6.

(56) References Cited

OTHER PUBLICATIONS

H. Gong, G. Liu. Effect of Electrochemical Therapy on Immune Functions of Normal and Tumour-Bearing Mice, European Journal of Surgery, Suppl 1994; (574): 73-74.
S.A. Grossman, P.S. Staats, Abstract of Current Management of Pain in Patients with Cancer. Oncology (Huntingt) Mar. 1994; 8(3):93-107.
M.B. Habal. Abstract of Effect of Applied DC Currents on Experimental Tumor Growth in Rats, Journal of Biomedical Materials Research, vol. 14, 789-801 (1980).
M.A. Hamza, P.F. White, H.E. Ahmed, E.A. Ghoname. Abstract of Effect of the Frequency of Transcutaneous Electrical Nerve Stimulation on the Postoperative Opioid Analgesic Requirement and Recovery Profile, Anesthesiology Nov. 1999;91(5):1232-8.
C. Hauton, M. Charbonnier, L. Cara and J.P. Salles, A New Type of Liposome for Electrochemical Treatment of Cancer: The Lipogelosomes, European Journal of Surgery 1994; Suppl 574: 117-119.
C.E. Humphrey, E.H. Seal. Biophysical Approach toward Tumor Regression in Mice, Science, vol. 130, 1959.
M. Kraus and B. Wolf. Implications of Acidic Tumor Microenvironment for Neoplastic Growth and Cancer Treatment: A Computer Analysis, Tumor Biology 1996; 17: 133-154.
M. Kraus and B. Wolf. Physicochemical Microenvironment as Key Regulator for Tumor Microevolution, Invasion, and Immune Response: Targets for Endocytotechnological Approaches in Cancer Treatment, Endocytobiosis & Cell Research, 12, 133-156 (1998).
Miklavcic, D. An, J. Belehradek, Jr., L.M. Mir. Abstract of Host's Immune Response in Electrotherapy of Murine Tumors by Direct Current, European Cytokine Network Sep. 1997;8(3):275-9.
D.M. Morris, M.D., A.A. Marino, Ph. D., and E. Gonzalez, M.D. Electrochemical Modification of Tumor Growth in Mice, Journal of Surgical Research 53, 306-309 (1992).
E. Nilsson. Modelling of the Electrochemical Treatment of Tumours. Dissertation, Department of Chemical Engineering and Technology, Applied Electrochemistry, Royal Institute of Technology, Stockholm 2000.
T. Nishi, S.B. Dev., K. Yoshizato, J. Kuratsu, Y. Ushio. Abstract of Treatment of Cancer Using Pulsed Electric Field in Combination With Chemotherapeutic Agents or Genes, Human Cell Mar. 1997;10(1):81-6.
G.D. O'Clock, Ph. D. (E.E.), P.E. The Effects of In Vitro Electrical Stimulation on Eukaryotic Cells: Suppression of Malignant Cell Proliferation, Journal of Orthomolecular Medicine, vol. 12, No. 3, 1997.
W.R. Panje, M.P. Hier, G.R. Garman, E. Harrell, A. Goldman, I. Bloch. Abstract of Electroporation Therapy of Head and Neck Cancer, Annals of Otology, Rhinology and Laryngology Sep. 1998; 107(9 Pt 1): 779-85.
A. Plesnicar, G. Sersa, L. Vodovnik, J. Jancar, L. Zaletel-Kragelj and S. Plesnicar. Electric Treatment of Human Melanoma Skin Lesions with Low Level Direct Electric Current: An Assessment of Clinical Experience Following a Preliminary Study in Five Patients, European Journal of Surgery 1994; Suppl 574:45-49.
N. Raghunand. Abstract of pH and Chemotherapy, Symposium 240: The Tumour Microenvironment: Causes and Consequences of Hypoxia and Acidity, p. 5-6, held at the Novartis Foundation, London, 240 Oct. 10-12, 2000.
L.H. Ramirez, S. Orlowski, D. An, G. Bindoula, R. Dzodic, P. Ardouin, C. Bognel, J. Belehradek Jr., J-N. Munck, and L.M. Mir. Electrochemotherapy on Liver Tumours in Rabbits, British Journal of Cancer (1998) 77(12). 2104-2111.
M.K. Schauble, M.B. Habal. Electropotentials of Tumor Tissues. Journal of Surgical Research 9: 9, 1969.
S. Seguchi, S. Kawauchi, Y. Morimoto, T. Arai, H. Asanuma, M. Hayakawa, M. Kikuchi. Abstract of Critical Parameters in the Cytotoxicity of Photodynamic Therapy Using a Pulsed Laser. Lasers Med Sci 2002, 17(4):265-71.

G. Sersa, M. Cemazar, D. Miklavcic and D. J. Chaplin, Tumor Blood Flow Modifying Effect of Electrochemotherapy with Bleomycin, Anticancer Research 19: 4017-4022 (1999).
B.N. Singh and C. Dwivedi. Antitumor Drug Delivery by Tissue Electroporation, Anti-Cancer Drugs 1999, 10, pp. 139-146.
T.V. Taylor, P. Engler, B.R. Pullan and S. Holt. Ablation of Neoplasia by Direct Current, British Journal of Cancer (1994), 70, 342-345.
A.L. Vandenbogaerde, E.M. Delaey, A.M. Vantieghem, B.E. Himpens, W.J. Merlevede, P.A. de Witte, Abstract of Cytotoxicity and Antiproliferative Effect of Hypericin and Derivatives After Photosensitization. Photochem Photobiol Jan. 1998;67(1):119-25.
P. Vaupel, D.K. Kelleher, M. Hockel. Abstract of Oxygen Status of Malignant tumors: Pathogenesis of Hypoxia and Significance for Tumor Therapy. Semin Oncol Apr. 2001; 28(2 Suppl 8):29-35.
L. Vodovnik, D. Miklavcic, G. Sersa. Modified Cell Proliferation Due to Electrical Currents, Medical and Biological Engineering and Computing, 1992, 30, CE21-CE28.
H. von Euler, Electrochemical Treatment of Tumours, Doctoral Thesis, Swedish University of Agricultural Sciences, Uppsala 2002.
J.C. Weaver. Electroporation: A General Phenomenom for Manipulating Cells and Tissues. J Cell Biochem 1993; 51 No. 4: 426-435.
M. Wojcicki, R. Kostyrka, B. Kaczmarek, J. Kordowski, M. Romanowski, M. Kaminski, J. Klonek, S. Zielinski. Abstract of Electrochemical Therapy in Palliative Treatment of Malignant Dysphagia: A Pilot Study, Hepatogastroenterology Jan.-Feb. 1999;46(25):278-84.
B. Wolf, M. Brischwein, W. Baumann, R. Ehret, T. Henning, M. Lehmann, A. Schwinde. Microsensor-Aided Measurements of Cellular Signalling and Metabolism on Tumor Cells, Tumor Biology 1998; 19:374-383.
Y.L. Xin, F.Z. Xue, F.G. Zhao. Effectiveness of Electrochemical Therapy in the Treatment of Lung Cancers of Middle and Late Stage, Chinese Medical Journal 1997 110(5): 379-383.
Y. Yen, J.R. Li, B.S. Zhou, F. Rojas, J. Yu and C.K. Chou. Electrochemical Treatment of Human KB Cells In Vitro, Bioelectromagnetics 20:34-41 (1999).
Y.L. Xin, D. Liu. Electrostatic Therapy (EST) of Lung Cancer and Pulmonary Metastasis: Report of 15 Cases. European Journal of Surgery 1994; Suppl 574: 91-92.
X.Z. Lin, C.M. Jen, C.K. Choud, D.S. Chou, M.J. Sung, T.C. Chou. Saturated Saline Enhances the Effect of Electrochemical Therapy. Digestive Diseases and Sciences 2000: 45(3): 509-514.
Damascelli B, Patelli G, Frigerio LF, Lanocita R, Di Tolla GD, Marchiano A., Spreafico C, Garbagnati F, Bonalumi MG, Monfardini L Ticha V, Prino A. First clinical experience with a high-capacity implantable infusion pump for continuous intravenous chemotherapy. Cardiovasc Intervent Radiol 1999; 22: 37-43.
Ranade VV. Drug delivery systems. 4. Implants in drug delivery. J Clin Pharmacol 1990; 30 No. 10: 871-889.
Buchwald H, Rohde TD. Implantable pumps. Recent progress and anticipated future advances. ASAIO J 1992; 38 No. 4: 772-778.
Wigness BD, Dorman FD, Robinson Jr HJ, Arendt EA, Oegema Jr TR, Rohde TD, Buchwald H. Catheter with an anchoring tip for chronic joint capsule perfusion. ASAIO Trans. 1991; 37 No. 3: M290-292.
Heruth KT, Medtronic SynchroMed drug administration system. Ann NY Acad Sci 1988; 531: 72-75.
Vogelzang NJ, Ruane M, DeMeester TR. Phase I trial of an implanted battery-powered, programmable drug delivery system for continuous doxorubicin administration. J Clin Oncol 1985; 3 No. 3: 407-414.
Application and File history for U.S. Appl. No. 09/524,405, filed Mar. 13, 2000, now U.S. Pat. No. 6,366,808, issued Apr. 2, 2002. Inventors: Schroeppel et al.
Application and File history for U.S. Appl. No. 09/974,474, filed Dec. 14, 2001, now U.S. Pat. No. 6,738,663, issued May 18, 2004. Inventors: Schroeppel et al.
Application and File history for U.S. Appl. No. 10/434,400, filed May 7, 2003, now U.S. Pat. No. 7,412,285, issued Aug. 12, 2008. Inventors: Schroeppel et al.
Application and File history for U.S. Appl. No. 10/792,256, filed Mar. 2, 2004, now U.S. Pat. No. 7,742,811, issued Jun. 22, 2010. Inventors: Schroeppel et al.

(56) References Cited

OTHER PUBLICATIONS

Application and File history for U.S. Appl. No. 12/173,639, filed Jul. 15, 2008, now U.S. Pat. No. 8,014,854, issued Sep. 6, 2011. Inventors: Schroeppel et al.

Application and File history for U.S. Appl. No. 13/226,319, filed Sep. 6, 2011. Inventors: Schroeppel et al.

Application and File history for U.S. Appl. No. 10/819,641, filed Sep. 6, 2011, now U.S. Pat. No. 7,720,549, issued May 18, 2010. Inventors: Schroeppel et al.

Application and File history for U.S. Appl. No. 10/881,375, filed Jun. 29, 2006. Inventors: Schroeppel et al.

Application and File history for U.S. Appl. No. 10/841,205, filed May 7, 2004, now U.S. Pat. No. 8,024,048, issued Sep. 20, 2011. Inventors: Schroeppel et al.

Application and File history for U.S. Appl. No. 12/544,119, filed Aug. 19, 2009. Inventors: Sundquist et al.

Application and File history for U.S. Appl. No. 12/544,127, filed Aug. 19, 2009. Inventors: Holtz et al.

Application and File history for U.S. Appl. No. 12/544,134, filed Aug. 19, 2009. Inventors: Nelson et al.

EP Application No. 037997616, EP Search Report, dated Feb. 2, 2010.

EP Application No. 05733003.7, Search Report, dated Apr. 11, 2008.

EP 05733003.7, Office Action, dated Aug. 13, 2008.

EP Application No. 05733003.7, Examination Report, dated Apr. 21, 2009.

PCT/US2003/14104, International Search Report, Nov. 18, 2004.

PCT/US2005/011430, PCT International Written Opinion, dated Jan. 13, 2006.

PCT/US2009/54528, PCT International Search Report, dated Oct. 22, 2009.

PCT/US2009/054523, PCT International Preliminary Report on Patentability and Written Opinion, dated Feb. 22, 2011.

EP09808837.0, EP Search Opinion, dated Apr. 11, 2012.

EP09808839.6, EP Search Opinion, dated Jul. 27, 2012.

\* cited by examiner

NON-THERMAL ABLATION SYSTEM FOR TREATING BPH AND OTHER GROWTHS

CROSS-REFERENCE TO RELATED APPLICATIONS

This application claims priority to U.S. Provisional Patent Application Nos. 61/090,519, filed Aug. 20, 2008; 61/090,594, filed Aug. 20, 2008; 61/090,600, filed Aug. 20, 2008; and 61/090,589, filed Aug. 20, 2008, filed Aug. 20, 2008; and is related to the following U.S. Patent Applications:

U.S. patent application Ser. No. 12/544,119, entitled "Low-Corrosion Electrode for Treating Tissue", filed on Aug. 19, 2009;

U.S. patent application Ser. No. 12/544,127, entitled "Catheter for Treating Tissue with Non-Thermal Ablation", filed on Aug. 19, 2009; and U.S. patent application Ser. No. 12/544,134, entitled "Non-Thermal Ablation System Treating Tissue", filed on Aug. 19, 2009.

The contents of each of the above listed applications are hereby incorporated by reference herein in their entireties.

FIELD OF THE INVENTION

The present invention relates generally to systems and methods for treating tissue and, more specifically, to non-thermal ablation systems and methods for treating tissue.

BACKGROUND

Enlargement of the prostate gland (known as benign prostatic hyperplasia or hypertrophy—"BPH") is a common ailment in older men. BPH affects 40% of men in their 50s and 90% of men in their 80s. The enlargement of the prostate is a form of benign tumor or adenoma. FIG. 1 illustrates a simplified view of the anatomy and location of the prostate 3, 4. The urethra 1 passes upwards through the external urethral sphincter 2, through the prostate 3, 4 (surrounding the urethra), and into the bladder 5. The prostate 3, 4 comprises three lobes: two major lobes 3, 4 and a median lobe. The median lobe is located generally behind the major lobes 3, 4.

As the prostate becomes enlarged, it may compress the urethra and cause one or more of the following symptoms to occur: more frequent urination, weak urine stream, inability to delay urination, difficulty starting and stopping urination, incomplete emptying of the bladder, loss of bladder control, and painful or bloody urination.

If symptoms are mild and do not affect quality of life, treatment may not be performed. If diagnosed with BPH but not pursuing treatment options, men typically receive regular checkups and report increased BPH symptoms to the physician. If symptoms occur and cause discomfort, affect activities of daily living, or endanger health, drug treatment or surgery may be recommended. Treatment options for BPH include lifestyle changes (such as adjusting fluid intake), herbal remedies, drug therapy, non-surgical procedures, and surgical procedures. The goals of treatment are generally to improve urinary flow and decrease symptoms associated with BPH. Treatment may delay or prevent the progression of BPH.

Drugs may be used to relieve the common urinary symptoms associated with BPH by either reducing the size of the prostate gland or by slowing the growth of the prostate. Common drug classes used to treat urinary symptoms include alpha blockers, such as doxazosin or tamsulosin, and 5-alpha reductase inhibitors, such as finasteride or dutasteride. The medications may have deleterious side effects such as decreased libido, impotence, retrograde ejaculation, fatigue, dizziness, headache, and decreased blood pressure. If drug therapy does not provide adequate relief of symptoms, surgery may be needed to help correct the prostate gland overgrowth. Further, if more severe symptoms of BPH present, such as recurrent urinary retention, recurrent blood in the urine, recurrent urinary tract infections or bladder stones, drug therapy should not be initiated. Generally, upon presentation of these symptoms, surgery is indicated.

Surgical treatments of BPH may or may not be minimally invasive. For the surgical methods, access to the prostate may be via the urethra, the perineum, or other route.

Non-minimally invasive surgical treatments include Trans Urethral Resection of the Prostate (TURP). Conducted in an operating room under general or spinal anesthetic, a probe is passed through the urethra which scrapes away prostate tissue causing the blockage. Side effects may include retrograde ejaculation, impotence, and a repeat of the procedure if the blockage regrows. U.S. Pat. No. 6,491,672, herein incorporated by reference, discloses one surgery option for treating BPH.

Minimally invasive surgical treatments usually offer the incentives of less pain, faster recovery, lower costs, and use of local anesthesia and a mild sedative. In general, minimally invasive surgical treatments destroy prostate tissue through one of various mechanisms. The destroyed prostate tissue may be reabsorbed by the body and/or discharged into the urine over a period of time. Minimally-invasive surgical treatment options include generation of heat, freezing, chemical means, and ultrasound to destroy prostate tissue. Care must be taken to avoid damaging sensitive areas adjacent the prostate such as nerves controlling sexual functions or the rectal wall.

Various types of laser treatment of BPH exist including laser prostatectomy, interstitial laser coagulation, photosensitive vaporization of the prostate, Holmium laser ablation of the prostate, and Holmium laser enucleation of the prostate (HoLEP). Laser prostatectomy uses a transurethral laser device to cut or vaporize obstructions. Interstitial Laser Coagulation uses a cystoscope through which a fiberoptic probe is directly introduced into the prostate. A small laser fiber is inserted into the prostate through the device inserted in the urethra. Laser energy heats a selected area and the probe may be moved several times to treat all areas of obstruction. Photosensitive vaporization of the prostate (PVP) uses a laser delivered through an endoscope inserted into the urethra. The high-energy laser vaporizes excess prostate tissue and seals the treated area.

For microwave treatment of BPH, a microwave antenna is inserted transurethrally into the prostate. Various forms of microwave treatment may include a cooling means for minimizing patient discomfort and to protect adjacent urethral tissue from damage. Further means may be used to dilate the urethra.

Heat for treatment of BPH may be generated, for example, via laser beams, microwaves, radiofrequency current, or direct current. Other heat application techniques exist for treating BPH including transurethral vaporization of the prostate (TUVP) wherein heat is applied directly to the prostate with a grooved roller bar that vaporizes tissue and water-induced thermotherapy (WIT) to destroy obstructive tissue wherein hot water flows through a transurethrally-placed balloon. U.S. Pat. Nos. 5,928,225 and 6,640,139, herein incorporated by reference in their entirety, further disclose treatment methods using heat.

Non-thermal treatments of BPH include injection of ethanol (see, for example, U.S. Pat. No. 7,015,253) or direct current ablation (see, for example, U.S. Pat. Nos. 7,079,890; 6,733,485; and 6,901,294).

Transurethral ethanol ablation of the prostate (TEAP) may be used to treat BPH and typically uses a cystoscope with a curved needle to inject ethanol in various doses.

High intensity focused ultrasound (HIFU) may be used to treat BPH and noninvasively focuses ultrasound waves to heat and destroy targeted prostate tissue.

Various radiofrequency current treatment methods of BPH have been developed. Some methods are shown and described in U.S. Pat. Nos. 6,106,521; 6,638,275; and 6,016,452, all herein incorporated by reference in their entireties. In one treatment method, transurethral needle ablation, a small needle is inserted into the prostate from the urethra. Radio frequency (RF) energy is applied to the needle to generate heat in specific areas of the prostate. RF frequency based ablation of tissue is done via thermal treatment. Typically, treatment is done until a certain temperature is reached and is then discontinued. An assumption is made that sufficient ablation has occurred on the basis of the reached temperature.

As may be appreciated, many of these BPH treatment methods include transurethral access. Transurethral access may involve catheter-based electrodes within the prostatic urethra (see, for example, U.S. Pat. Nos. 6,517,534 and 5,529,574) or electrodes designed to puncture the urethra and dwell inside the prostate (see, for example, U.S. Pat. Nos. 6,638,275; 6,016,452; 5,800,378; and 5,536,240), transurethral access including balloons for positioning and stabilizing the electrodes (see, for example, U.S. Pat. Nos. 6,517,534 and 7,066,905), transurethral access including means for puncturing the urethral wall (see, for example, U.S. Pat. No. 5,385,544), and transurethral access including means for more accurately placing the electrodes (see, for example, U.S. Pat. No. 6,638,275).

Accordingly, a need exists in the art for a minimally invasive low power, non-thermal method of treating prostate tissue via direct current ablation.

BRIEF SUMMARY

Systems and methods for treating tissue, and particularly systems and methods for non-thermal ablation of tissue, are provided. In various embodiments, the systems and methods use a non-implantable system employing direct current ablation for targeting the area to be treated. DC current ablates tissue by imparting extreme pH into the tissue surrounding electrode. In general, the systems and methods may be used to treat any form of tissue where ablation is desired including, for example, adipose tissue, muscular tissue, glandular tissue, nodular tissue, and fibrous tissue. In specific embodiments, the systems and methods may be used to treat benign prostatic hypertrophy or hyperplasia (BPH). In other embodiments, the systems and methods may be used to treat cancerous tissue. One skilled in the art will appreciate that specifics of the systems and methods may be modified for access to various sites in the body for treating different tissues. In one embodiment, a minimally invasive method for treating prostate tissue via direct current ablation is provided. The method includes inserting a catheter into the urethra such that a portion of the catheter remains outside of the body when the catheter is in a treatment position proximate the prostate, deploying a fixation element associated with the catheter to fix the catheter in the treatment position, and deploying a plurality of electrodes through the catheter into the prostate. The method further includes determining treatment parameters and inputting treatment parameters into at least one of a power source and a processor. A direct current of between approximately 10 and 50 mA and a power of less than 3200 mW is applied to the electrodes using a power source wherein the direct current is applied based on the treatment parameters. At least one of a high pH and a low pH is imparted by at least one of the electrodes upon application of the direct current such that a necrotic zone in the treatment zone is created. Application of the direct current is substantially non-thermal. The application of direct current to the treatment area is stopped once the treatment parameters are reached. The application of current to the electrodes is done in between approximately 15 and 45 minutes with the catheter in a single treatment position.

In a further embodiment, a non-implantable minimally invasive system for treatment of prostate tissue via direct current ablation is provided. The system includes a catheter, a plurality of electrodes, a power source, and a fixation element. The catheter is a transurethral catheter for insertion into the urinary tract, wherein a portion of the catheter remains outside of the body when the catheter is in a treatment position proximate the prostate. The plurality of electrodes are positioned for deployment through and outwardly from the catheter. An active area of at least one electrode delivers a charge to impart a high pH or a low pH such that a necrotic zone is created to form a field of treatment. The power source receives treatment parameters and applies direct current and power to the plurality of electrodes based on the input parameters. The direct current is applied at a magnitude of between approximately 10 and 50 mA per electrode and the power is applied at between approximately 20 and 3200 mW of power per electrode. The fixation element operably coupled with the catheter for maintaining the catheter in the treatment position during treatment. Ablation of tissue using the system is substantially non-thermal.

A further embodiment of a minimally invasive method for treating prostate tissue via direct current ablation is also provided. The method includes inserting a catheter into the urethra such that a portion of the catheter remains outside of the body when the catheter is in a treatment position proximate the prostate. The method further includes deploying a fixation element in the urinary bladder, the fixation element being operably coupled to the catheter and operating to fix the catheter in the treatment position, and deploying between approximately 4 and 8 electrodes a distance of approximately 14 to 22 mm into both lateral lobes of the prostate. The method includes determining treatment parameters and inputting treatment parameters into at least one of a power source and a processor. The method then includes applying between approximately 10 and 50 mA of direct current and less than 3200 mW of power to deliver a charge of between approximately 15 and 72 coloumbs to the electrodes using a power source. The direct current applied is based on the treatment parameters. At least one of a high pH and a low pH is imparted by at least one of the electrodes upon application of the direct current such that a necrotic zone in the treatment zone is created. Application of the direct current is substantially non-thermal. Application of direct current to the treatment area is stopped once the treatment parameters are reached. The application of current to the electrodes is done in between approximately 15 and 45 minutes with the catheter in a single treatment position.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

BRIEF DESCRIPTION OF THE DRAWINGS

FIG. 10b illustrates an end view of the catheter of the system of FIG. 10a.

FIG. 22b illustrates an electrical diagram of the embodiment of FIG. 22a.

FIG. 23b illustrates the system of FIG. 23a.

DETAILED DESCRIPTION

Systems and methods for treating tissue, and particularly systems and methods for non-thermal ablation of tissue, are provided. In various embodiments, the systems and methods use a non-implantable system employing direct current ablation for targeting the area to be treated. DC current ablates tissue by imparting extreme pH into the tissue surrounding electrode. DC current ablation uses low power to treat tissues and creates necrosis without a significant increase in tissue temperatures. In general, the systems and methods may be used to treat any form of tissue where ablation is desired including, for example, adipose tissue, muscular tissue, glandular tissue, nodular tissue, and fibrous tissue. In specific embodiments, the systems and methods may be used to treat benign prostatic hypertrophy or hyperplasia (BPH). In other embodiments, the systems and methods may be used to treat cancerous tissue and benign tumors. One skilled in the art will appreciate that specifics of the systems and methods may be modified for access to various sites in the body for treating different tissues.

Ablation of pathologic tissue can be performed using low level DC current. This may be done by powering multiple electrodes and imparting a high pH at one polarity electrode and a low pH at the opposite polarity electrode. Generally, DC ablation resists diffusing across tissue boundaries and thus can be used to treat tissue with minimal concern to affecting adjacent tissues. Further, in systems employing a plurality of electrodes, treatment may be done with relatively slow application of DC current with the total treatment time reduced by the plurality of electrodes.

System Overview

Figure 1:
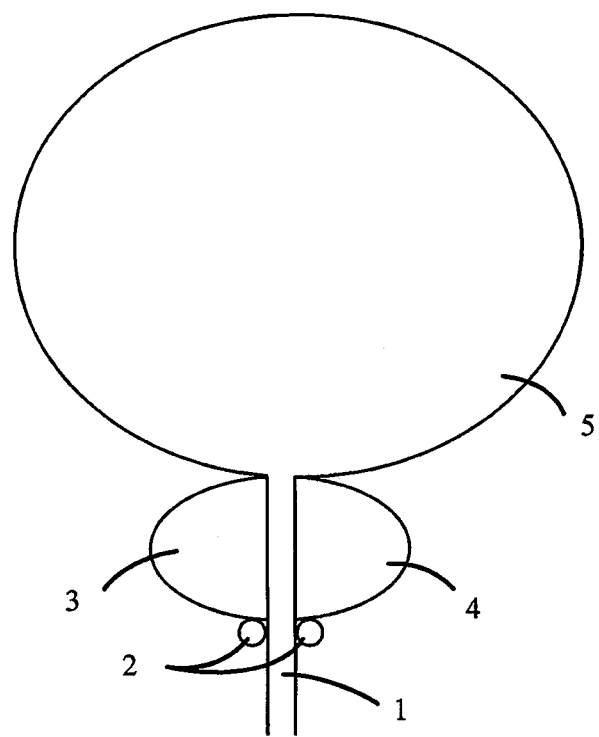
FIG. 1 illustrates a block anatomy diagram of the prostate area.
Figure 2A:
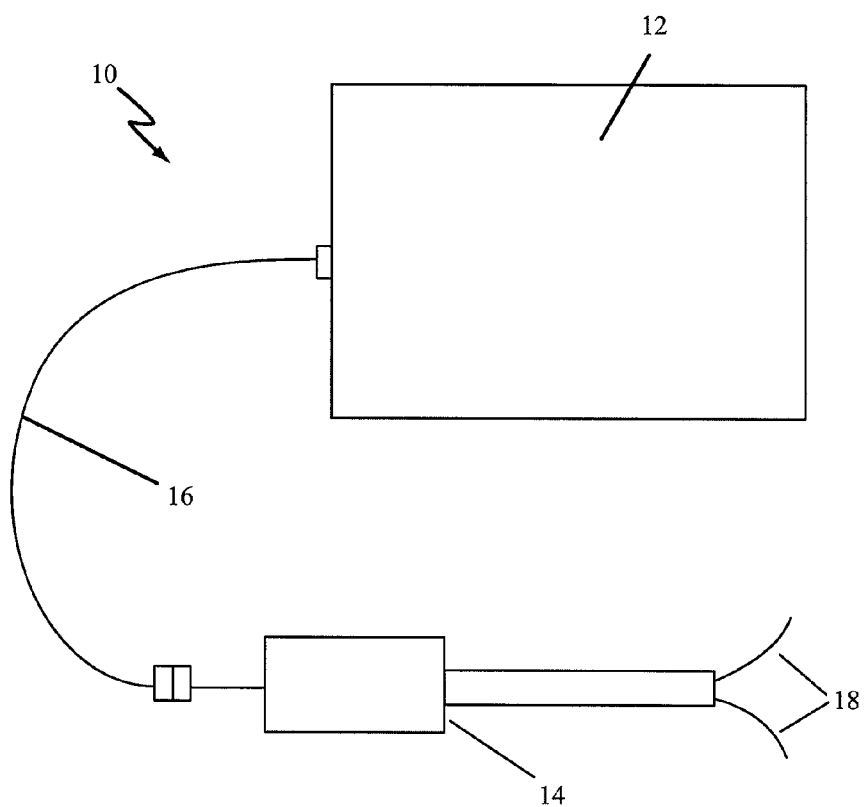
FIG. 2a illustrates a system for treating tissue, in accordance with one embodiment.

FIG. 2a illustrates a basic system configuration. As shown, the system 10 includes a generator 12, a catheter 14, electrodes 18, and a cable 16 running from the generator 12 to the catheter 14. The catheter 14 may be inserted in the body to a desired location for tissue treatment. Once positioned, the electrodes 18 may be deployed, for example through the catheter 14. To treat tissue, power is provided by the generator 12 to the electrodes 18. The electrodes then apply a DC current to a treatment area of the tissue. The tissue is thus treated by DC ablation in a non-thermal manner.

Figure 2B:
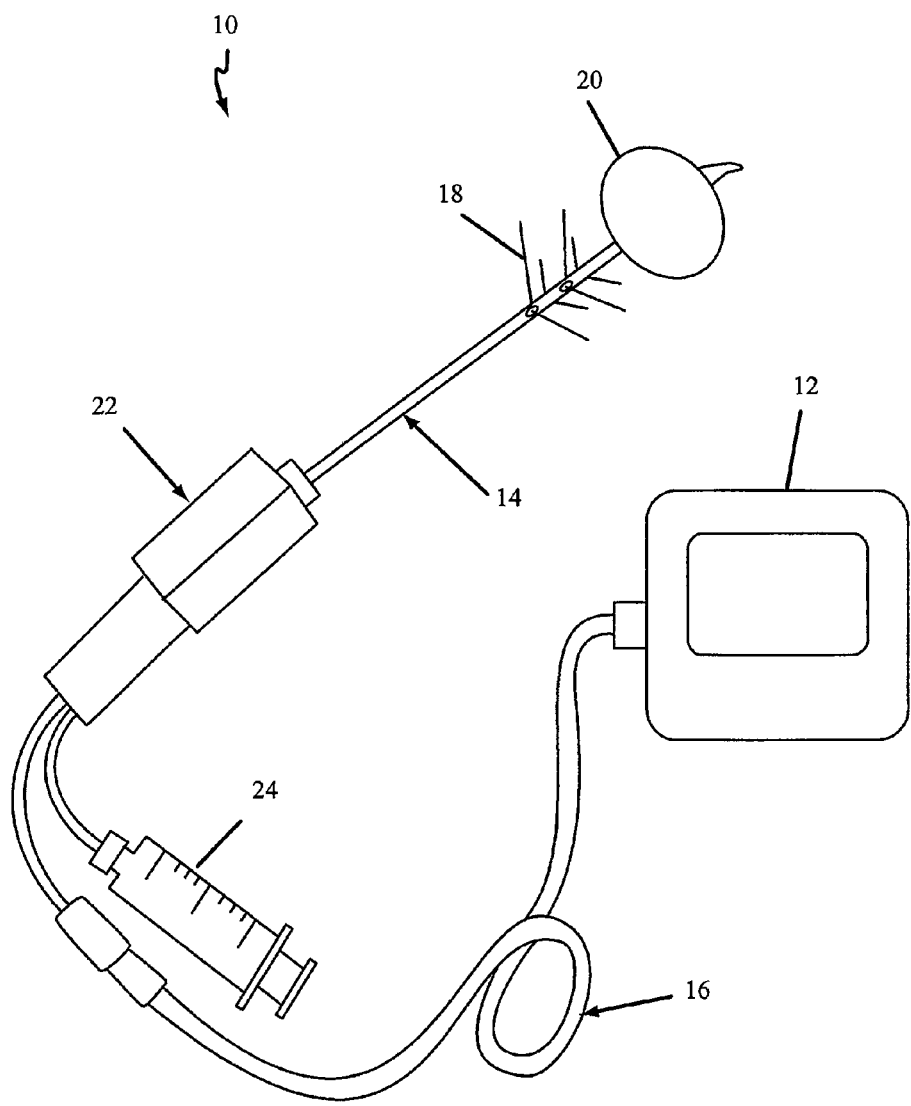
FIG. 2b illustrates a system for treating BPH, in accordance with one embodiment.

FIG. 2b illustrates an embodiment of the system of FIG. 2a configured for treatment of prostate tissue (or BPH treatment). As shown, the system 10 includes a generator 12, a catheter 14, an electrical connection 16 from the generator to the catheter, a plurality of electrodes 18, a mechanism 22 for deploying the electrodes, a stabilization mechanism or fixation element 20, and a mechanism 24 for deploying the stabilization mechanism. In various embodiments, the catheter 14 may be a transurethral catheter, In some embodiments, the electrodes 18 may be provided as pairs of electrodes. In some embodiments, an electronic control system may be included. The system and method may be used for treatment of BPH via deployment of the one or more electrodes through the transurethral catheter and application of direct electrical current to the one or more electrodes. In alternative embodiments, the system may comprise a catheter for other laparascopic or percutaneous access to a treatment site. The electrodes produce a field of treatment that covers a predictable area of the target tissue. When deployed transurethrally, the electrodes can produce a field of treatment covering a predictable area of prostatic tissue. A necrotic zone may be created around each of the electrodes and the created necrotic zones coalesce to form the field of treatment. The field of treatment begins at the electrode and diffuses out generally passively.

The electrodes may be provided in any number, may have various shapes, may have various deployment configurations, and may be manufactured of various materials, as shown and discussed in copending U.S. patent application Ser. No. 12/544,119, herein incorporated by reference in its entirety. In some embodiments, the electrodes are provided in pairs. The ability to control the mechanical length, angle, and electrical polarity of each electrode, as well as the amount of current passing through each electrode allows debulking of a predictable region in a controlled manner while reducing risk of damage to adjacent, non-targeted areas. Generally, application of DC ablation to treat tissue will not result in scar tissue such as arises from other forms of treatment.

In the embodiment shown in FIG. 2b, the electrodes 18 are provided as four electrode pairs, each electrode being generally cylindrical. As shown, two of the electrode pairs comprise shorter electrodes and two of the electrode pairs comprise longer electrodes. Each electrode pair comprises an anode and a cathode. An anode is defined as the electrode with higher voltage potential. A cathode is defined as the electrode with the lower voltage potential. In the embodiment of FIG. 2b, the electrodes deploy outward from the catheter. Such outward deployment may be, for example, radial or may be linear. Generally, the electrodes may be coupled to the catheter or to a support structure in the catheter. As can be appreciated, the electrodes and their coupling with the catheter or a support structure provided within the catheter may be configured to extend from the catheter at different angles, for different lengths, etc. Angles of extension may further be influenced by the shape and configuration of the routing holes. The various system configurations may be designed based on the tissue to be treated and a selected access route to the tissue to be treated. In some embodiments, for example, the system may be configured for treatment of prostate tissue, or more specifically, for treatment of a large region of prostate tissue.

The electrodes 18 are configured for puncture and proper placement of the electrode tip to create a desired treatment area. The electrodes 18 further are configured to resist corrosion. In some embodiments, the electrodes 18 may comprise a nitinol wire with a corrosion resistant coating. The corrosion resistant coating may be, for example, platinum. In some embodiments, the electrodes may be configured to be atraumatic. In an embodiment comprising needle electrodes, for example, the tip of the needle electrode may be self-introducing. Using a transurethral approach, deployment of the electrodes comprises extension from the transurethral catheter and through the urethra. Accordingly, the electrodes pierce the urethra. Thus, in embodiments for treating BPH, the electrode tip may be sufficiently sharp to penetrate the urethra.

In use, current is supplied to the electrodes to create a reaction around the electrodes to change the structure of the tissue in a treatment zone around the electrodes. The system thus may further include a generator for supplying current to the electrodes. The non-thermal ablation system generally is a lower power system, using, for example, on the order of milliwatts. The system thus does not create significant heat during treatment, thus mitigating side effects often associated with thermal treatment. The size and shape of the treatment zone varies depending on, at least, treatment time, current delivered, electrode size and shape, and positioning of the electrode relative to tissue boundaries. As a general matter, by using a plurality of electrodes that are properly placed, treatment may be done at a relatively slow rate but the total treatment time may be relatively fast. The shape of the treatment zone around a cylindrical electrode, such as shown in FIG. 2b, is approximately an ellipsoid or cylinder with hemispheric ends with the distance from the boundary of the treatment zone and the surface of the electrode having a generally consistent radius, referred to herein as the radius of treatment.

Figure 3A:
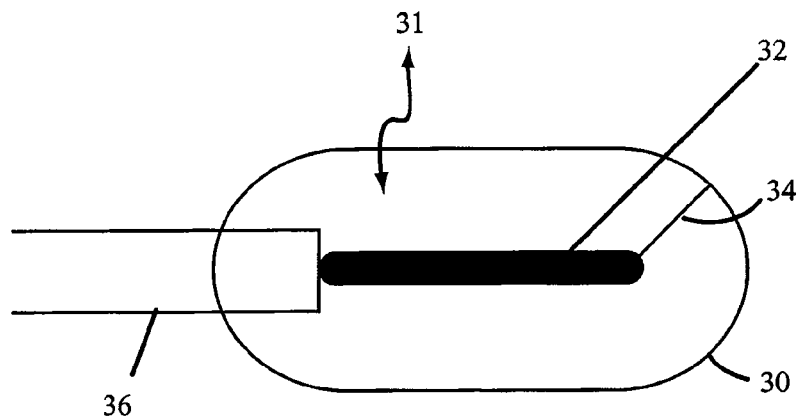
FIG. 3a illustrates a side view of an electrode, radius of treatment, and treatment zone, in accordance with one embodiment.
Figure 3B:
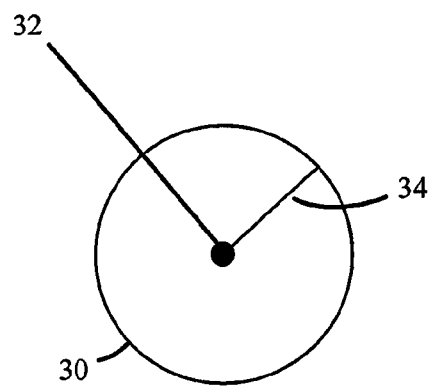
FIG. 3b illustrates an end view of an electrode, radius of treatment, and treatment zone, in accordance with one embodiment.

FIG. 3a illustrates a side view and FIG. 3b illustrates an end view of an active electrode. As shown, the electrode 31 includes an active portion 32 and an insulated portion 36. The insulated portion 36 of the electrode is resistant to the corrosive environment created during ablation. FIGS. 3a and 3b further illustrate the radius of treatment 34, treatment zone 30 associated with the active portion 32 of the electrode 31.

Figure 4A:
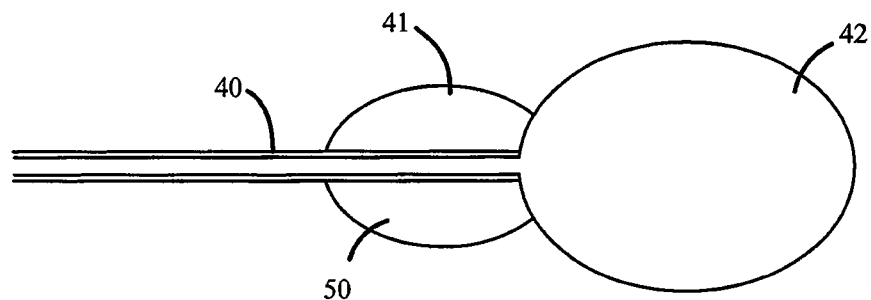
FIG. 4a illustrates anatomy of a prostate region prior to deployment of a device for treating tissue.
Figure 4B:
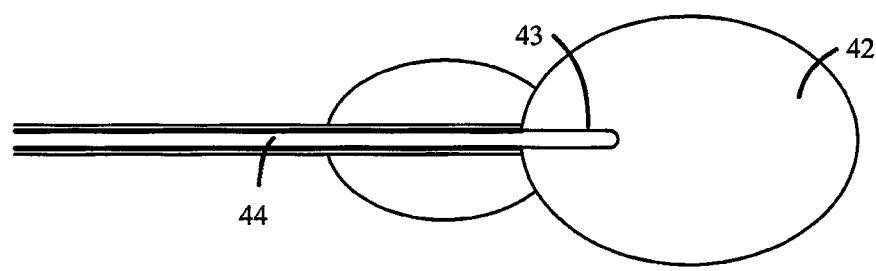
FIG. 4b illustrates transurethral insertion of a catheter for deployment of a device for treating tissue, in accordance with one embodiment.
Figure 4C:
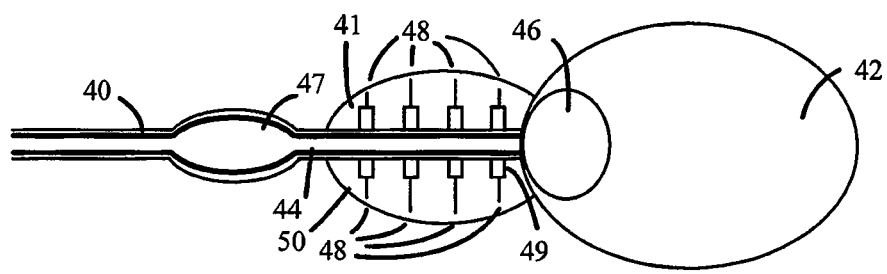
FIG. 4c illustrates deployment of electrodes, in accordance with one embodiment.

FIGS. 4a-4c illustrate deployment of a device for treating tissue in a prostate region, in accordance with one embodiment. Specifically, FIGS. 4a-4c illustrate the device relative the urethra 40, prostate gland 41, prostate capsule or wall 50, and bladder 42. Before treatment, the tissue to be treated may be assessed to determine appropriate treatment protocol. FIG. 4a illustrates a simplified diagram of the anatomy of a prostate region prior to deployment of a device for treating tissue. FIG. 4b illustrates transurethral insertion of the catheter 44 and shows the distal end 43 of the catheter 44. FIG. 4c illustrates deployment of the electrodes 48 and their insulation sleeves 49 through the catheter 44, with the catheter 44 generally fixed in place by one or more balloons 46, 47 (or other fixation element).

FIG. 4b illustrates an embodiment for BPH treatment wherein a catheter 44 is inserted transurethrally. In various embodiments, the catheter 44 may be flexible or semi-flexible or semi-rigid distally from the entrance of the urethra, as deployed. In one embodiment the catheter body has a flex modulus of between about 0.4 and 3 GPa. The catheter may be advanced with the guidance of a trans-rectal ultrasound (TRUS). In FIG. 4b, the distal end 43 of the catheter 44 is shown inserted in the bladder 42. The catheter 44 may include one or more balloons 46 and 47, as shown in FIG. 4c. To fix the system in place, one balloon 46 is expanded within the bladder and one balloon 47 is expanded in the urethra 40. Other anchoring mechanisms or fixation elements may alternatively be used. In some embodiments, the balloon 46 expanded within the bladder 42 assists in placement of the catheter 44. For example, the balloon 46 may be inflated after the catheter tip has entered the bladder and the catheter may be retracted until resistance is felt by the balloon 46. The balloons further may assist in maintaining the catheter in a treatment position. Various methods of imaging, such as ultrasound using a rectal probe, may be used to help position the catheter.

FIG. 4c illustrates electrode deployment after anchoring of the catheter. In the embodiment of FIG. 4c, the catheter 44 includes eight needle electrodes 48 at four different positions on the catheter 44. The electrodes 48 and their electrical insulation sleeves 49 pierce the urethra 40 and enter the prostate 41. As shown, the length of the electrodes 48 may be varied to optimize the field of treatment for the given size and shape of the prostate 41. In the deployment position, none of the electrodes 48 pierce the prostate wall 50. After the electrodes have been positioned, current is applied to create acidic and basic zones and thus ablate tissue in the treatment zone. In embodiments comprising eight electrodes, the system may be used to create eight necrotic zones in a single deployment. Thus, the treatment may be performed with a single deployment, employing relatively slow treatment with respect to application of current but having relatively fast treatment time because all treatment zones may be formed substantially simultaneously. This decreases physician time and burden to deliver the treatment to patients.

In some embodiments for treatment of BPH, the cathode may be placed proximate the bladder neck or base of the prostate. A cathode so placed creates a large area of necrosis with less relative variation. Because of the edemic reaction at the cathode, the healing response and resorption of tissue into the body (and associated relief of symptomatic BPH) is accelerated. The area closest to the bladder neck in the prostate is responsible for the greatest contribution to lower urinary tract symptoms due to BPH. The anode may be placed closer to the verumontanum or as an indifferent electrode. Another embodiment includes placing the cathodes in the lateral posterior quadrant of the tissue relative to the urethra and placing the anodes in the lateral or lateral anterior quadrant of the tissue relative to the urethra. A treatment zone forms around each of the electrodes and diffuses out generally passively. Thus, the electrodes may be placed in the tissue relative to each other such that the treatment zones overlap and coalesce. In one embodiment an indifferent electrode is used as either the anode or cathode in addition to the electrodes in the catheter which create the treatment zones. The indifferent electrode can be a patch electrode that makes contact with the skin of the patient. In one embodiment the patch is placed on the buttocks of the patient. The indifferent electrode may have a substantially large surface area to reduce the electrochemical affect on the skin. In one embodiment indifferent electrode incorporates a flushing system to maintain a neutral pH at the surface of the skin-electrode interface.

Method of Treatment

Figure 5:
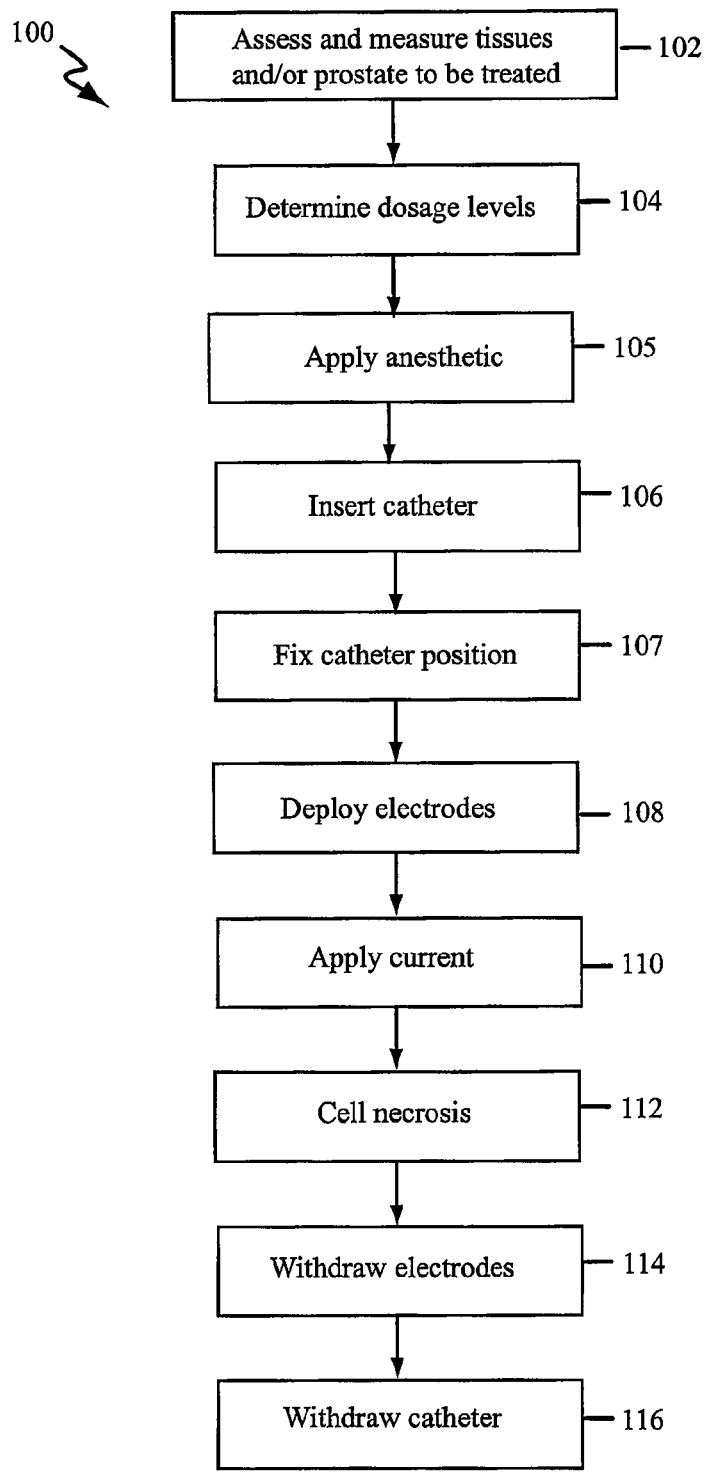
FIG. 5 illustrates a block diagram of a method for treating tissue, in accordance with one embodiment.

FIG. 5 illustrates a block diagram of a method 100 for treating tissue. In the embodiment shown, the method comprises assessing and measuring the prostate or other tissue to be treated [block 102], determining dosage levels [block 104], application of an anesthetic [block 105], inserting a catheter [block 106] and fixing the position of the catheter with a fixation element [block 107], deploying electrodes via the catheter[block 108], applying current to the electrodes to create acidic and basic treatment zones [block 110], cell necrosis [block 112], withdrawal of the electrodes [block 114], and withdrawal of the catheter [block 116]. It is to be appreciated that, in some embodiments, not all of these steps may be performed and/or additional steps may be performed. Further, in some embodiments, one or more of the steps may be performed in a manner other than specifically disclosed herein.

In treatment of BPH, prostate size may vary considerably and selection of appropriate number and size of electrodes to deploy may vary based on size of the prostate. Generally, using systems and methods such as disclosed herein, a minimum of 4 electrodes will be deployed. In some embodiments, eight electrodes, with eight associated treatment zones are provided and deployed in a single deployment. To evaluate the number and size of electrodes for deployment and/or dosage levels, it may be desirable to examine the patient to determine size of the tissue area to be treated. Such examination may be visual, tactile, or other. In one embodiment, examination may be done using a cystoscope, a tubular instrument used to visually examine the interior of the urinary bladder and urethra. In various embodiments, the location for electrode deployment may be determined by estimating the size and shape of the prostate through cystoscopy and/or transrectal ultrasound (TRUS) and/or other suitable imaging method. Other options include CT, MRI, PET, or X-ray. Treatment zone size may also be determined to minimize interaction with the prostate capsule and the prostatic urethra. Minimizing treatment interactions with the capsule and prostatic urethra will reduce the amount of irritative urinary symptom after treatment. An appropriate system configuration thus may be selected based on the prostate size to be treated to minimize these interactions. Dosage levels may be determined based on the assessed treatment area. The desired treatment area can be determined by measuring the overall prostate dimension such as transverse width, sagital length, and anterior to posterior height. Generally, the most important anatomical dimension to determine treatment may be the prostate transverse width. Diffusion through tissue is typically predictable, thus facilitating dosage setting.

In one embodiment the generator is configured to display the predicted areas of necrosis over an uploaded image from ultrasound. In other embodiments, other imaging devices may be used to provide such imagery. The size and shape of the treatment zone varies with the charge setting inputted into the generator. In some embodiments the generator is configured to communicate with an ultrasound machine overlaying the predicted treatment zone on the ultrasound image. In embodiments wherein the system is used for treatment of prostate, imaging may be used prior to insertion of the system. Such imaging may be, for example, a rectal ultrasound whereby the prostate is measured. Measurements of the prostate may then be compared to a table to determine appropriate length of insertion and dose for treatment.

Block 104 of FIG. 5 may include entry of input treatment parameters into the generator. In some embodiments, the generator may include switches, keys or buttons for the entry of one or more input treatment parameters by the user of the system and those input treatment parameters may be used by the generator to control the delivery of current. During treatment, the generator may compare measured treatment parameters with input treatment parameters to determine when to pause or stop the treatment. In one embodiment, the input treatment parameter may be dose (charge) in coulombs. During treatment, the generator stops treatment when the measured charge is greater than or equal to the charge entered by the user. In another embodiment, input treatment parameters may be current level and time. During treatment, the generator may stop treatment when the measured charge is greater than or equal to the product of the current level and time input parameters. In another embodiment, the input treatment parameter may be current level. During treatment, the generator may pause or stop treatment if the measured current level exceeds the current level input parameter. In another embodiment, the input treatment parameter may be time with a predetermined current level.

The following look-up tables can be a guide for determining the charge to be delivered and the length of insertion of the electrodes into prostates with varying transverse widths to optimize treatment.

Table 1 shows optimized treatment settings for a catheter which has electrodes that extend outward from the catheter generally perpendicular from the catheter body (Extension angle between 60 and 120 degrees) (The active length of the electrode is assumed to be 6 to 8 mm in this table):

TABLE 1

| Prostate Transverse Width (mm) | Dose or Charge (C) | Expected Treatment Zone Radius around each electrode (mm) | Electrode Extension Length (mm) |
| --- | --- | --- | --- |
| 30-40 | 36-48 | 5-7 | 13 |
| 40-50 | 40-52 | 6-8 | 16 |
| >50 | 48-60 | 7-9 | 20 |

Table 2 shows optimized treatment setting for a catheter which has electrodes that extend outward from the catheter towards the catheter tip with an extension angle of 45 degrees to 30 degrees. The active length of the electrode is assumed to be 6 to 8 mm in this table:

TABLE 2

| Prostate Transverse Width (mm) | Distal Electrode Insertion Point from Fixation Element in Bladder (mm) | Optimal Dose or Charge (C) per electrode | Expected Treatment Zone Radius around each electrode (mm) | Electrode Extension Length (mm) |
| --- | --- | --- | --- | --- |
| >30 | 14-16 | 28-36 | 4-6 | 16 |
| >30 | 16-18 | 36-48 | 5-7 | 18 |
| >35 | 18-20 | 36-48 | 5-7 | 20 |
| >40 | 20-22 | 48-60 | 7-9 | 22 |

Table 3 shows optimized treatment setting for a catheter which has electrodes that extend outward from the catheter towards the catheter tip with an extension angle of 60 degrees to 45 degrees. The active length of the electrode is assumed to be 6 to 8 mm in this table:

TABLE 3

| Prostate Transverse Width (mm) | Distal Electrode Insertion Point from Fixation Element in Bladder (mm) | Optimal Dose or Charge (C) per electrode | Expected Treatment Zone Radius around each electrode (mm) | Electrode Extension Length (mm) |
| --- | --- | --- | --- | --- |
| >30 | 12-14 | 28-36 | 4-6 | 16 |
| >35 | 14-16 | 36-48 | 5-7 | 18 |
| >40 | 15-17 | 36-48 | 5-7 | 20 |
| >45 | 16-18 | 48-60 | 7-9 | 22 |

Table 4 shows optimized treatment setting for a catheter which has electrodes that extend outward from the catheter towards the catheter tip with an extension angle of 30 degrees to 15 degrees. The active length of the electrode is assumed to be 6 to 8 mm in this table:

TABLE 4

| Prostate Transverse Width (mm) | Distal Electrode Insertion Point from Fixation Element in Bladder (mm) | Optimal Dose or Charge (C) per electrode | Expected Treatment Zone Radius around each electrode (mm) | Electrode Extension Length (mm) |
| --- | --- | --- | --- | --- |
| >30 | 16-18 | 20-28 | 3-5 | 16 |
| >30 | 18-20 | 24-32 | 4-5 | 18 |
| >30 | 20-22 | 28-36 | 4-6 | 20 |
| >30 | 22-24 | 28-36 | 4-6 | 22 |

To determine how many electrodes should be used to treat a prostate, a cystoscopy or ultrasound should be done to measure the distance between the bladder neck and the verumontanum. If the measurement is less than 2.5 cm the patient is not well suited to be treated with a catheter that has electrodes that angle away from the catheter of less than 60 degrees upon electrode extension (extension angle). Table 5 shows the number of electrodes that should be used in treating prostates with varying distances between the bladder neck and verumontanum with catheters with different extension angles. This assumes that 4 electrodes are placed in each plane along the urethra and each plane is spaced between 6 and 12 mm.

TABLE 5

| Cystoscopy Measurement between bladder neck and verumontanum (cm) | Optimal # of Electrodes in catheter with extension angle between 90 and 60 degrees | # of Electrodes in catheter with extension angle between 60 and 45 degrees | # of Electrodes in catheter with extension angle between 45 and 30 degrees | # of Electrodes in catheter with extension angle between 30 and 15 degrees |
| --- | --- | --- | --- | --- |
| <2.5 | 4 | NA | NA | NA |
| 2.5-4.5 | 8 | 4 | 4 | 4 |
| >4.5 | 12 | 8 | 8 | 4 |

Figure 6A:
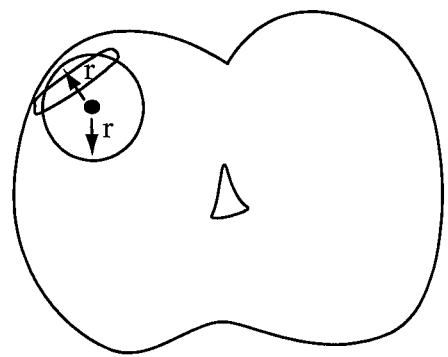
FIG. 6a illustrates a treatment zone for a dose that just touches the capsule, in accordance with one embodiment.
Figure 6B:
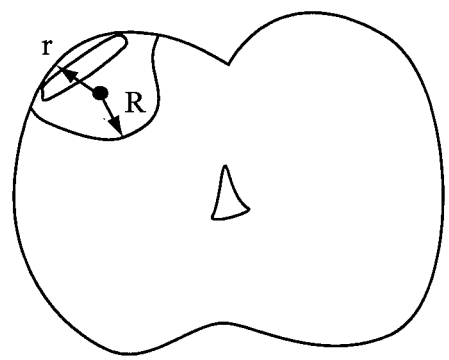
FIG. 6b illustrates a treatment zone for a dose that is overdosed, in accordance with one embodiment.

In some embodiments, the prostate capsule may be used as a safety margin to deliver DC ablation to the periphery zone of the prostate. Because of the capsule around the prostate and the creation of ions using DC ablation, the prostate can be overdosed to effectively treat the periphery zone, especially for applications for treating cancerous tissue. This overdose may range from approximately 160% to approximately 260% of the dose for allowing the ionic gradient to reach the prostate capsule. FIGS. 6a and 6b illustrate treatment zones for a dose that just touches the capsule (FIG. 6a) and a dose that is overdosed (FIG. 6b). A cancer is shown in each of the figures with the treatment radius of each electrode being suitable for treating the cancer. Each of FIGS. 6a and 6b show the same electrode placement. Dose typically may be determined assuming a radius that reaches the capsule but does not extend past the capsule, radius r shown in FIG. 6a. The dose may be increased to effectively increase radius but the radius r towards the capsule will not extend past the capsule because of the anatomy of the capsule. Thus, as shown in FIG. 6b, radius r towards the capsule remains the same but radius R away from the capsule increases. In one embodiment, the treatment radius in FIG. 6a is achieved using a dose of 30 C and results in a radius r of 6 mm. In one embodiment, the treatment radius R in FIG. 6b is achieved using a dose of 78 C and results in a radius R of 10 mm. An algorithm may be developed using routine experimentation for current and charge balancing to produce the desired treatment zone.

In some embodiments, the area for treatment may be prepared for treatment, as shown and discussed in copending U.S. patent application Ser. No. 12/544,134, herein incorporated by reference in its entirety. Unlike many ablation methods, DC ablation does not use extremes of temperature to cause necrosis and therefore can be used safely adjacent vascular structures.

In some embodiments, a saline solution or saline gel may be introduced to provide additional safety margin where ablation of tissue is not desired. In some embodiments, a saline solution with a pH of 7 may be provided adjacent to a treatment area. This substantially prevents the acidic and basic treatment zones from advancing into that area. The neutral pH of the saline dilutes the advancing acidic and basic gradient to a point which does not create necrosis in the tissue in irrigated areas. The saline solution may be delivered to an area by any suitable method. For example, in a first embodiment, saline may be introduced into a body lumen where preservation is desired, such as the urethra, through the therapy delivery catheter or through a separate dedicated irrigation catheter. In a second embodiment, saline may be injected through a needle into a capsule to preserve a certain region within the capsule. In a third embodiment, saline may be injected into a body cavity adjacent to the capsule of the body being treated to preserve adjacent tissue, such as the rectum. Saline saturation of the treatment area may further be done if a concern for dehydration arises. In other embodiments, distilled water may be used as an alternative to saline solution. As discussed with respect to application of current to the electrodes, muscle contractions may arise during treatment. Generally, muscle contractions are undesirable during treatment. A nerve block may be used in some embodiments to minimize patient discomfort during treatment. In some embodiments, anesthetic may be applied. It is to be appreciated, however, that the system and method disclosed herein are significantly more tolerable to patients than previous methods of BPH treatment and may be performed with minimal anesthetic. For example, the methods disclosed herein may be performed with the patient conscious.

Pain management during treatment according to the systems and methods provided herein may be done by local anesthesia. For example, in some embodiments application of anesthesia may comprise introducing a topical anesthetic gel (e.g. lidocaine) into the urethra. This may be done, for example, by injecting into the urethra or coating a catheter that would be inserted and removed prior to inserting the treatment catheter. Thus, in various treatment applications, anesthetic gel may be applied to a transperineal, transrectal, or transurethral catheter for delivery to the prostate or other tissue. In other embodiments, a nerve block may be injected locally or a sedative may be orally ingested or intravenously delivered.

In some embodiments, the method may include visualization, for example to facilitate placement and positioning of the system. Accordingly, visualization elements may be provided as part of the system. Particularly in systems employing a plurality of electrodes, such as eight electrodes, correct positioning can impact results. The positioning of the system impacts positioning of all electrodes and, thus, positioning of all necrotic zones. Accurate placement of transurethral catheters can be optimized with the use of a transrectal ultrasound. Ultrasound imaging may be optimized by designing the catheter or other portion of the system for imaging. The ability to image the system as the system is placed can enhance results and improve safety.

Magnetic resonance imaging may alternatively be used to verify position and treatment for the system for treating tissue as provided herein. In accordance with one method, the catheter is placed and the electrodes are inserted. The patient is positioned for MRI imaging and DC ablation is activated at low levels. MRI is performed, tuned to measure the electromagnetic field of DC current, and therapy is paused. The position of electrodes and treatment region are verified through examination of the MRI image. Generally, the imaging sequence may include electrical currents, via induced magnetic field, or $H^+$ concentration, such as for conventional MRI images, or other sequences such as known to those skilled in the art. In another embodiment fluoroscopy can be used to visualize the position of the catheter, balloon or electrodes during or before treatment.

Angular orientation of the catheter and electrode array can be verified by a physical marker on the body of the catheter or handle that is exposed outside the body. In certain embodiments, this may be a linear marking or a bubble indicator. Such indicator may also be internal to the body and may be seen through imaging such as ultrasound, MRI, CT, or X-Ray The system may be deployed by inserting a catheter proximate the tissue to be treated such that the treatment zone of an electrode deployed from the catheter overlaps the tissue to be treated. The catheter may have a handle provided at a proximal end thereof for handling by a physician, such as a surgeon or urologist. The catheter is inserted until location of the electrodes, as determined with respect to the catheter, is at the desired tissue for treatment. Thus, for example for BPH treatment, the catheter may be inserted into the urethra through the penis until location of the electrodes is in the urethra proximate the prostate. In some embodiments, the catheter may include an anchor for anchoring the catheter in place during treatment. For example, a pair of pneumatically or hydraulically activated balloons may be used to anchor the catheter.

After anchoring (if done) and placement confirmation, the electrodes may be deployed from the catheter. Electrode deployment may be linear, rotational, or a hybrid of linear and rotational. Deployment of the electrodes may be triggered, for example, using a push button trigger, a slide mechanism, or other on the catheter handle. In some embodiments, the catheter may be partially retracted or advanced to expose electrodes provided on a support structure within the catheter. In some embodiments, the electrodes may be deployed through routing holes provided in an outer sheath or sleeve of the catheter. The electrodes may extend generally outwardly from the catheter to enter the tissue to be treated. The position of the electrodes in the tissue affects the treatment zone. More particularly, the treatment zone generally surrounds the electrodes.

In some embodiments, the inserted length of all deployed electrodes may be approximately equivalent. This permits the electrodes to be deployed with a single simple mechanism. In other embodiments, multiple insertion lengths may be used. Such varied insertion lengths may be achieved, for example, with multiple insertion mechanisms or various cam and/or gearing mechanisms. Treatment zones around each electrode may be the same size or may vary one to another. The amount of charge to each electrode may be controlled to influence treatment zones. For example, where varying sizes of treatment zones are desired and each electrode has the same length, different currents may be supplied to the electrodes from independent current sources. Further, in some embodiments, portions of the electrode may be insulated, for example portions closest to the catheter to increase the distance from the active area of the electrode to a structure that is wished to be preserved, for example the urethra. This facilitates preservation of the urethra to minimize post-procedural irritative symptoms such as dysuria, hematuria, and urinary urgency.

After the electrodes have been positioned, current is applied to create acidic and basic zones. Specifically, direct electrical current is applied to the electrodes. In some embodiments, the direct electrical current is applied simultaneously to all electrodes from isolated current sources having individually selectable polarity and charge delivery. The applied current creates an acidic zone around the anode and an alkaline or basic zone around the cathode. Generally, the treatment zone tends to follow, and not cross, a tissue plane. Accordingly, using DC ablation, treatment may be up to the tissue plane. The sizes of the necrotic zones are based on the amount of charge delivered to each electrode, where charge (coulombs) equals current (amperes) multiplied by time (seconds). In some embodiments, the applied current is at a relatively low level such as between approximately 1 mA and approximately 100 mA. Generally, treatment time increases as current decreases. Treatment time decreases as the number of electrodes increases. Treatment time may decrease if impedance decreases and the voltage compliance of the constant current system is low or the system utilizes constant voltage. In accordance with one embodiment, BPH treatment is achieved in approximately 30 minutes when using a 4, 6, 8, or 12 electrode array at 20 mA to deliver the treatment of 36 coulombs per electrode pair. Treatment time is reduced to 24 minutes when the current is increased to 25 mA and delivering 36 coulombs per electrode pair. The systems and methods disclosed herein employ slow, low current, low power treatment. Because of the plurality of electrodes and the substantially simultaneous treatment through all electrodes, total treatment time is nevertheless kept low. Table 6 shows the relationships between current, power, time, charge, and number of electrodes.

TABLE 6

| Current per Electrode Pair (mA) | Impedance per Electrode Pair (ohms) | Power per Electrode Pair (mW) | Time (minutes) | Charge per Electrode Pair (coulombs) | Number of Electrode Pairs | Total Charge (coulombs) |
|---|---|---|---|---|---|---|
| 10 | 400 | 40 | 30 | 18 | 1 | 18 |
| 10 | 700 | 70 | 30 | 18 | 2 | 36 |
| 10 | 1000 | 100 | 30 | 18 | 3 | 54 |
| 25 | 400 | 250 | 30 | 45 | 1 | 45 |
| 25 | 700 | 437.5 | 30 | 45 | 2 | 90 |
| 25 | 1000 | 625 | 30 | 45 | 3 | 135 |
| 50 | 400 | 1000 | 30 | 90 | 1 | 90 |
| 50 | 700 | 1750 | 30 | 90 | 2 | 180 |
| 50 | 1000 | 2500 | 30 | 90 | 3 | 270 |

The power applied to the electrodes is low compared to prior methods for treating BPH. More specifically, the power applied in accordance with systems and methods disclosed herein is on the order of milliwatts in the range of 20 to 3200 mW of power per electrode pair. The power typically used for each electrode pair is between approximately 190 mW (25 mA into a 300 ohm tissue impedance) to 1600 mW (40 mA into a 1000 ohm tissue impedance). A common impedance level seen in tissue is 400 ohms, and treating with 50 mA equates to a required power output of 1000 mW. This low power of treatment delivery allows for insignificant heat transfer to occur between the device and body tissues. This reduces or eliminates pain and discomfort from the heating of surrounding tissues during treatment that are experienced with thermal technologies utilizing significantly higher power. It also reduces or eliminates scarring and long healing times associated with a thermal wound. RF and microwave technologies using thermal energies to create necrosis in soft tissue often have power ranges between 15 and 75 W. The amount of power delivered by a thermal ablation system is not based directly on the measurement of the power delivered, but is based on the temperature measurement resulting from the power delivered. In contrast, the amount of charge delivered by the DC ablation system is based directly on the measurement of the charge delivered, allowing for more precise control of the size of the necrotic zones.

Figure 7:
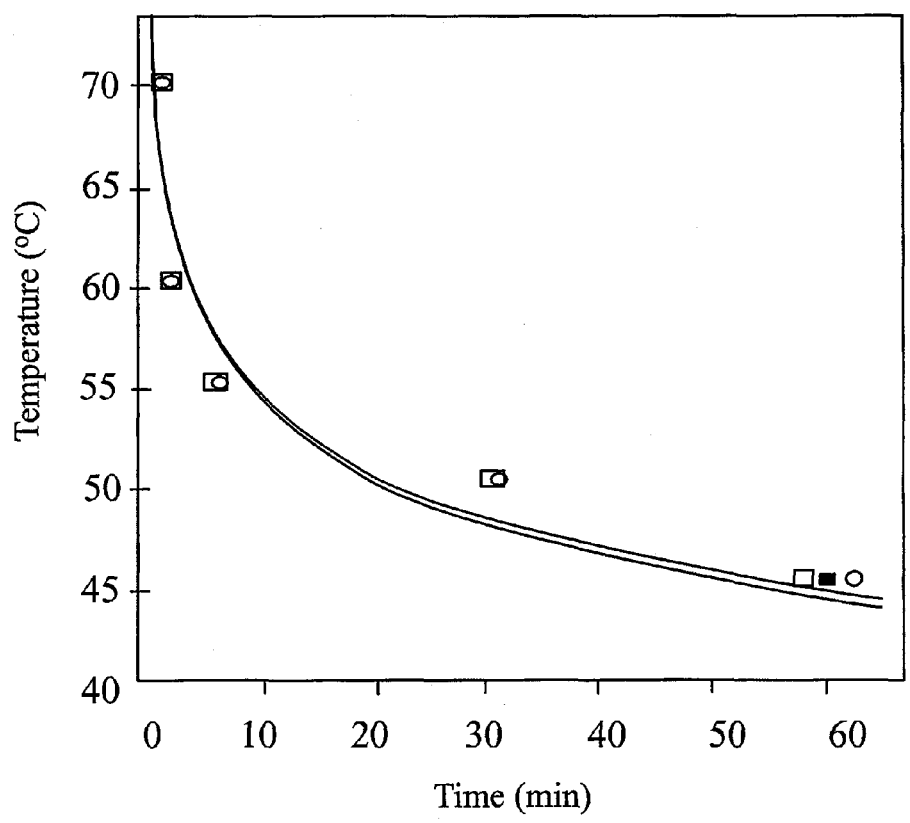
FIG. 7 illustrates a table showing time-temperature relationship for 90% normalized cell death in human BPH tissue from heating.

In order to create substantial cell death a temperature of at least 45 degrees C. or an 8 degree increase in tissue temperature must be maintained for approximately one hour. Substantial cell death occurs over 10 minutes at 55 degrees C. FIG. 7 illustrates the relationship between time and temperature. More specifically, FIG. 7 illustrates the time-temperature relationship for 90% normalized cell death in human BPH tissue from heating. At greater than 100 degrees C. the water present in the tissue boils and can cause impedance increases such that thermal therapy becomes intermittent. RF thermal ablation devices attempt to create tissue temperatures approaching 100 degrees C. to create necrosis with minimal treatment time. RF thermal ablation treatments can last between 1.5 and 5 minutes.

DC ablation applied with up to 50 mA only results in a maximum increase of 4 to 5 degrees C. in the tissues surrounding the electrodes. In one embodiment the DC ablation system is configured to increase the temperature in the tissue to be treated less than 8 degrees to ensure that minimal thermal damage is created in the tissue. Lower currents will cause a lesser change in tissue temperature in the range of 0 to 3 degrees C. This mild increase in temperature does not create necrosis or act as a mechanism in ablating the tissue over the duration of the DC ablation treatment. These calculations are dependent on tissue type and vascularization of the tissue.

Inducing high localized temperatures causes surrounding tissues to also substantially increase in temperature. This may lead to collateral damage of structures outside of the intended treatment area such as, in the case of BPH treatment, the erectile nerves, rectum, or external sphincter. Devices that use radiated energy to heat tissues such as microwave require a rectal temperature probe to ensure that the rectum does not exceed an unsafe temperature. The high temperatures surrounding the treatment area also leads to a burning sensation in the pelvic region. Generally at 45 degrees a heat sensation is perceived. This is exceeded at the prostate capsule during thermal ablation treatments. A non-thermal DC ablation system, such as disclosed herein, does not have either of these concerns due to the low power that is delivered.

A single treatment can be done with no repositioning of the catheter and can be completed in no less than 8 minutes assuming delivering 24 C per electrode at the rate of 50 mA. A single treatment with no catheter repositioning can take as long as 100 minutes assuming delivering 60 C per electrode at a rate of 10 mA. It should be appreciated that, generally, no single treatment should last longer than 45 minutes for patient comfort and physician burden. Thus a treatment of 60 C should be completed at a minimal rate of 22 mA. If more treatment is required the catheter may be repositioned and a second treatment started.

In some embodiments, the electrodes may be generally cylindrical. The shape of the treatment zone for a cylindrical electrode is a cylinder with hemispheric ends and approximates an ellipsoid. By adjusting the electrode length and/or charge delivered, the shape of the ellipsoid can be controlled to make shapes that are cylindrical, oval, or spherical. As current is applied to the electrodes, an ellipsoid treatment zone forms around each electrode. The length of the ellipsoid is approximately equal to the length of the exposed electrode plus the diameter of the treatment zone. If the electrode length is significantly longer than the diameter of the treatment zone, the shape of the zone will be nearly cylindrical. The ends will be round (hemispheres) but the shape will be long and narrow like a cylinder. As the treatment continues, the diameter and length of the zone grow. As a percentage of the previous dimension, the diameter grows faster than the length. As this continues, the shape of the treatment zone becomes more oval than cylindrical and eventually becomes nearly spherical.

Figure 8A:
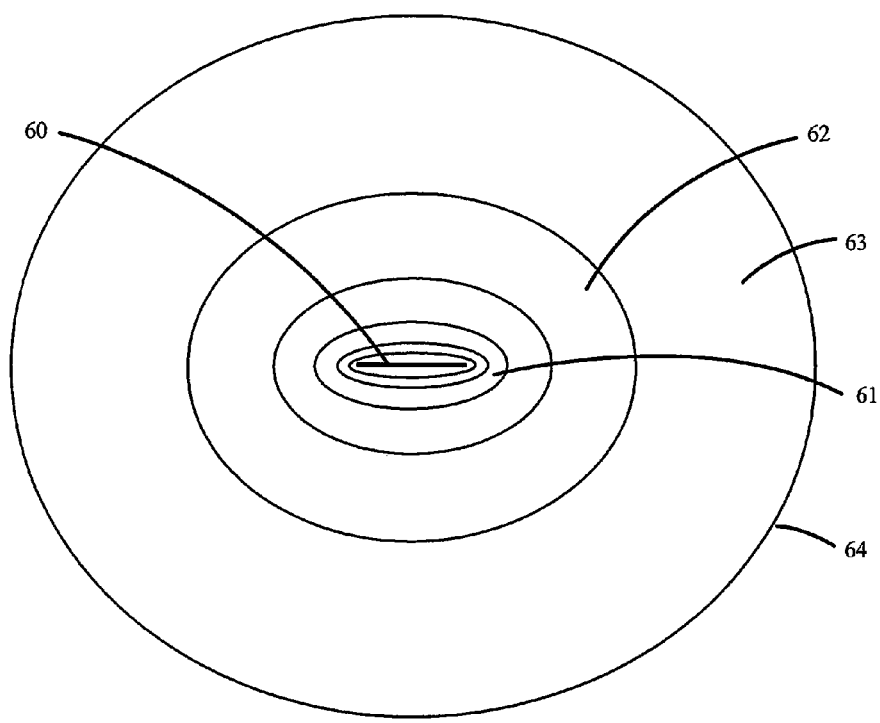
FIG. 8a illustrates changes to the shape of the treatment zone, in accordance with various embodiments.

FIG. 8a illustrates a treatment zone around an electrode 60 wherein the treatment zone is, for the purposes of illustration, divided into 4 zones 61, 62, 63, and 64, extending radially outward from the electrode 60. As shown, the treatment zones 61, 62, 63, and 64 change shape as they extend away from the electrode 60. The zone 61 closest to the electrode is nearly cylindrical while the zone 64 farthest from the electrode is nearly spherical. Accordingly, with electrodes of equal length, treatment zone size as well as shape may vary with different applied currents when treating for an equal amount of time. Treatment shape will vary as well due to the proximity of tissue planes that impede the diffusion of the treatment.

Figure 8B:
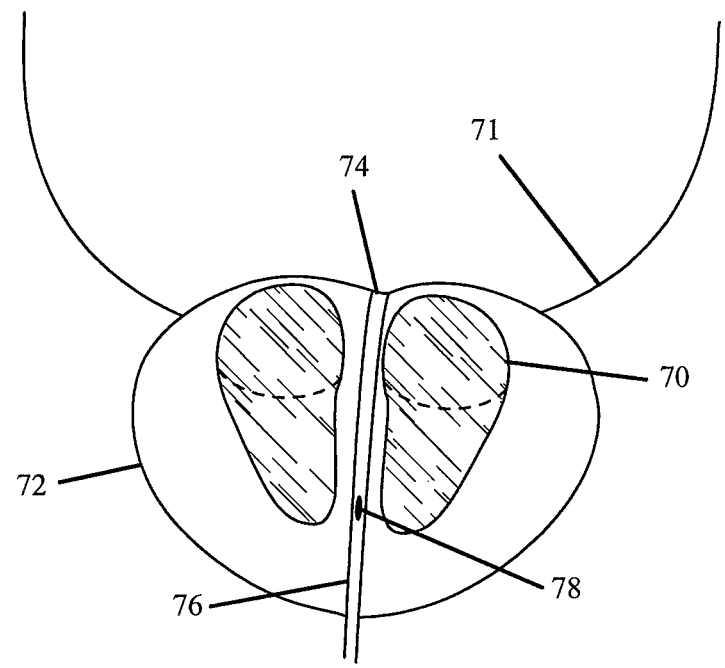
FIG. 8b illustrates coronal tracing of a treatment zone, in accordance with one embodiment.
Figure 8C:
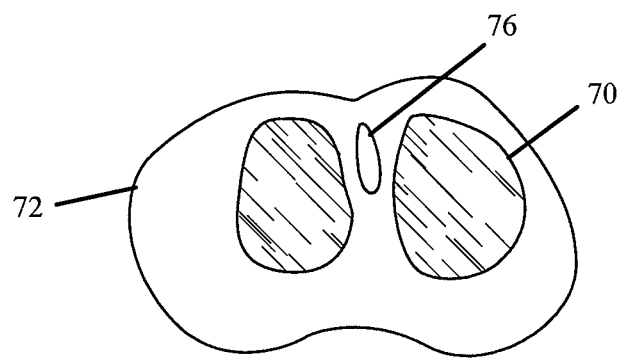
FIG. 8c illustrates transverse tracing of a treatment zone, in accordance with one embodiment.

FIGS. 8b and 8c illustrate a suitable area to create necrosis in the prostate to relieve symptomatic BPH. FIG. 8b illustrates coronal tracing of a treatment zone. FIG. 8c illustrates transverse tracing of a treatment zone. As shown, the treatment zones 70 may be in the lateral lobes 72 of the prostate adjacent to the bladder neck 74 and along the urethra 76 to the verumontanum 78. FIG. 8b also illustrates the bladder 71 for reference. Treating in the treatment zones 70 maximizes symptom relief obtained by treatment as the necrotic tissue is reabsorbed by the body and pressure is removed from the urethra. The urethral interaction of the treatment may be minimized to reduce transient irritative symptoms such as hematuria, dysuria, and urinary urgency. Amount of charge delivered, electrode shape and size, electrode array, electrode positioning, number of electrodes, current level, and electrode insertion length are all factors in treatment.

In another embodiment the electrodes may be staggered such that they do not align. In another embodiment 3, 5, 6, 7, 9, 10, 11, and 12 electrode arrays may be utilized to treat the prostate with DC ablation through the urethra and into the lateral lobes of the prostate. These embodiments are optimized to created treatment zones as prescribed in FIGS. 8b and 8c.

Figure 9A:
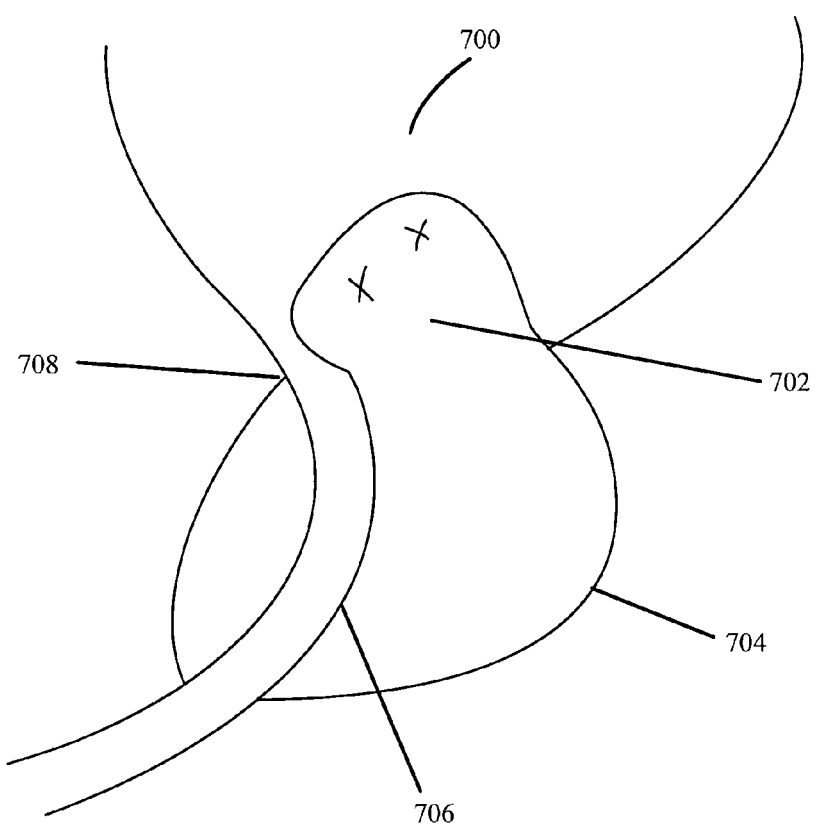
FIG. 9a illustrates a prostate anatomy with a large median lobe that extends up in the bladder.

In some patients it may be desirable to treat the median lobe of the prostate instead or in addition to the lateral lobes. FIGS. 9a-9d illustrate median lobe treatment. FIG. 9a shows a prostate anatomy 704 with a large median lobe 702 which extends up into the bladder 700. A large median lobe 702 can cause a urinary obstruction of the prostatic urethra 706 at the bladder neck 708. Ablating the median lobe can be accomplished using DC ablation by using a modified method and system for treating the lateral lobes as previously described.

Figure 9B:
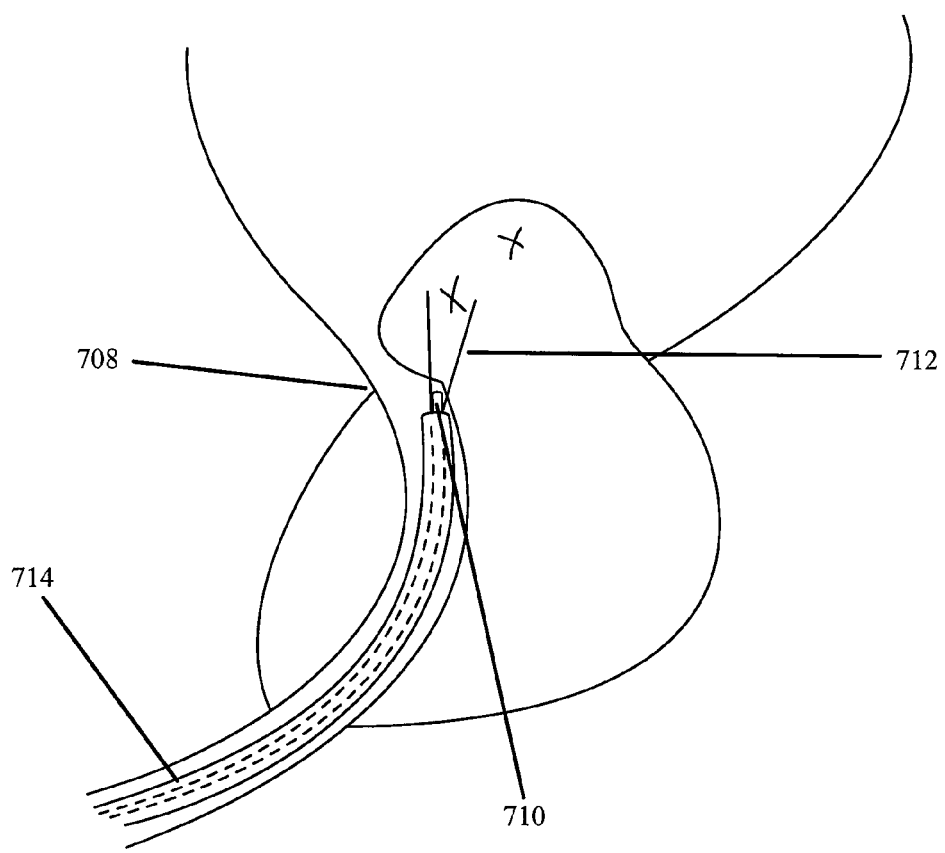
FIG. 9b illustrates positioning of a system for treatment of the median lobe, in accordance with one embodiment.
Figure 9C:
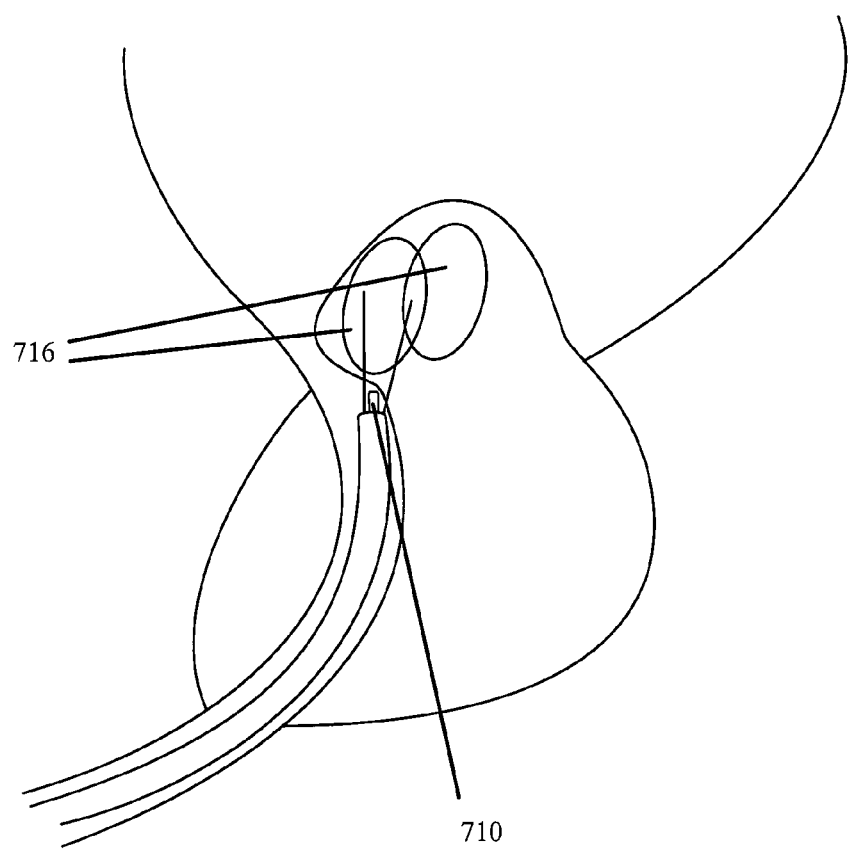
FIG. 9c illustrates treatment zones created through treatment of the median lobe, in accordance with one embodiment.

FIG. 9b illustrates positioning of a system for treatment of the median lobe. FIG. 9c illustrates treatment zones created through such treatment. Treating the median lobe of the prostate can be accomplished using methods described herein. As a preliminary matter, it may be useful to assess the size and position of the median lobe through visualization of the median lobe through Ultrasound, CT, MRI or cystoscopy. A transurethral delivery catheter 714 is routed in proximity to the bladder neck 708 and the area to treat identified by inserting a cystoscope 710 through or adjacent to the delivery catheter. A plurality of electrodes 712, for example between 2 and 4 electrodes, may then be extended into the median lobe under cystoscopy guidance. Insertion may be done either through the urethra near the bladder neck or from the bladder back into the median lobe. After the electrodes are placed a dose or charge of 15 to 72 coulombs per electrode may be delivered creating treatment zones 716 in the median lobe as shown in FIG. 9c. The catheter may be anchored to prevent the electrodes from moving during treatment. After treatment is completed the catheter and cystoscope is removed from the body.

Figure 9D:
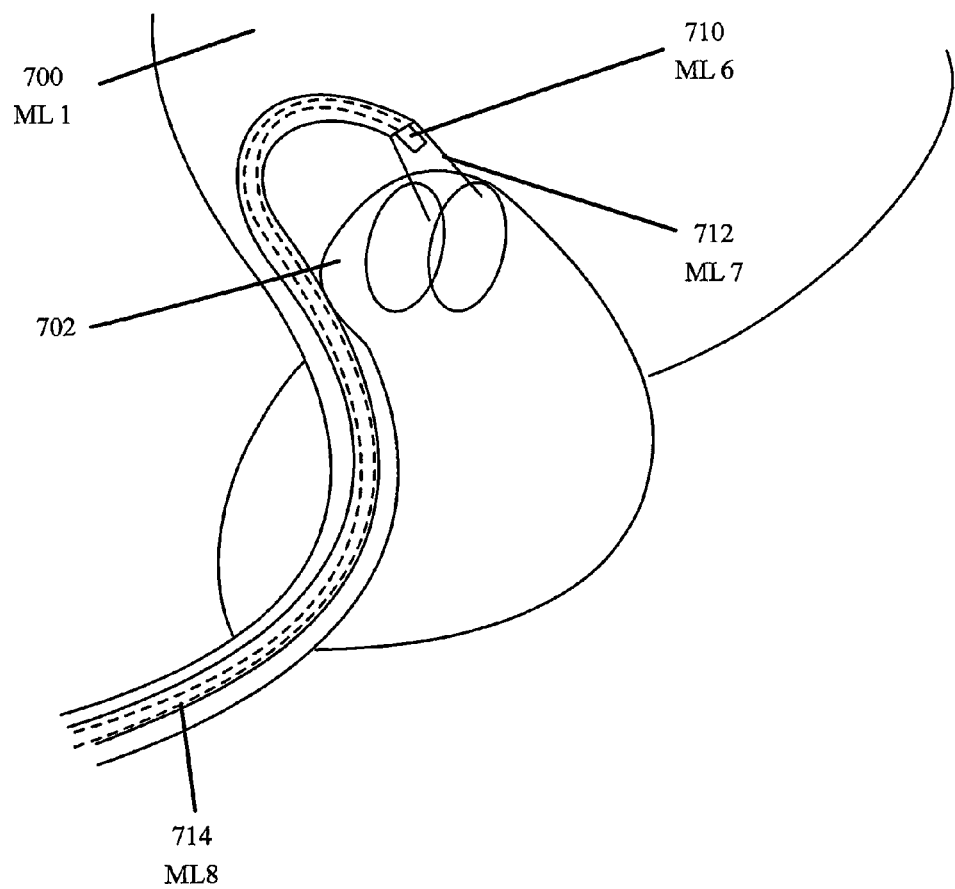
FIG. 9d illustrates an alternative treatment method for treating the median lobe, in accordance with one embodiment.

FIG. 9d illustrates an alternative treatment method for treating the median lobe. As shown, the delivery catheter 714 may be routed into the bladder 700 and then curved back towards the median lobe 702 where the electrodes may be inserted under guidance from a cystoscope.

As may be appreciated by those skilled in the art, similar systems and methods may be used for ablation of tissue in several different areas of the body. Such areas may include, for example, the trachea, stomach, esophagus, rectum, colon, intestine, bladder, uterus, and other tissues accessible from a lumen.

Figure 10A:
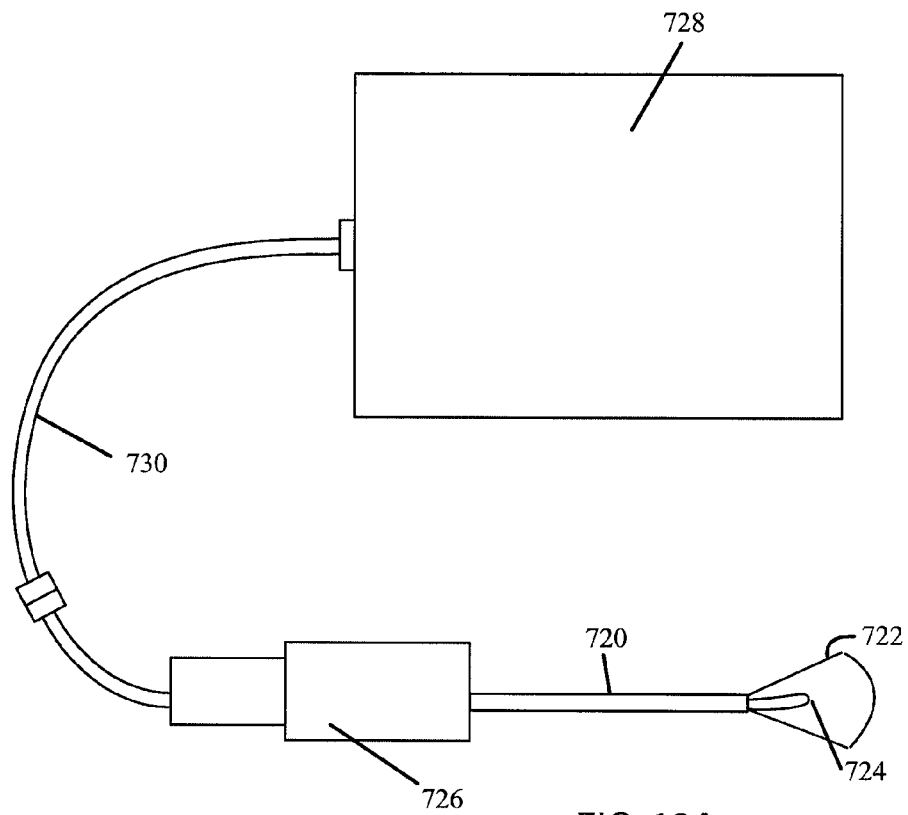
FIG. 10a illustrates a perspective view of a system for median lobe treatment, in accordance with one embodiment.
Figure 10B:
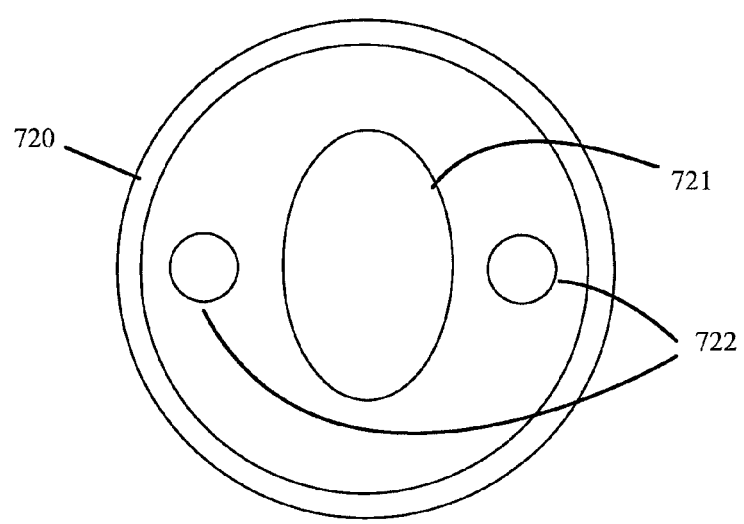

FIGS. 10a and 10b illustrate a specific embodiment of the delivery catheter for a system for treating the median lobe. FIG. 10a illustrates a perspective view and FIG. 10b illustrates an end view. As shown, the system may include a semi-flexible catheter 720 and a plurality of electrodes 722 positioned for extension from the distal tip of the catheter. In some embodiments, between 2 and 4 electrodes may be provided. A cystoscope 724 may be routed down the center of an open lumen 721 of the delivery catheter. The electrodes 722 may be actuated by a mechanism 726 which remains outside of the body during treatment. The delivery catheter is connected to a generator 728 by an extension cable 730. The same generator can be used in the median lobe system as the system for treating the lateral lobes previously described.

In some embodiments, the gas generation and diffusion through tissue can be used to mark the necrotic region. By calibrating current and time to tissue type, the treatment zone (or area of necrosis) can be visualized on ultrasound. As discussed, the gas created during DC ablation diffuses through tissue being treated until it becomes absorbed in solution with the fluids present in the tissue. By controlling the rate of therapy (current) and the total therapy delivered, the region of gas bubbles in the tissue can be correlated to the area of necrosis. Such visualization may be used, for example, when DC ablation is used to treat benign and malignant tumors.

In some embodiments, one anode and one cathode is provided per current source. This may facilitate control of the treatment zone size. In other embodiments, more than one anode and one cathode are provided per current source. This may reduce the likelihood of poor tissue contact during treatment. If more than 2 electrodes are used per current source, current may be directed to specific electrodes of the same polarity by making some electrodes have higher (or lower) impedance than others. This may be accomplished by varying configurations of the electrodes, for example by creating different surface textures on different electrodes, by providing a means for venting gases via some electrodes but not others, etc.

In various embodiments, size of treatment zone may be customized for specific treatment positions of the electrodes. For example, in treatment of BPH, smaller treatment zones may be formed near the prostate base and apex and larger zones may be formed in bulkier areas. Such varied treatment zone sizes may be provided by using different electrode sizes, differing numbers of electrodes, differing current or charge delivery, or by varying other process or system parameters. For example, shorter electrodes may be used at the distal and proximal ends and longer electrodes may be used in the middle band(s), as shown in the embodiment of FIG. 4c. In an alternative embodiment, fewer electrodes can be used at distal and proximal ends and more electrodes in the middle band(s). In a further embodiment, less charge may be delivered to electrodes at distal and proximal ends and more charge may be delivered to electrodes in middle band(s). In yet a further embodiment, the electrodes at distal and proximal ends may be programmed as anodes and those in the middle band(s) as cathodes.

DC current ablates tissue by imparting extreme pH (<5 or >9 to 10) into the tissue surrounding the electrode. The area surrounding the electrode affected by the extreme pH is referred to as the treatment zone. In some embodiments, the system may be deployed to provide overlapping polarity treatment zones. Such overlapping may optimize the radius of the treatment zone for tissue ablation. When DC ablation electrodes are placed in close proximity, the extreme pH zones grow. When they overlap for a paired electrode, the zones increase in radius more readily than when separate for a given dose.

Figure 11:
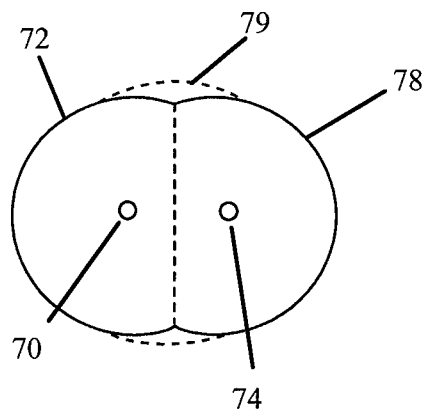
FIG. 11 illustrates overlapping treatment zones, in accordance with one embodiment.

FIG. 11 illustrates a radius of a combined treatment zone at the pH interface. The treatment zone may increase approximately 10-20% in radius. Specifically, FIG. 11 illustrates a first electrode 70 with a first pH extreme 72, a second electrode 74 with a second pH extreme 76, and a typical treatment radius 78. FIG. 11 further illustrates the increased radius 79 of the combined treatment zone (shown by the dotted line).

Similarly, in other embodiments, the anode and cathode may be placed proximate one another. By placing the anode and cathode (opposite polarity electrodes) in close proximity to one another, extreme pHs can be achieved to necrose tissue. The opposite pH levels help to neutralize one another to decrease the amount of time it takes for the surrounding tissue to return to normal conditions.

Figure 12:
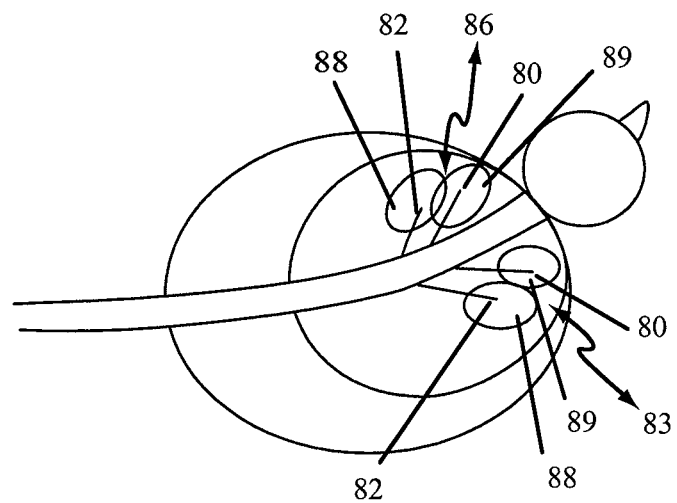
FIG. 12 illustrates electrodes placed in close proximity, in accordance with one embodiment.

FIG. 12 illustrates an embodiment with two anodes 80 and two cathodes 82. In one treatment area 83, an anode 80 is placed proximate a cathode 82, for example spaced between approximately 2 and approximately 20 mm from one another. The same set up is provided in a second treatment area 86—an anode 80 placed proximate a cathode 82. As a result, in each treatment area 83 and 86, a high pH zone 88 and a low pH zone 89 each arise proximate to the other. The zones 88 and 89 likely overlap one another. In the area of zone overlap, the pH of the tissue can return to normal within, for example, hours of the DC ablation procedure.

Figure 13A:
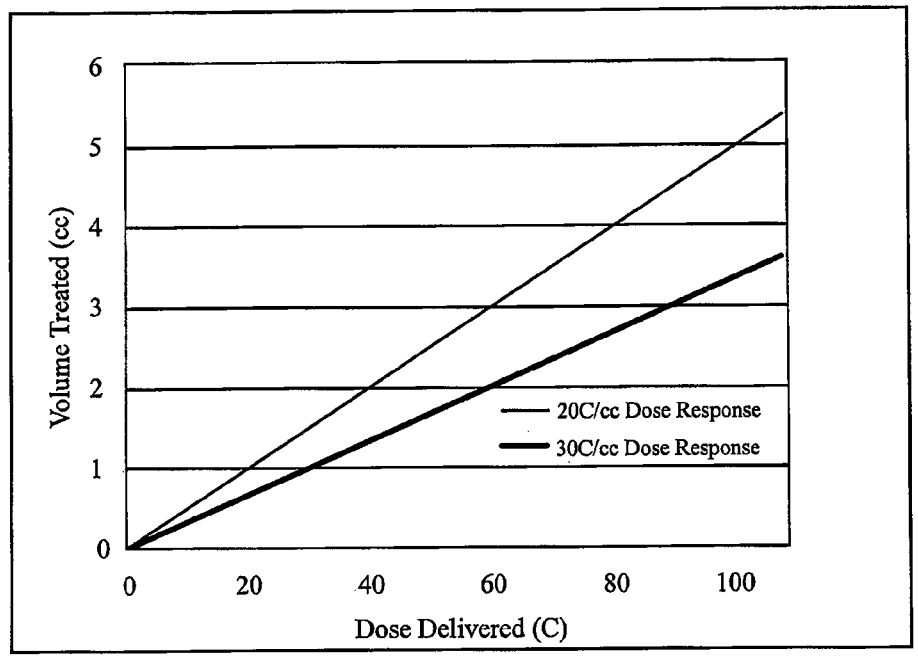
FIG. 13a illustrates dose delivered versus volume of tissue treated, in accordance with one embodiment.
Figure 13B:
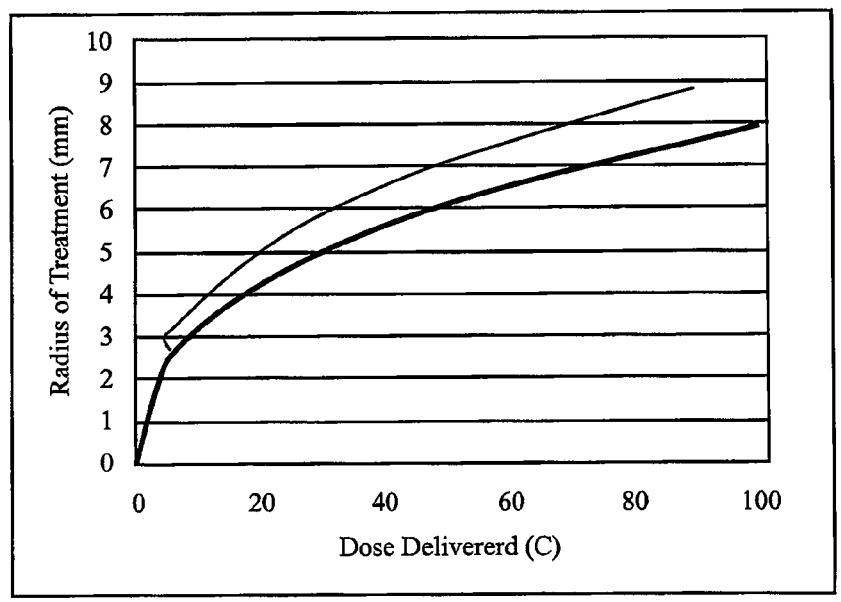
FIG. 13b illustrates dose delivered versus expected radius of treatment for a 6 mm electrode in prostatic tissue, in accordance with one embodiment.
Figure 13C:
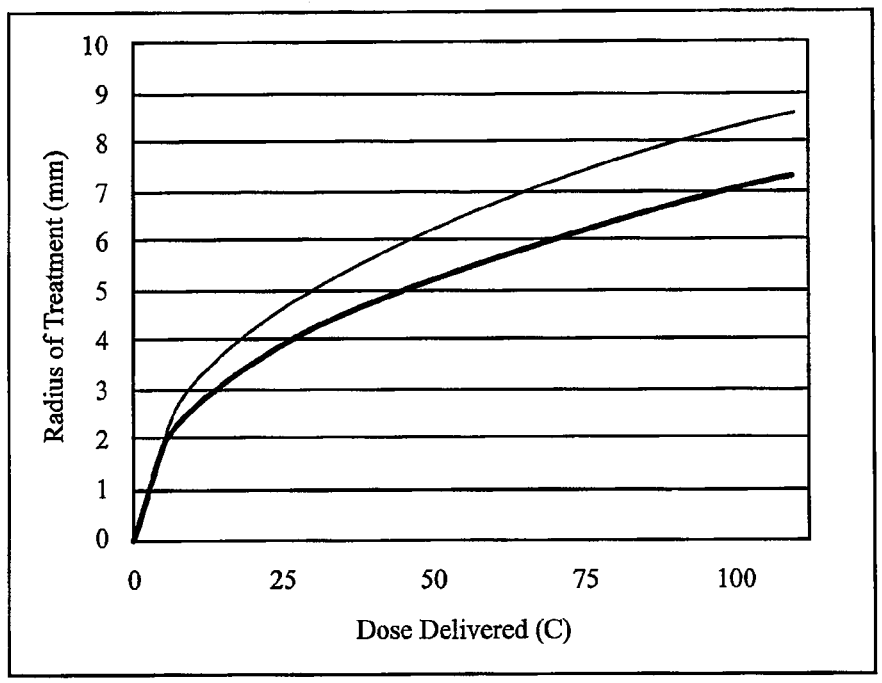
FIG. 13c illustrates dose delivered versus expected radius of treatment for 12 mm electrode in prostatic tissue, in accordance with one embodiment.
Figure 13D:
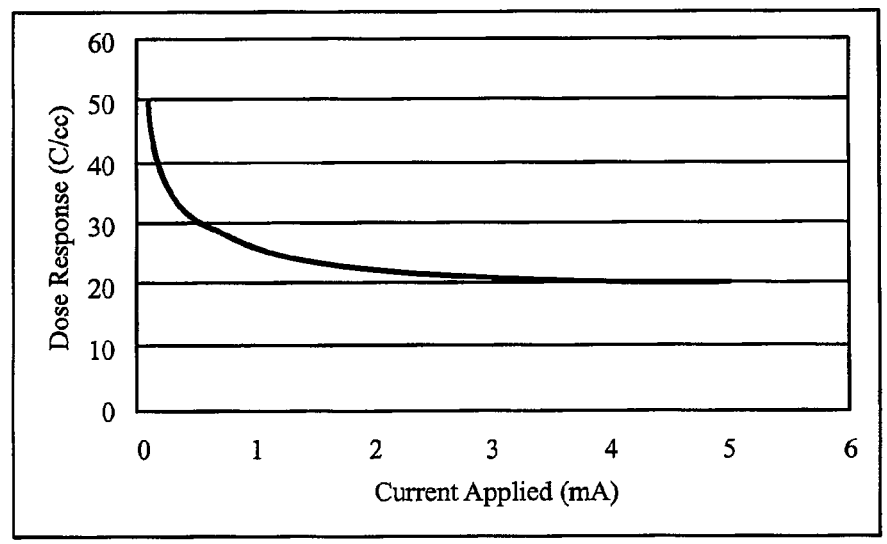
FIG. 13d illustrates current applied versus dose response, in accordance with one embodiment.

FIGS. 13a through 13d illustrate various effects and relationships of dosage. FIG. 13a illustrates the dose delivered versus the volume of tissue treated. FIG. 13b illustrates the dose delivered versus the upper and lower limit of expected radius of treatment for a 96 mm electrode in prostatic tissue. FIG. 13c illustrates the dose delivered versus the upper and lower limit of expected radius of treatment for a 12 mm electrode in prostatic tissue. FIG. 13d illustrates current applied versus dose response.

Generally, DC ablation creates necrosis around a singular anode and a singular cathode at a rate of approximately 0.07-0.05 cc/C at the anode and at a rate of approximately 0.10-0.08 cc/C at the cathode. A typical period for treating BPH using systems and methods for DC ablation as disclosed herein is under 30 minutes. Dosing at approximately 25 mA for approximately 30 minutes will deliver 45 C. This in turn treats between approximately 5.8 cc and approximately 7.7 cc of tissue per pair of electrodes. To achieve a more efficacious treatment, multiple electrode pairs may be used. In some embodiments, 2 to 6 pairs of electrodes may be used. This correlates to approximately 11.6 to approximately 14.4 cc of treated tissue for 2 pairs of electrodes and between approximately 34.8 and approximately 43.3 cc of treated tissue for 6 pairs of electrodes. These numbers do not account for the overlap of treatment zones which decrease the amount of treated tissue. In some embodiments, the treatment zones overlap. Treatment times may vary between 15 and 45 minutes depending on the dosing required and rate at which the treatment is delivered. Alternatively fewer pairs of electrodes could be used in a device to achieve these same larger treatment zones if the catheter or electrodes are repositioned between treatments.

The rate at which the charge is applied (current, units of milliamperes) does not affect the ultimate radius of the treatment zone as long as the current provides more charge than the tissue's natural ability to stabilize its own pH. The relationship between current applied and the dose response is shown FIG. 13d. As shown, in some embodiments, it may be desirable for the treatment current to be at or above approximately 1mA. In the example of FIG. 13d, all currents above 5 mA exhibit generally the same dose response. While higher currents may not increase dose response, higher currents may reduce treatment time to deliver the desired dosage. The higher current, however, may increase likelihood of patient discomfort. Generally, as current decreases, patient discomfort and muscle contractions (or muscle twitch) decrease. In some embodiments, the dose may be delivered at a constant current to prevent nerves in the region of treatment from being stimulated and causing muscle contraction. The magnitude of current delivered may be adjusted during treatment to allow pain and treatment time to be minimized. Care should be taken however, because a fast rate of current change may cause patient discomfort and muscle twitch. Thus, in some embodiments, it may be advisable that any change in the current delivered be done at a rate no greater than 10 mA/s to prevent muscle contraction and patient discomfort. A suitable rate of change is approximately 1 mA/s.

Figure 14:
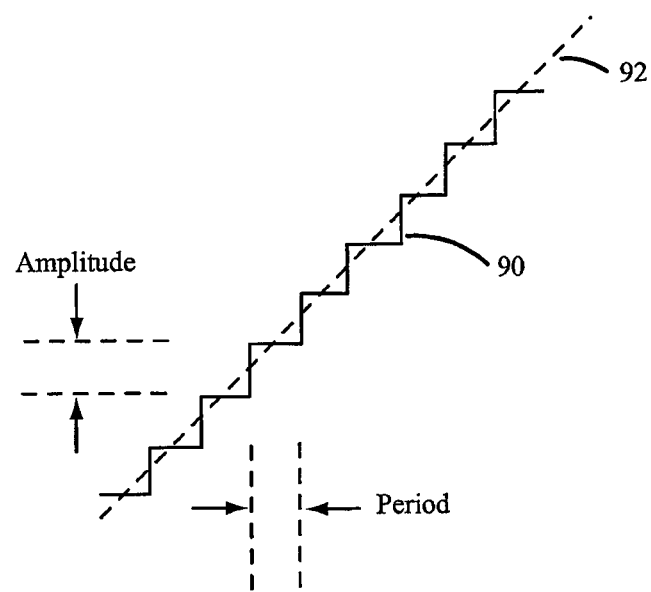
FIG. 14 illustrates and defines the period and amplitude of current ramping during the start of treatment, in accordance with one embodiment.

FIG. 14 illustrates current 90 increased gradually when current delivery is started to prevent the stimulation of nerves. Current 90 is also decreased gradually when current delivery is terminated. The increase or decrease may occur in steps of amplitude and period with the ramp rate equal to the step amplitude divided by the step period. The upper limit on the amplitude for preventing nerve stimulation is 0.5 mA for increasing current. A suitable embodiment is approximately 0.2 mA for increasing the current. The upper limit on the amplitude for preventing nerve stimulation is 1 mA for decreasing current. A suitable embodiment is approximately 0.5 mA for decreasing the current. Regardless of the slowness of the period of the steps, a large enough amplitude step will cause nerve stimulation. For amplitudes below that limit, there is a minimum limit on the period for preventing nerve stimulation. Small amplitude steps can still cause nerve stimulation if the steps occur too quickly and result in a ramp rate greater than 10 mA/s. The ramp rate (slope of broken line 92) should ideally be as great as possible without resulting in a high risk of nerve stimulation. If the step amplitudes are low enough, capacitance in the circuit may cause the output to look less like steps and more like a straight line (such as broken line 92), which may help to reduce the risk of nerve stimulation. These observations also apply to ramping down the current.

In some embodiments, an independent current source may be used to deliver the current for each electrode pair in order to control the charge passing through each electrode and thus the size of the treatment zone. Changing impedances at individual electrodes throughout the therapy session may lead to an unpredictable imbalance in treatment zones if multiple cathodes and anodes are put on a single current source. If multiple electrode pairs are placed on a single current source, the treatment zones may be controlled by putting a coulomb counter on each electrode and directing the desired amount of charge to each electrode.

The acidic and basic zones are created by the following chemical reaction:

Anode Reactions: 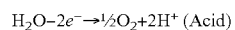

$$H_2O - 2e^- \rightarrow \tfrac{1}{2}O_2 + 2H^+ \text{ (Acid)}$$

Cathode Reaction: 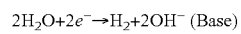

$$2H_2O + 2e^- \rightarrow H_2 + 2OH^- \text{ (Base)}$$

The anode reactions also include a chlorine reaction that produces molecular chlorine. The molecular chlorine reacts with water to form hypochlorous acid, chloride and hydrogen ions. These reactions occur within both benign and malignant tissue including prostate. A marker, such as an ultrasound marker, may be provided to indicate pH in real time during treatment.

The anode and cathode reactions create cell necrosis within the treatment zone. The cathode causes necrosis via a combination of liquefaction cell necrosis and coagulation cell necrosis. The anode causes necrosis via coagulation cell necrosis. Cell necrosis occurs in normal prostate tissue, hyperplastic prostate tissue, and malignant prostate tissue. Accordingly, dosage and configuration may be optimized to generally limit the treatment area to the hyperplastic prostate tissue.

Figure 15A:
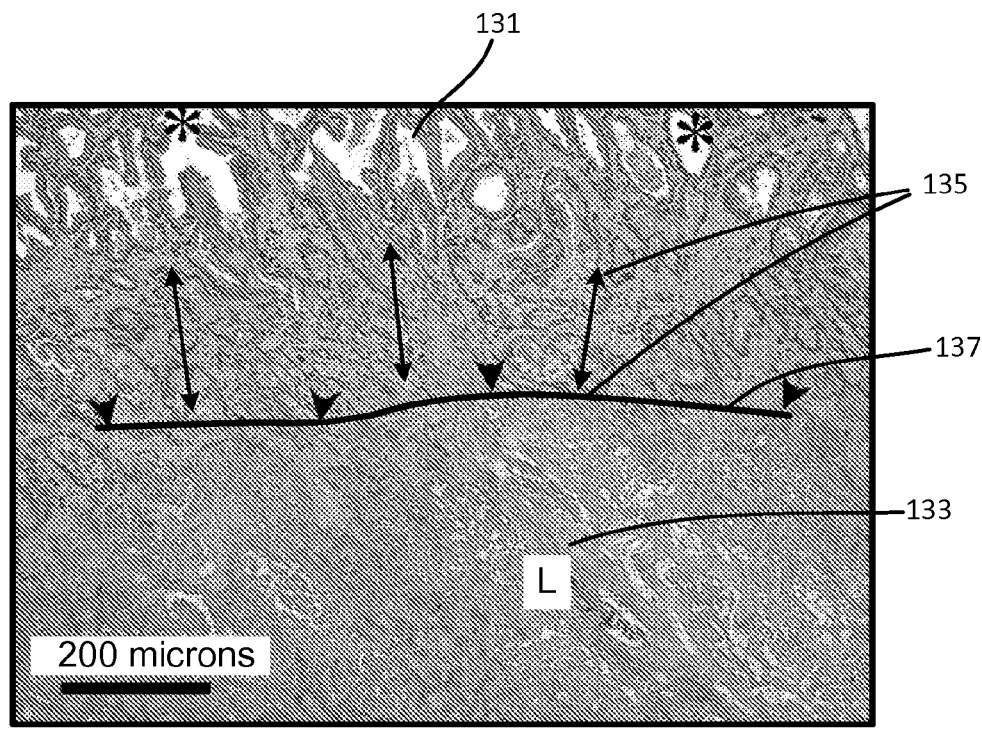
FIG. 15a is an in vivo image illustrating a liquefaction necrosis histology at the boundary of a cathode treatment zone.
Figure 15B:
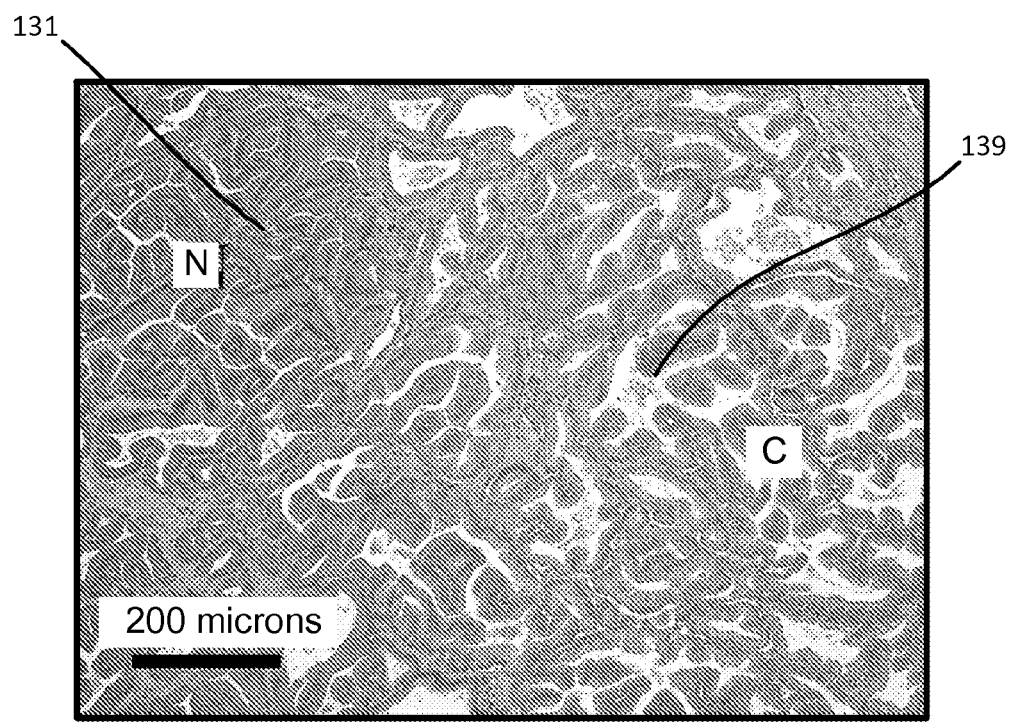
FIG. 15b is an in vivo image illustrating a coagulation necrosis histology at the boundary of an anode treatment zone.

FIGS. 15a and 15b illustrate images of necrosis within necrotic prostate tissue caused by DC ablation at a cathode and an anode. FIG. 15a illustrates a liquefaction necrosis histology at the boundary of a cathode treatment zone. Normal tissue is shown at 131 and liquefaction necrosis is shown at 133. As shown, a transition zone exists at 135 with a liquefaction necrosis boundary 137 being formed. FIG. 15b illustrates a coagulation necrosis histology at the boundary of an anode treatment zone. Specifically, normal tissue is shown at 131 and coagulation necrosis is shown at 139.

Liquefaction necrosis and coagulation necrosis create a change in the structure in the prostate as the affected tissues become fibrous and are absorbed into the body through its natural healing process. This thus causes removal of cellular mass, leaving a void. Because the treatment zone is predictable, the void is predictable. By removing cellular mass within the prostate, the interior of the prostate is debulked and excess pressure placed on the prostatic urethra is reduced. This reduction in pressure on the urethra reduces or eliminates BPH symptoms, sometimes referred to as Lower Urinary Tract Symptoms (LUTS). It is an advantage of DC ablation over other techniques that the outer wall of the prostate is more resistant to damage caused by the electrochemical reaction than is inner prostate tissue. Hence, a set of electrodes not perforating the outer wall but close to the wall destroys the desired prostate tissue inside the boundary formed by the wall and not the wall itself. The outer boundary generally appears to be more chemically robust as well as providing a mechanical boundary. Thus, while thermal energy does not respect the tissue plane, DC ablation does.

In some embodiments, the electrodes may be withdrawn, the catheter repositioned, and the electrodes redeployed to cover the desired treatment zones. In other embodiments, the number of electrodes provided is sufficient to provide treatment without redeployment of the system.

Once the reactions leading to cell necrosis have begun, the electrodes may be withdrawn and the catheter is withdrawn. In some embodiments, the electrodes are withdrawn into the catheter and the catheter is withdrawn. Withdrawing the electrodes into the catheter may comprise release of a trigger or slide in the handle, may comprise collapsing the electrodes by sliding a sheath over the electrodes, or may be done in other suitable manner. In some embodiments, the electrodes and the catheter are withdrawn simultaneously.

The liquefaction and softening of treated tissue around the cathode results at least from elevated pH; elevated pH causes necrosis and cell lysis. Rupture of the cell wall causes the rigid pathologic tissue to soften, relieving symptoms of BPH related to excess compression of the urethra. This effect can be employed to advantage in the removal of electrodes. Changing the polarization of each electrode to cathodic at some time during treatment will soften the area and allow easier removal of the electrode. Likewise, inserting the electrodes may be eased by making each one cathodic during the insertion. If tenting of the urethra is evident during insertion, causing each electrode to be cathodic at that time can soften the urethra at the electrode tip sufficiently to allow easier penetration without significant additional damage to the urethra For example, with some physiologies it may be difficult to penetrate lumens, such as the urethra, and tissue with a fine electrode. Chemical drilling may be used to aid in tissue penetration. More specifically, DC ablation may be used to help penetrate the tissue. In some embodiments, all of the electrodes may be negative or cathodic to aid in tissue penetration, This takes advantage of the inherent electro-osmosis of DC ablation where fluids are drawn to the cathodes and the tissue becomes edemic. The gelatinous tissue so treated is more easily penetrated. Thus, in some embodiments, the electrode may be activated when first contacted with the tissue but before advancement into the tissue. The electrodes may be advanced during pre-treatment or pre-treatment may be done for a short period of time, for example approximately 30 seconds, and the electrodes then advanced.

Figure 16:
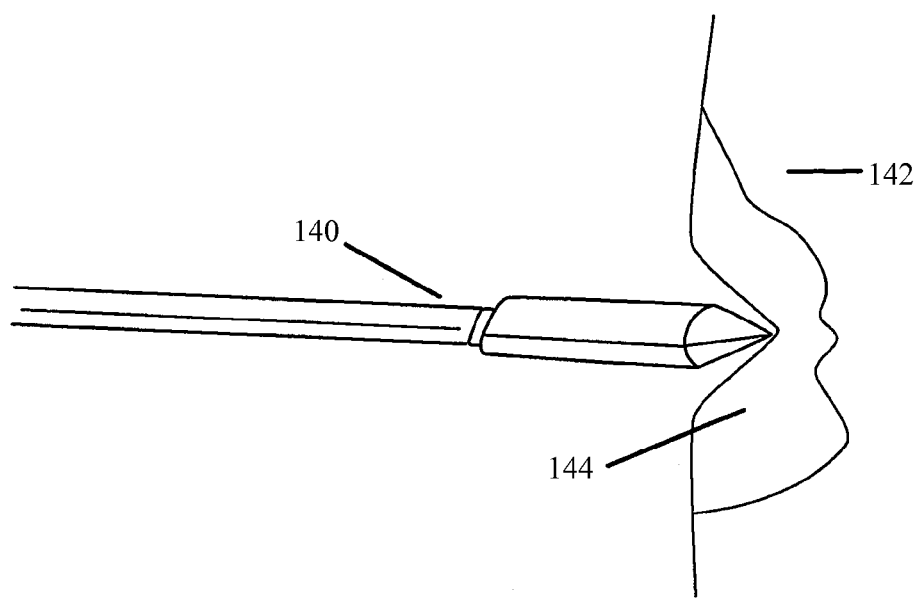
FIG. 16 illustrates a view of electrode deployment into pretreated tissue

FIG. 16 illustrates a view of electrode deployment into pretreated tissue. As shown, the tissue 142 includes a pretreated region 144 that is substantially gelatinous. The electrode 140 is able to more easily penetrate the tissue 142 in the gelatinous region 144.

Figure 17A:
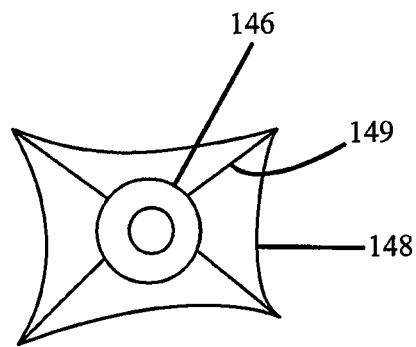
FIG. 17a illustrates a system for tissue treatment including a catheter and electrodes with the electrodes deployed without vacuum, in accordance with one embodiment.
Figure 17B:
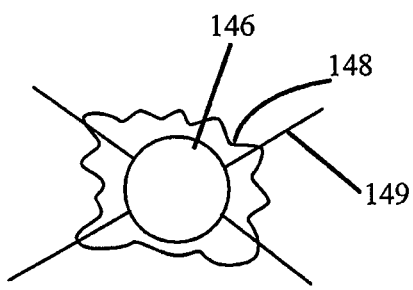
FIG. 17b illustrates a system for tissue treatment including a catheter and electrodes with the electrodes deployed with vacuum, in accordance with one embodiment.

FIGS. 17a and 17b illustrate a further embodiment to facilitate electrode penetration. In another embodiment of urethral preparation, a vacuum may be used to put the urethra in direct and firm contact with the catheter of a system for treating tissue as provided herein. Direct and firm contact of the urethra with the catheter facilitates piercing of the urethra by electrodes. With some physiologies, the urethra may have a larger cross section than the catheter placed therein. This increases column strength requirements for the catheter and makes it more difficult for the electrodes to pierce the catheter. For example, the urethra may expand and not be penetrated by the electrodes or the electrodes may buckle against the urethra. FIGS. 17a and 17b illustrate a system for tissue treatment including a catheter 146 and electrodes 149. The figures illustrate an end view with the system deployed through the urethra 148. FIG. 17a illustrates electrodes 149 deployed (without vacuum) and causing expansion of the urethra 148. As shown in FIG. 17b, by drawing the urethra 148 firmly against the catheter 146, for example by vacuum force, the electrodes 149 more easily penetrate the urethra 148. Thus, the electrodes 149 may be deployed relatively immediately after drawing of the urethra 148 against the catheter 146. FIG. 17b illustrates electrodes 149 penetrating the urethra 148, with the urethra 148 vacuumed to the catheter 146.

Figure 18:
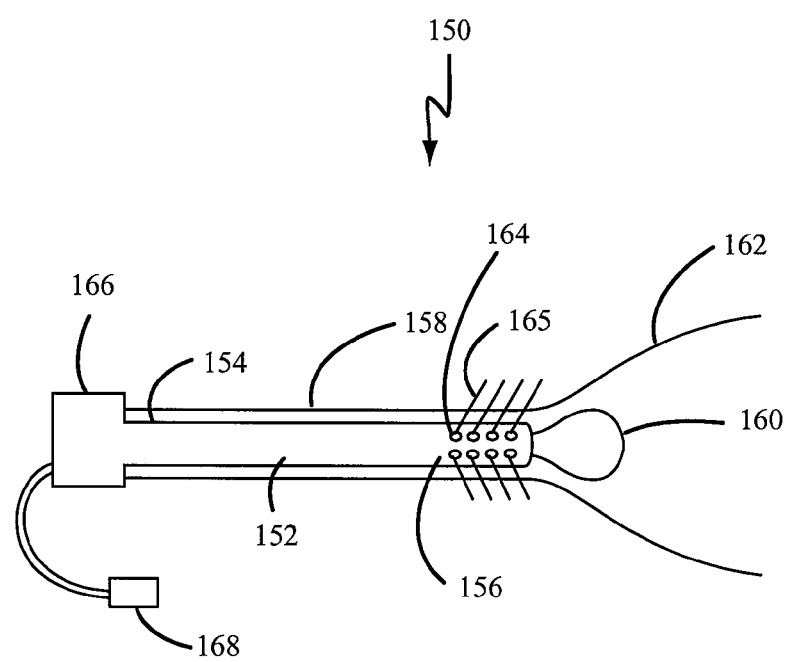
FIG. 18 illustrates an embodiment of a system for treating tissue including vacuum ports at the electrode holes, in accordance with one embodiment.

FIG. 18 illustrates an embodiment of a system for treating tissue including vacuum ports at the electrode holes. As shown, the system 150 includes a catheter 152 having a proximal end 154 and a distal end 156. As shown, the catheter 152 is configured to extend through the urethra 158. A balloon or other fixation element 160 is provided at the distal end 156 of the catheter 152 and is shown deployed in the bladder 162. A plurality of electrode holes 164 are provided at a distal portion, near the distal end 156, of the catheter 152. The electrode holes 164 operate for facilitating deployment of electrodes 165 from the catheter 152 and also operate as vacuum ports. A vacuum connector 166 and an electrical connector 168 are provided at the proximal end 154 of the catheter 152. The vacuum connector 166 may couple to a syringe or other means for achieving a vacuum. Drawing a vacuum before electrode penetration may facilitate use of smaller electrodes. In some embodiments, the system shown in FIG. 18 may be used for saline injection and vacuum. More specifically, the electrode holes/vacuum ports may be used to create a vacuum and also to distribute saline. Thus, in one embodiment, vacuum is achieved during penetration of the electrodes and is followed by saline injection for buffering during treatment.

As can be appreciated from the chemical reactions occurring at the electrodes, gases may be generated by DC ablation. More specifically, during DC ablation of soft tissue, ions are created at the anode and cathode electrodes when current passes through the electrodes. In order for the current to pass, the impedance generally is stable and less than about 5 kΩ to prevent operating at high voltages. DC ablation creates hydrogen and oxygen gas during the hydrolysis process. These gases can cause the impedance from the electrode to the tissue to spike greater than about 5 kΩ. This happens when the gas is allowed to build up around the electrode without either diffusing into the tissue, being vented away from the treatment area, or going into solution in fluid around the treatment zone. Typical impedance ranges within the prostate are between approximately 300 and 500 ohms when treating with a current of greater than approximately 5 mA.

The amount of current delivered affects the amount of gas created. The rate at which gas is created is directly proportional to the current at which it is delivered. For soft tissue applications such as the prostate, DC ablation generally may be delivered between approximately 10 mA and approximately 50 mA. Generally, at currents higher than 50 mA, gas created by the treatment may not have sufficient time to dissolve, diffuse, or vent. 75 to 100 mA may be used to decrease treatment time if-gas is able to sufficiently vent. Conversely, at currents lower than 10 mA, the body's buffering may reduce effectiveness of the treatment. In one embodiment, current level is between approximately 25 mA and 40 mA.

Generally, the amount of gas generated by treatment is determined by dosing. The amount of gas generated typically increases as current increases. In various embodiments, the system may be provided with mechanisms for venting the gases generated. Means for venting the gases may be provided within the electrodes, within the catheter, or other. Accordingly, the method for BPH treatment may further comprise venting gases created during treatment. Removal of the gases may lower the impedance and impedance fluctuations seen by the electrodes, thereby permitting continued treatment in the desired range of current and voltage.

Figure 19A:
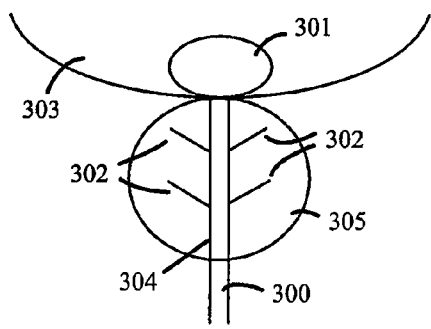
FIG. 19a illustrates balloon deployment in a bladder, in accordance with one embodiment.
Figure 19B:
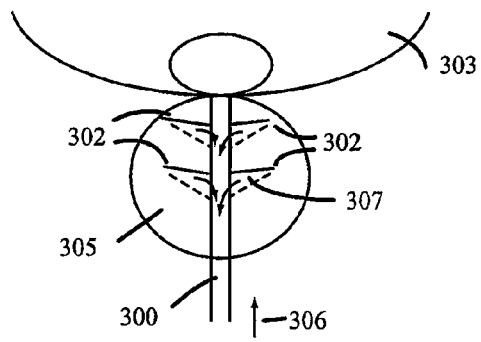
FIG. 19b illustrates catheter deployment while applying force towards a bladder, in accordance with one embodiment.
Figure 19C:
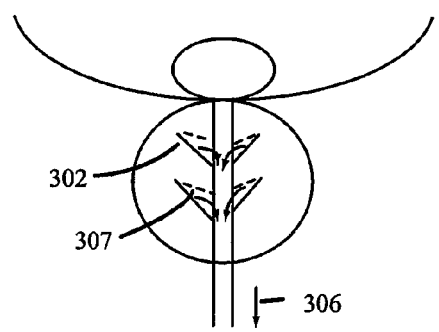
FIG. 19c illustrates catheter deployment while applying force away from the bladder in accordance with one embodiment.

A first embodiment of a mechanism for venting gases is shown in FIGS. 19a-19c. FIGS. 19a-19c illustrate relevant anatomy to BPH treatment including the bladder 303, urethra 304, and prostate 305. FIGS. 19a-19c further illustrate a catheter 300, balloon 301, electrodes 302, and gaps 307. As shown in FIG. 19a, the balloon 301 is located in the bladder 303 and inflated. The electrodes 302, having punctured the urethra 304, reside within prostate 305 either prior to or after applying current for DC ablation. In FIG. 19b, the catheter 300 has been pushed forward with force 306 towards the bladder 303 prior to applying current but after deploying electrodes 302. Force 306 holds the electrodes 302 in the position shown in FIG. 19b. This creates gaps 307 in the prostate 305 between the original electrode position of FIG. 19a and the new position of FIG. 19b. The gaps 307 serve to provide a path for the gases generated during DC ablation to escape. In an alternative embodiment, shown in FIG. 19c, the catheter 300 may be pulled away from the bladder 303 after deploying the electrodes 302.

Figure 20A:
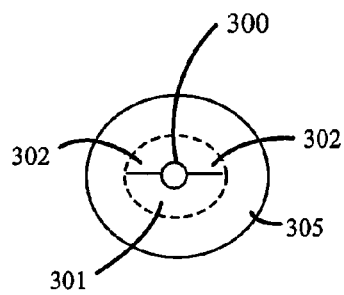
FIG. 20a illustrates electrode deployment in a prostate, in accordance with one embodiment.
Figure 20B:
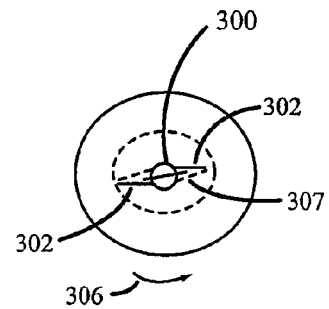
FIG. 20b illustrates catheter rotation for movement of electrodes, in accordance with one embodiment.

A second embodiment of a mechanism for venting gas is shown in FIGS. 20a and 20b. In yet another embodiment, the electrodes 302 may be rotated following deployment, as shown in FIGS. 20a and 20b. In FIG. 20a, electrodes 302 are shown deployed in prostate 305. The broken line represents the balloon 301. In FIG. 20b, the catheter 300 has been rotated by force 306, causing the electrodes 302 to assume a new position and opening up gaps 307 through which the gases may escape. In alternative embodiments, other means for removing gases may be used. For example, gas may be vented by having a negative pressure in the delivery system or catheter to effectively vacuum gas away from the active electrode(s).

Figure 21A:
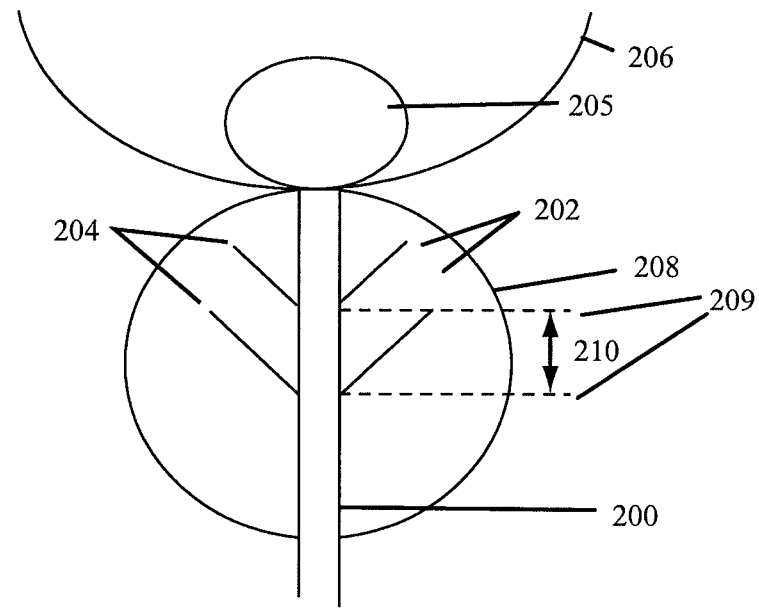
FIG. 21a illustrates a coronal view of a system comprising two axial planes of four electrodes each, in accordance with one embodiment.
Figure 21B:
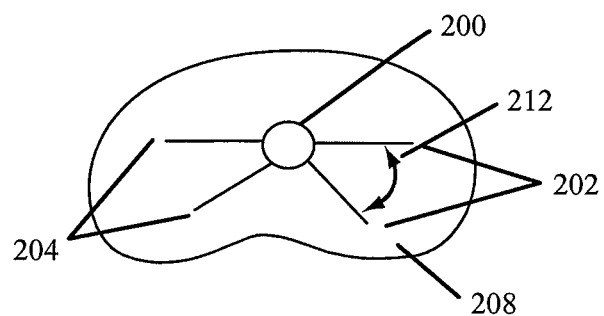
FIG. 21b illustrates a transverse view of a system comprising four electrodes in each axial plane, in accordance with one embodiment.

FIGS. 21a and 21b illustrate an embodiment comprising two axial planes of four electrodes and illustrate the axial electrode spacing and angular separation. FIG. 21a is a coronal or top view and FIG. 21b is a transverse or end view. The system is shown including a catheter 200, a plurality of electrodes including two electrodes 202 on one side of the catheter 200 and two electrodes 204 on the other side of the catheter 200, and a fixation element 205. The catheter 200 is deployed transurethrally and the fixation element 205 positioned in the bladder 206 such that deployment of the electrodes 202 is into the prostate 208. As shown in FIG. 21a, an axial spacing 210, comprising the distance between the electrodes 202 or 204 on each side of the catheter 200, is provided between the electrodes 202 or 204. Dashed lines 209 indicate the longitudinal position of the electrodes 202 relative to the catheter 200. As shown in FIG. 21b, an angular spacing 212, comprising the distance between the electrodes 202 or 204 on each side of the catheter 200, is provided between the electrodes 202 or 204. The angular spacing is the angle between the posterior and anterior electrode on each side of the catheter.

Providing multiple electrodes to an area to be ablated can reduce the number of coulombs or the dose required from each electrode, thus decreasing the amount of gas created at each electrode. In some embodiments, no single electrode delivers more than approximately 72 coulombs. In one embodiment, each electrode delivers between approximately 24 and 48 coulombs of charge with an axial electrode spacing (measured down the catheter) of approximately 8 to 10 mm and an angular separation of between approximately 15 to 65 degrees. A suitable angular spacing is approximately 30 to 45 degrees with 35 degrees being optimal in certain embodiments. The axial spacing could be increased to 12 to 16 mm and up 20 mm if the dosing is increased. The axial separation could be reduced to 4 to 6 mm if dose per electrode is reduced and the number of electrodes is increased.

During treatment, the electrodes may lose ohmic contact with different types of tissues, thereby making it difficult to deliver the desired current. When contact is lost, it can cause the treatment zone to become more unpredictable and muscle contractions can occur due to spikes in voltage and current. Loss of contact may take place for multiple reasons including, at least:

1) Hydrogen gas created from the cathode reaction or oxygen gas from the anode reaction may saturate the electrode surface and cause an increase of impedance;
2) Chlorine gas created from the anode reaction may saturate electrode surface and cause an increase of impedance; and
3) The reaction at the anode may cause local dehydration and cause the tissue proximate to the electrode to lose its conductive properties.

In some embodiments, actions may be taken to prevent an increase in impedance or to counteract an increase in impedance arising at least from these sources. In one embodiment, a positive force may be added to the tissue using the active portion of the electrode, by the shape of the electrode design, or by using an array of electrodes and sequencing the therapy to allow natural diffusion within prostatic tissue to overcome the increase of impedance at the electrode site. Force to the electrode can be accomplished by adding a torque, an axial load down the electrode, or an axial load down the catheter.

Figure 22A:
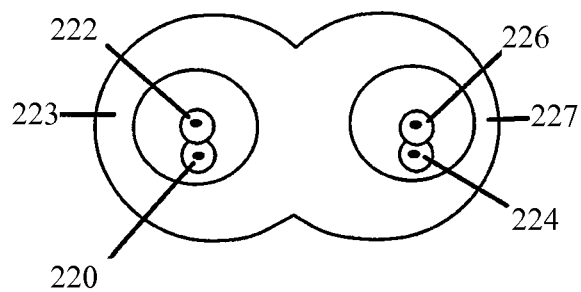
FIG. 22a illustrates two cathodes in parallel and two anodes in parallel and the associated treatment zones with moderate resistance, in accordance with one embodiment.
Figure 22B:
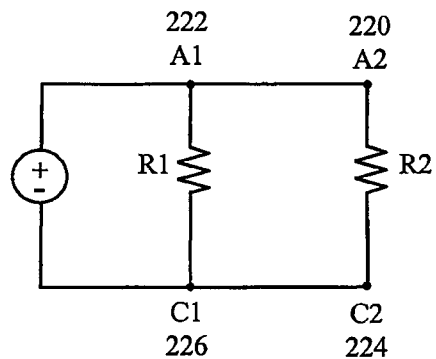
Figure 22C:
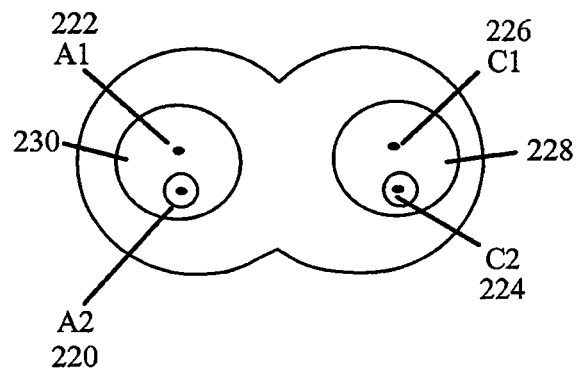
FIG. 22c illustrates treatment zones with high resistance, in accordance with one embodiment.

In another embodiment, an array of electrodes may be used including either or both of multiple cathodes and anodes in parallel with each other to deliver the therapy. For example, as shown in FIGS. 22a and 22c, multiple anodes and multiple cathodes may be provided in parallel. FIG. 22a illustrates a first anode 222, a second anode 220, a first cathode 226, and a second cathode 224. FIG. 22a further illustrates the treatment areas 223 and 227 associated with the anodes 222, 220 and the cathodes 226, 224, respectively. Generally, each electrode of an anode pair or cathode pair may be at approximately the same potential and be placed in close proximity. Providing electrodes in parallel and in close proximity can ensure continued treatment even if one electrode loses contact. More specifically, if one anode (or cathode) of an anode (or cathode) pair loses contact, the area will continue to be treated by the other anode (or cathode) in parallel. This is true whether the electrode pair is an anode pair or a cathode pair. FIG. 22a illustrates a pair of anodes 220 and 222 in parallel and a pair of cathodes 224 and 226 in parallel. FIG. 22b illustrates an electric current diagram for FIG. 22a. FIG. 22c illustrates the effective treatment areas 230 and 228 resulting from R1 and R2, respectively, of FIG. 22b. As shown, the effective treatment areas 230 and 229, or area ablated, approximates the effective treatment areas 223 and 227 of FIG. 22a, where no impedance problems occur. While FIGS. 22a-22c illustrate two anodes and two cathodes, more than two electrodes may be put in parallel.

In one embodiment, the generator may be configured to monitor a measurement of impedance between the electrodes and uses a pattern of impedance measurements to predict a significant increase in impedance. Upon prediction of an increase in impedance, the generator reduces the current level or turns off the current, thereby preventing a current spike that could cause nerve stimulation.

Various current delivery mechanisms may be used to reduce the likelihood of stimulating nerves. In one embodiment, the generator utilizes a current source circuit with a high voltage compliance. Voltage compliance (or compliance voltage) is the maximum voltage a current source will go to in its attempt to source the programmed current. Compliance voltage values may be user settable, allowing user control over the sourcing and measurement process. If the generator voltage compliance is higher than the current level multiplied by the impedance, the current is controlled and current spikes are substantially prevented. For example, a voltage compliance of 200V allows the current source to deliver a current of 20 mA without current spike due to an impedance change of 10 kΩ.

The likelihood of sudden impedance changes can be reduced by using low current, such as less than or equal to about 30 mA. The low current substantially prevents the gas generation rate from greatly exceeding the rate that the gas escapes from and/or diffuses into tissue.

In another embodiment, to reduce the likelihood of sudden impedance changes and to complete treatment in a relatively short time frame, treatment may be started with a relatively high current, for example approximately 50 mA, and the current level may be reduced one or more times during the treatment, for example to a level less than about 20 mA. At the start of treatment, using the high current level, gas is generated at a high rate. Before enough gas accumulates to cause the electrode to lose contact with the tissue, the gas generation rate is decreased, by reducing current level, to better balance the gas generation and gas escape/diffusion rates.

In yet another, embodiment, a low level current (between approximately 1 mA and approximately 2 mA) can be applied for a short time (for example, less than about 5 minutes) before ramping up the current level. With the short delivery of a low level current, the area around the anode dehydrates and holds the anode in place. The forced contact between electrode and tissue may reduce impedance levels.

In a further embodiment, a low level current (between approximately 1 mA and approximately 2 mA) of opposite polarity from what will be used in the treatment may be applied for a short time (for example, less than about 5 minutes) before ramping up. The current may change the properties of the tissue around each electrode to reduce an impedance problem before ramping up the current.

System for Treatment

Returning now to FIG. 2b, FIG. 2b illustrates an embodiment of a system 10 for treating tissue with a transurethral catheter to create necrosis within the prostate. The system includes a catheter 14, electrodes 18, a mechanism 22 for deploying the electrodes, a fixation element 20, a mechanism 24 for deploying the fixation element, a generator 12, and an electrical connection 16 between the generator 12 and the catheter 14. The system 10 facilitates routing of the electrodes 18 into the prostate through the urethra. The system 10 makes electrical connections (isolated from fluids) to the power generator 12, thereby energizing the electrodes 18. The system 10 further facilitates longitudinal retraction of the electrodes 18 into the catheter 12 for atraumatic introduction and removal.

Figure 23A:
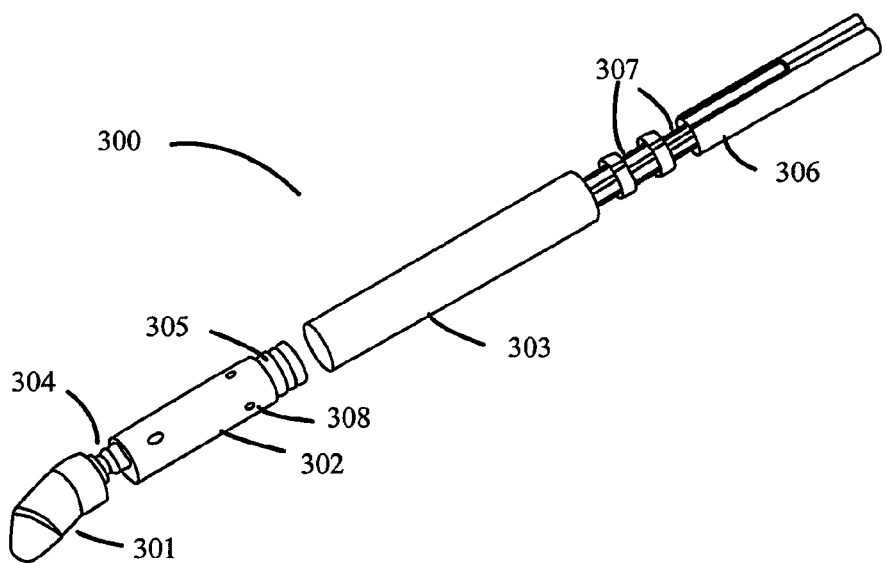
FIG. 23a illustrates an exploded view system for treating tissue, in accordance with one embodiment.
Figure 23B:
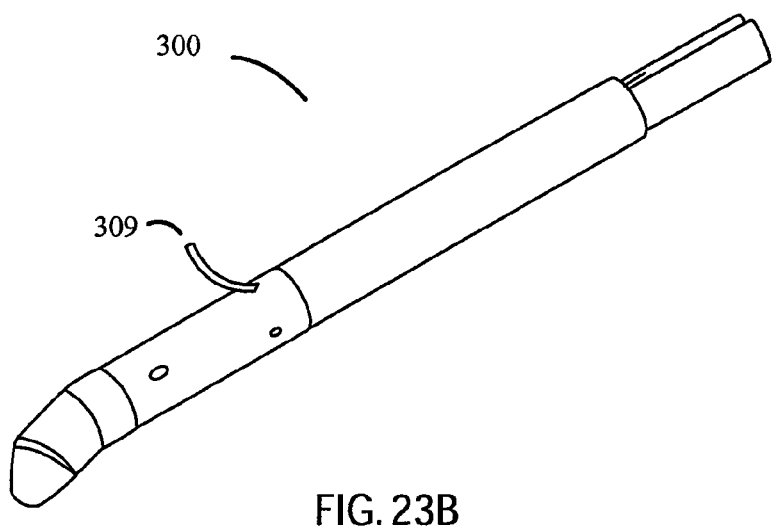

FIGS. 23a and 23b illustrate example embodiments of a catheter 300 for use with the system 10. FIG. 23a is an exploded view of a catheter body 300 comprising an outer body and an inner body. The catheter body outer body includes a tip 301, an electrode director 302, a sleeve 303, a first radiopaque marker 304, a second radiopaque marker 305, and routing holes 308. The catheter body inner body includes an actuator 306, connection channels 307, and a plurality of electrodes. As assembled, the system may be (other than at its proximal end) approximately 20 french or smaller. Each of the portions of the catheter body 300 may be manufactured from a different material or may be manufactured from the same material. FIG. 23b illustrates an assembled catheter body 300 with a deployed electrode 309.

The tip 301 is provided at a distal end of the outer portion of the catheter body 300. In the embodiment shown, the tip 301 is angled and provides atraumatic introduction and removal. In one embodiment, the tip 301 may be manufactured of a compliant material such as silicone, urethane, or PEEK. A plurality of straight electrodes are provided within the outer sleeve. The number of electrodes may vary from approximately 2 to approximately 12. Most physiologies may be treated with 4 to 8 electrodes. The plurality of straight electrodes are routed to and from the prostate through the electrode director 302. The electrodes may be semi-rigid: sufficiently flexible to extend through routing holes 308 in the outer sleeve 303 but sufficiently rigid to penetrate tissue. The electrodes may be corrosion resistant, such as by providing a corrosion-resistant layer over the electrodes. The electrode may comprise a nitinol wire with a corrosion resistant layer such as platinum or another noble metal.

The actuator 306 and associated electrodes may be provided within the inner portion of the catheter body 300. As may be appreciated by one skilled in the art, actuation may be linear or rotational and is based upon coupling of the electrodes to a portion of the catheter body and/or a handle. The electrodes may be coupled to the actuator 306 and may be corrosion resistant and sufficiently flexible to extend through the routing holes 308 and sufficiently rigid to penetrate tissue. The actuator 306 may be configured to move linearly along the length of the catheter. As previously discussed, the catheter body may include an inner body and an outer body; these may variously be referred to as the inner and outer body, the inner and outer sheaths, or the inner and outer sleeves. The inner body may include a plurality of crimped tubes for receiving the electrodes. These tubes are referred to as connection channels 307 and permit multiple straight electrodes to deploy with maximum column strength and to connect to flexible conductors in the inner body of the catheter. The electrodes are anchored in the inner body parallel to overlapping sleeves. Deployment of the electrodes may be affected via actuation of the inner actuator 306 in a distal direction with respect to the outer sleeve 303. The outer sleeve 303 directs the electrodes outwardly for treatment.

The electrode director 302 may have distal and proximal radiopaque or hyperechoic markings 304 and 305 to facilitate placement of the electrodes in a desired location. The markings 304 and 305 may be insulated to protect against exposure to the pH formed from the anode and cathode reactions, providing greater biostability. Such insulation may be provided by an outer sleeve of the catheter tip 301 and sleeve 303.

One or more anchoring features, described more fully with respect to other embodiments, may be provided to fix the system atraumatically in place for treatment. Generally, the anchoring features may comprise components that expand diametrically and lock in place when shortened to anchor the system within the urethra. Anchoring may provide linear and/or rotational stability to the system. First and second anchoring features may be provided, with the first being positioned distal of the treatment zone and the second being positioned proximal of the treatment zone.

Figure 24A:
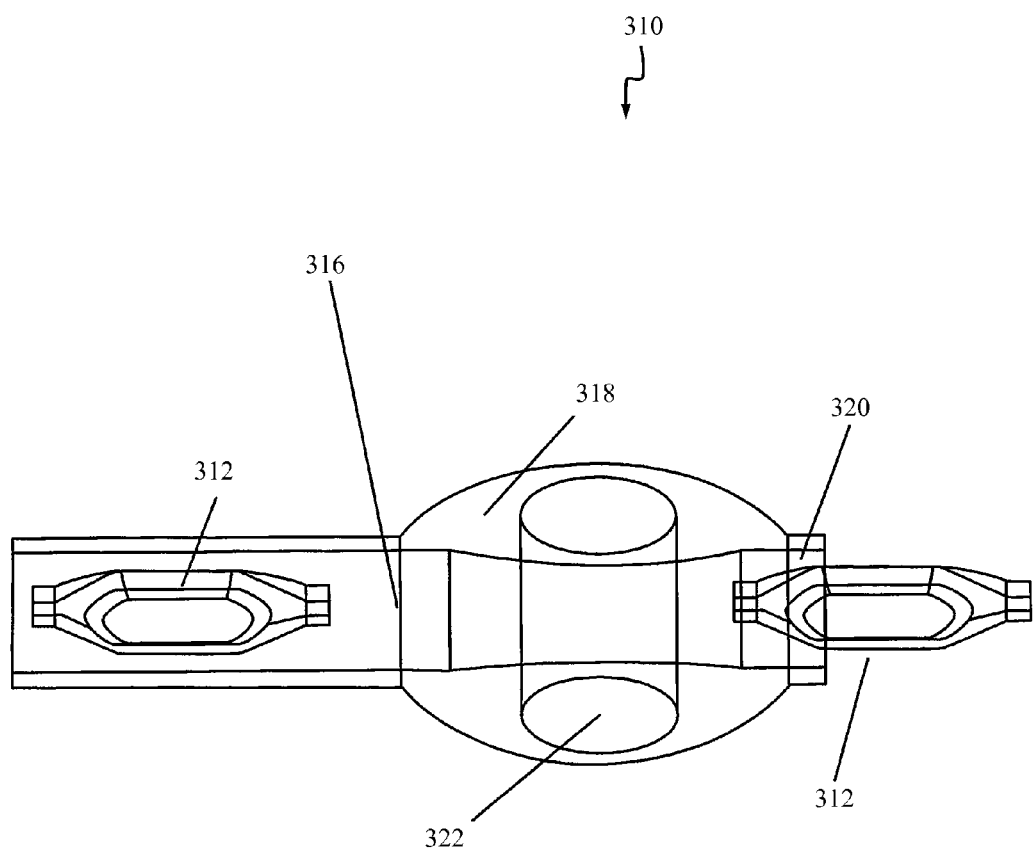
FIG. 24a illustrates a system for DC ablation with an elongated airless anchor in a collapsed configuration, in accordance with one embodiment.
Figure 24B:
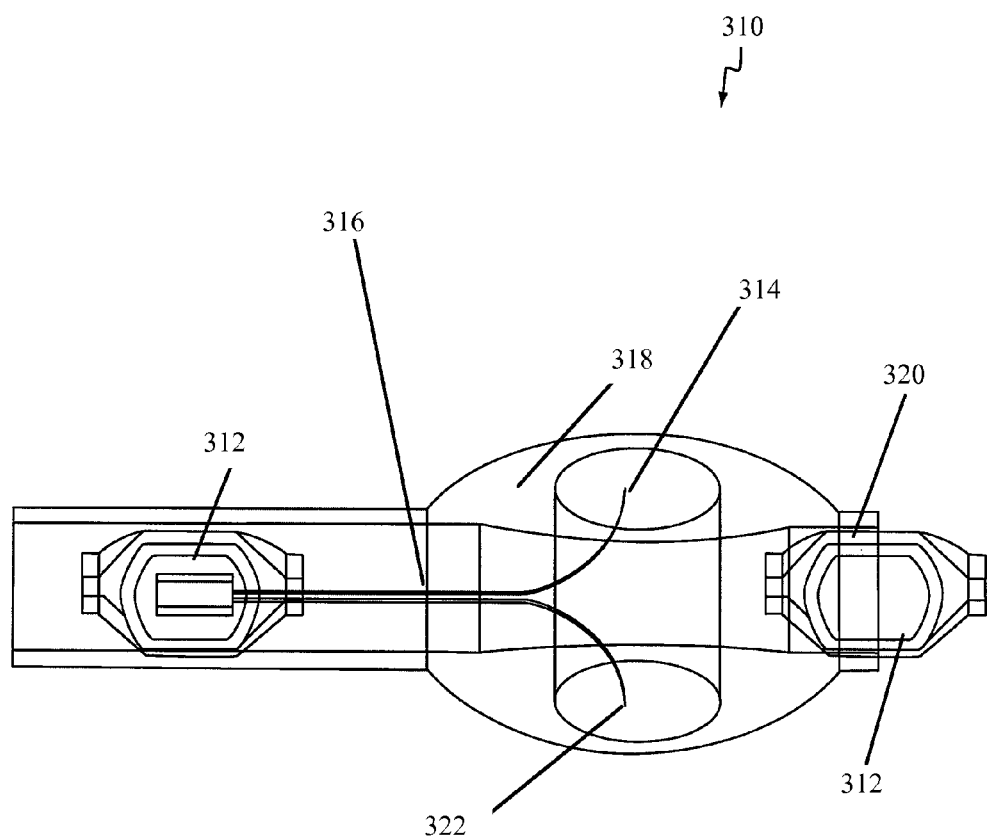
FIG. 24b illustrates a system for DC ablation with an elongated airless anchor in an expanded configuration, in accordance with one embodiment.

FIGS. 24a and 24b schematically illustrate a system 310 for non-thermal DC ablation placed for prostate treatment. The system 310 includes elongated airless anchors 312 and electrodes 314. The system 310 is deployed relative to the external sphincter 316, the prostate 318, and the bladderneck 320. FIGS. 24a and 24b further illustrate lateral lobe growth 322 in the prostate 318, leading to urethra compression 322. Such lateral lobe growth may be treated using the system 310. FIG. 24a illustrates the system 310 with the elongated airless anchors 312 in a collapsed condition. FIG. 24b illustrates the system 310 with the elongated airless anchors 312 in an expanded condition. Generally, an airless anchor may be an anchor that can be mechanically manipulated from a collapsed condition to an expanded condition. For example, an airless anchor may comprise a metal mesh structure that is extended to collapse and then pressed together to expand outwardly. The inner actuator 306 and outer sleeve 303 of FIG. 23a may be coupled to a proximal end of the lead to facilitate user extension of the electrodes and expansion of the lead anchors. Another embodiment for an anchoring system is using inflatable balloons with saline or air. In one embodiment, the system includes one inflatable balloon which anchors the catheter in the bladder.

Figure 25:
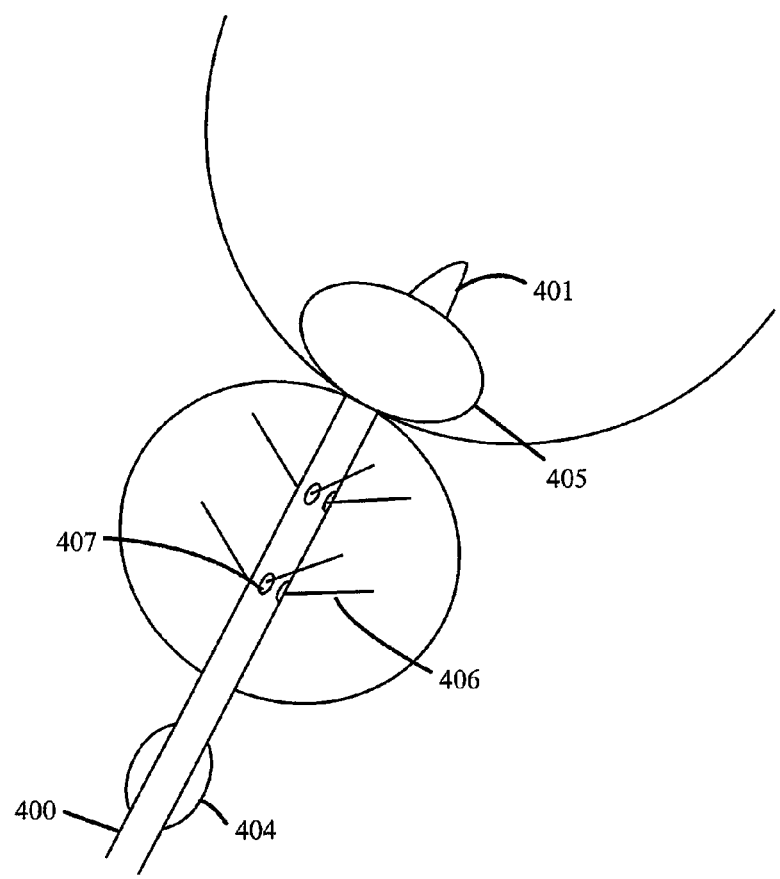
FIG. 25 illustrates a system for BPH treatment configured for insertion through the urethra until the distal end of the device is in the bladder, in accordance with one embodiment.

FIG. 25 illustrates a system for BPH treatment configured for insertion through the urethra until the distal end of the device is in the bladder. It is to be appreciated that modifications will be obvious to those skilled in the art for treatment of other tissues. In the embodiment shown, a distal balloon is inflated and the device is retracted into treatment position. Further, a proximal balloon may be inflated to hold the device in position and prevent the device from rotating while the electrodes are deployed. The ends of the electrodes may be uninsulated, may comprise a material resistant to electrochemical corrosion, and may have adjustable positions relative to the urethra, thus controlling the position and size of the treatment zone. When the treatment is completed, the electrodes are retracted, and the device removed.

The system may be positioned using the distal balloon 405 deployed from the distal tip 401 of the catheter into the urinary bladder. Once the balloon is inflated to an appropriate size, the catheter is retracted until the balloon is seated in the neck of the bladder. In one embodiment, the distal balloon is silicone and has a low inflation pressure. When deflated, the distal balloon 405 may have substantially the same shape as the tip 401 of the catheter and may be fit tightly to the tip 401. An air pressure pathway for inflation of the distal balloon 405 may be provided through the center of the tip. While each of the balloons discussed herein is discussed with respect to air inflation of the balloon, it is to be appreciated that the balloon may alternatively be inflated using any fluid. For example, in an alternative embodiment a saline solution may be used to inflate the balloon. The balloon could be inflated with between 5 and 60 cc of fluid or air to ensure adequate anchoring in the bladder. A suitable volume of fluid is 15 cc of saline. In one embodiment the catheter contains a port through the catheter to allow fluid to be drained from the bladder.

FIG. 25 illustrates the catheter 400 with the proximal and distal balloons 404 and 405 inflated and the electrodes 406 in an expanded configuration. The distal balloon 405 is located proximate to the tip 401 and is coupled to the outer sheath of the catheter. An electrical wire attaches to each row of electrodes and runs through the inner sheath of the catheter 400 to wire/air pressure tubing in the handle. The uninflated proximal balloon 404 is attached to the outer sheath of the catheter 400. The proximal balloon 404 is positioned outside the proximal urinary sphincter and is of a greater length than the tip balloon 405 so as to minimize any localized pain associated with its inflation.

The proximal balloon 404 is coupled to the outer sheath 413 of the catheter. In one embodiment, the proximal balloon 404 may have a relatively long length to minimize patient discomfort associated with balloon inflation. For example, the proximal balloon 404 may be approximately 5 cm long. Like the distal balloon 405, the proximal balloon 404 may comprise silicone and have a low inflation pressure. The positioning of the balloon is dependent on assuring that it is in the urethra but outside the external sphincter of the urethra.

As shown in FIG. 25, the distal balloon 405 inflates and locates the device in the bladder neck. The proximal balloon 404 inflates to approximately the size of the urethra to hold the linear and rotational position of the device in the urethra. The electrodes 406 extend through positioning holes 407 in an electrode director that directs the electrodes at a desired angle. As previously discussed, the electrodes may have axial electrode spacing and angular separation. The electrodes may be axially spaced, for example, 1 centimeter apart with one row angled up to both sides at a 15° angle to the horizontal axis (assuming positioning line is up). Further, one row of electrodes may be angled down at 40° on both sides. In one embodiment, the anterior electrodes may be 8 mm apart with the electrodes at 0 degree angle to the horizontal axis and the posterior row angled down at 35 degrees into both lobes of the prostate.

In accordance with various embodiments provided herein, the delivery catheter may deploy between 4 and 12 electrodes into the lateral lobes of the prostate to treat BPH. The number of electrodes used may depend on patient physiology. For example, a 4-electrode array may be appropriate to use on prostates between 20 and 80 cc in volume. In some embodiments, the system may be configured with four electrodes exiting the catheter in parallel in a plane approximately created by points an equal distance from the proximal edge of the bladder balloon. In other embodiments the electrodes may not exit the catheter in parallel or from the same plane within the catheter. In other embodiments between 2 and 12 electrodes may be deployed into the prostate from the catheter. In other embodiments between 4 and 8 electrodes may be deployed into the prostate.

Figure 26A:
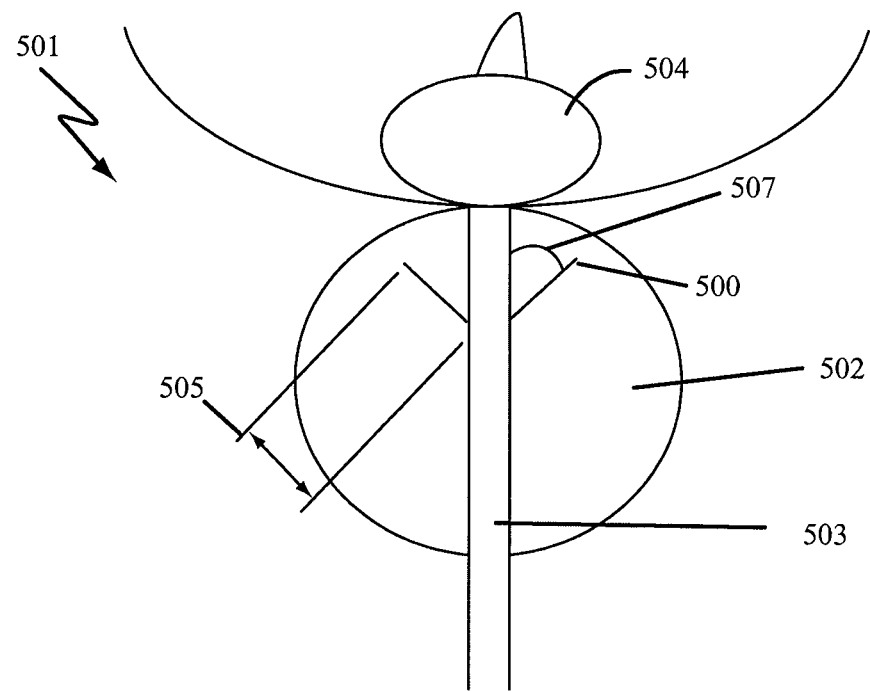
FIG. 26a illustrates a coronal view of a system having a forward angling electrode array, in accordance with one embodiment.
Figure 26B:
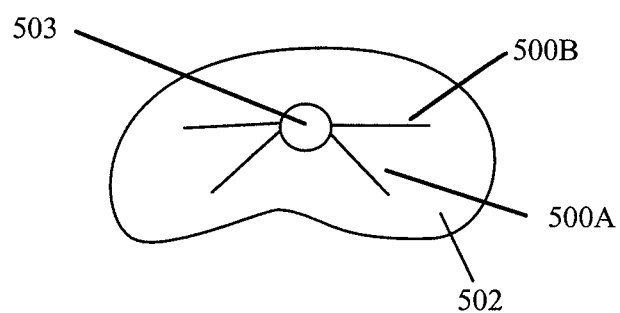
FIG. 26b illustrates a transverse view of a system having a forward angling electrode array, in accordance with one embodiment.

FIGS. 26a and 26b illustrate a system having a forward angling electrode array. As shown, the system 501 includes a catheter 503, electrodes 500 having a length of extension 505, and a fixation element 504. The electrodes 500 may be introduced into the prostate 502 angling towards the balloon at an angle 507 between 15 and 60 degrees. This type of electrode array will be called a forward angling electrode array. FIG. 26b illustrates angling of a posterior electrode 500a and an anterior electrode 500b. Other embodiments include a lateral electrode array having electrodes which extend out at an angle from 60 degrees to 120 degrees from the balloon along the catheter body, and an inverted electrode array which has an angle between 120 degrees and 165 degrees. In one embodiment, a forward angling electrode array has a 45 degree angle towards the distal end of the catheter.

The electrodes 500 may be introduced through the urethra 10 to 20 mm from the proximal edge of the fixation element 504. In one embodiment, an approximately 30 degree forward angle electrode may exit the catheter approximately 16 mm from the fixation element. In another embodiment, an approximately 45 degree forward angle electrode may exit the catheter approximately 14 mm from the fixation element. In yet another embodiment, an approximately 15 degree forward angle electrode may exit the catheter approximately 18 mm from the fixation element. It is appreciated that small changes in this dimension will have only small changes on the safety and efficacy of treatment. Mismatch of forward angle and the distance between electrode and the fixation element may have undesirable effects on safety and efficacy.

In some embodiments, the electrodes 500 may extend from the catheter a length of extension 505 of approximately 14 to 22 mm. In one embodiment, the length of extension may be approximately 18 to 20 mm for a forward angling electrode array.

Referring to FIG. 26b, the anterior electrodes 500b may be configured to protrude from the catheter 503 at an angle between −15 and 15 degrees from the horizontal axis. In one embodiment, the anterior electrodes 500b may be configured to protrude from the catheter 503 at an approximately 0 degree angle from the horizontal axis. This includes forward, lateral and inverted electrode arrays.

The posterior electrodes 500a may be configured to protrude between 25 and 65 degrees from the anterior electrodes 500b. In one embodiment, the posterior electrodes 500a protrude approximately 35 degrees from the anterior electrodes 500b. This includes forward, lateral, and inverted electrode arrays.

In various embodiments, the active portions of the electrode may be between approximately 3 and 12 mm long at the end of the insertion length of the electrodes as they deploy into the prostate tissue. In one embodiment, the active portion of the electrode may be between approximately 6 and 8 mm. This allows for between 10 to 14 mm of insulation on the electrodes in the preferred embodiment for urethral protection in a forward angling electrode array.

Figure 27:
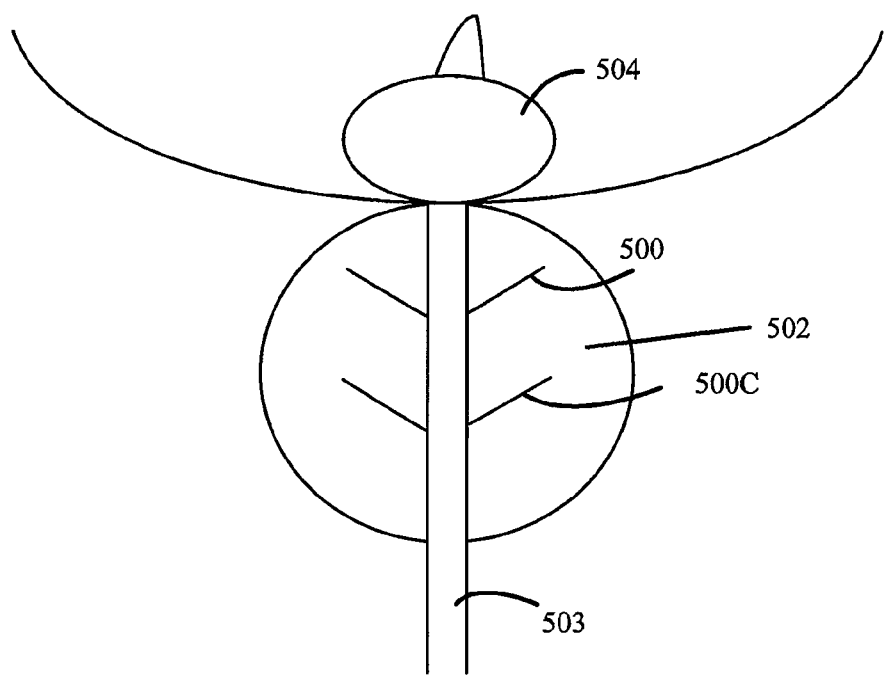
FIG. 27 illustrates an 8-electrode array in two rows of four, in accordance with one embodiment.

FIG. 27 illustrates an 8-electrode array in two rows of four electrodes (posterior electrodes are not shown as they are aligned with the anterior electrodes). As shown, the system 501 includes a catheter 503, electrodes 500 and 500c, and a fixation element 504. The electrodes 500 may be introduced into the prostate 502 angling towards the balloon at an angle between 15 and 60 degrees. Generally, an 8-electrode array may be configured similarly to the 4-electrode array shown in FIGS. 26a and 26b with the addition of a proximal plane of 4 electrodes 500c which are spaced approximately 6 to 12 mm from the distal 4 electrodes 500. In one embodiment, the spacing between the first array of electrodes 500 and the second array of electrodes 500c may be approximately 8 mm. This configuration of electrodes may be suitable for treatment of prostates in the size range of 40 and 100 cc in volume.

Each of the embodiments of the system for treating tissue comprises catheters and electrodes as described above and further comprises an electronic control system or generator. The electronic control system or generator may be connected to the catheter by an extension therapy cable to transfer the DC current controlled by the generator into the catheter that is delivered through the tissue contacting electrodes. In some embodiments, the extension therapy cable may be between approximately 3 and 20 ft in length. In one embodiment, the therapy cable is approximately 10 ft in length.

Figure 28:
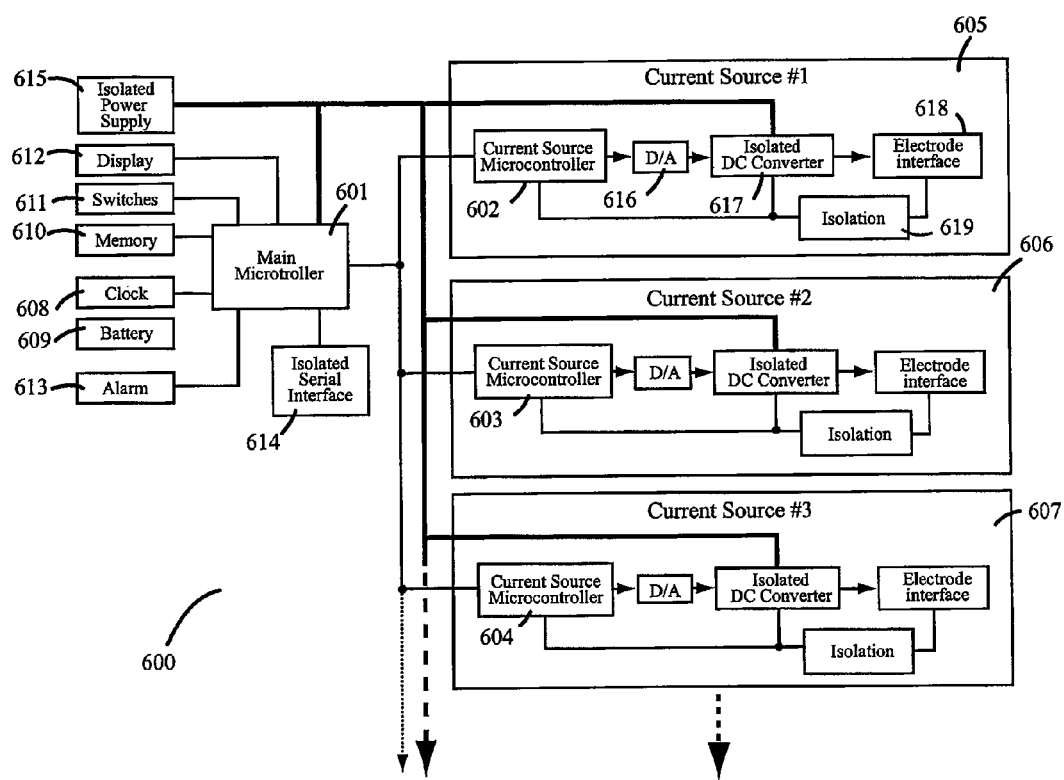
FIG. 28 is a block diagram of a generator, in accordance with one embodiment.

FIG. 28 is a block diagram of a generator 600 in accordance with one embodiment. A main microcontroller 601 communicates with a current source microcontroller 602, 603, 604 contained in each isolated current source 605, 606, 607 respectively. The main microcontroller 601 also controls the operator interface. Although FIG. 28 shows three isolated current sources, this is intended to be illustrative only and any number of current sources may be used. To control the timing of the therapy, the main microcontroller 601 may utilize, for example, a clock 608 powered by battery 609. As is standard in the art, the microcontroller may utilize a memory 610 and switches 611 and may utilize a display 612, as well as an alarm 613 and an isolated serial interface 614. An isolated power supply 615 may be provided to power the main microcontroller 601 and the isolated current sources 605, 606, 607. Using isolated current source 605 as an example, each current source may include a current source microcontroller 602, a D/A converter 616, an isolated DC converter 617, an electrode interface 618, and an isolation circuit 619.

The current or voltage level and amount of charge to be delivered by the generator 600 may be programmable and may be set via switches 611 and display 612. The generator 600 can function as a stand-alone device or may be controlled by an external controller such as a personal computer in which case treatment parameters may be set via the personal computer. The generator 600 may automatically set current, voltage and charge for all current sources based upon a setting entered by the user. The size of the treatment zone is dependent on the amount of charge delivered to the electrodes as well as the electrode shape and size. The treatment time is dependent on the current level and the amount of charge delivered. Different current sources 605, 606, 607 may be programmed with different settings to make treatment zone shapes and sizes match prostate (or other tissue) anatomy.

The generator 600 may contain any suitable number of individual current sources 605, 606, 607. When more than one current source is used, each current source may be isolated from the other current sources. Isolation between current sources may be used to improve control of current delivery. Without isolation between current sources, current may flow in the lowest impedance path which could cause some electrodes to deliver more treatment than intended and others to deliver less treatment than intended. Patient safety isolation may be provided by isolated power supply 615 and isolated DC converter 617 as well as isolation 619. Each of the independent current sources can be programmed to deliver a different dose and can be also programmed as anode or cathode. Main microcontroller 601 software permits only logical selections of anodes and cathodes.

The generator 600 may further measure the current delivered and the voltage between anodes and cathodes. It can stop current delivery when the correct charge has been delivered. It can also cease current delivery if it detects current or impedance faults.

In one embodiment, the generator may be designed to deliver current to multiple electrodes simultaneously and to control the amount of current dose to each electrode. In some embodiments one generator may be used to control between one and 6 pairs of electrodes. In one embodiment, the generator may be designed to control four pairs of electrodes. A system for treating tissue using DC ablation, as provided herein, may use a controlled dosage of current delivered to more than two electrodes. When the impedance between each electrode and its surrounding tissue is different, the current flows through the lowest impedance path, which may result in some electrodes delivering more current than others. Thus, the generator may be designed to control the current to each electrode.

In yet a further embodiment, a resistor-capacitor (RC) and/or an inductor-capacitor (LC) filter circuit may be incorporated into the generator circuitry to reduce the electrical noise caused by a switching power supply.

Pain experienced by patients during treatment of tissue by DC ablation, as provided herein, may vary by patient, tissue type, and proximity to sensory nerves. A patient may experience pain during DC ablation due to the level of current delivered via the electrodes. For some patients, the current delivery may be painful above a certain current threshold and that threshold may vary between patients. Pain may be relative to the current delivered by one pair of electrodes or may be relative to the cumulative current delivered by multiple pairs of electrodes. The DC ablation treatment time is directly affected by the current level. Treatment time can be reduced by increasing current. Thus, if the patient is not experiencing pain, the current level may be increased to reduce treatment time. One embodiment provides a current generator that facilitates adjustment of current level to reduce treatment time (thus increasing current) or to reduce pain during treatment (thus decreasing current).

Pain associated with DC ablation may be reduced for patients who are less tolerant of the process by reducing the ramp rate of the current and reducing the steady state current magnitude. Different patients have different tolerance levels for pain and, thus, the ramp rate and current magnitude at steady state may vary between patients. Generally, for most patients, a suitable ramp rate is between approximately 0.1 and approximately 10 mA/second. Maintaining a current level for a period of time can reduce patient pain at any level of DC current. Thus, in one embodiment, current levels are maintained for a period between approximately 15 seconds and approximately 30 seconds.

Figure 29:
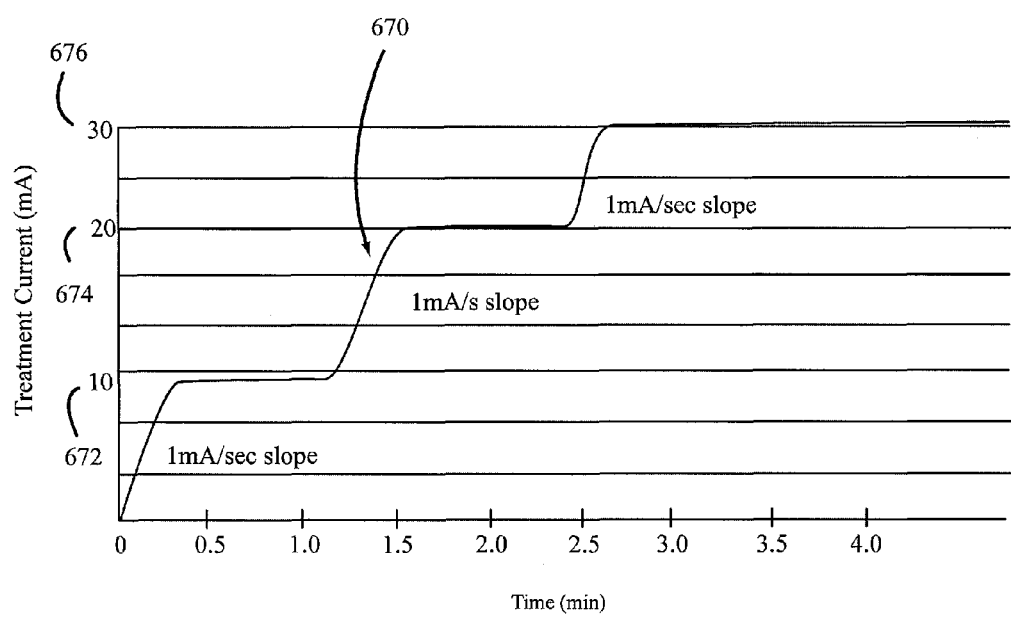
FIG. 29 illustrates a current profile for reducing pain associated with DC ablation, in accordance with one embodiment.

FIG. 29 illustrates a current profile 670 for reducing pain associated with DC ablation. As shown, the treatment ramps to three different levels 672, 674, 676 of current and maintains those levels of current for a period of time before ramping up again. Specifically, in the embodiment shown, the current is ramped up at approximately 1 milliampere/second. After approximately 10 seconds of ramping, the current is maintained at approximately 10 mA (shown at 672) for approximately 50 seconds (thus until a total treatment time of approximately 1 minute). The current is then ramped up for approximately 10 seconds until a current level of approximately 20 mA (shown at 674) is reached. That current is maintained for approximately 50 seconds. The current is then ramped up again for approximately 10 seconds until a current level of approximately 30 mA (shown at 676) is reached. The current is then maintained at approximately 30 mA. Thus, in the embodiment shown, current is ramped up for approximately 10 seconds and maintained for approximately 50 seconds with this being repeated until a desired current level is reached. The ramp rate (1 milliAmpere/second in the embodiment shown) may vary as suitable for the patient and the application. In some embodiments, the ramp rate may vary between, for example, 0.1 milliampere/second and 10 milliampere/second. The duration of ramping between current level maintenance and the duration of the current level maintenance may also vary. While the embodiment of FIG. 29 illustrates maintaining current at three levels 672, 674, 676 (10 mA, 20 mA, and 30 mA), more or fewer levels of stable current may be used and the magnitudes of current may vary, though, generally, treatment may be done between about 10 mA and about 50 mA. Slowly ramping up the current rate and maintaining the current at interim levels can reduce the amount of pain experienced by a patient who is more sensitive to pain—for example, one who has received suboptimal anesthesia.

In a further embodiment, a portable generator is provided. Generally, the generator may be relatively small and have a handle. In one embodiment, the generator has a height of less than about 100-150 mm, a width of less than about 300 mm, and a length of less than about 400 mm. The generator includes a power connector for connecting power thereto. The connector may include electrical components for improvement of immunity to electromagnetic interference (EMI). The generator further includes a cable connector for connecting a cable thereto. The generator includes a computer serial port or a wireless port. The computer serial port and the wireless port facilitate communication between the generator and a computer or external memory device.

The generator, extension cable, and catheter each have one conductor for each electrode and may have an additional conductor to allow the generator to determine whether the extension cable and/or catheter are connected to the generator. On the catheter or extension cable connector, the anode pin of one current source may be connected to the additional conductor. The additional conductor may be connected to a circuit in the generator that measures the voltage of the additional conductor. When the start button is pressed to begin therapy, the generator may turn on the current source connected to the additional conductor and measure the voltage of the additional conductor. When the expected voltage is measured, the generator determines that the catheter and/or extension cable is attached and therapy is started. When the measured voltage is not as expected, the generator determines that the catheter and/or extension cable is not attached and therapy is not started. The generator may also detect whether the extension cable and/or catheter is attached by using digital communication with a circuit in the cable or catheter, either via wires or wireless communication.

In accordance with various embodiments, the generator thus comprises switches and a display. The switches facilitate entering of settings and controlling of therapy. The switches may comprise membrane switches, push-button switches, may be incorporated into a display using a touch-screen format, or may have another configuration. The display shows information to a user. The display may be, for example, a liquid crystal display (LCD). The display may display text or may display graphics. The display may be monochrome or color or may be backlit. In some embodiments, the display is a touch-screen display. Generally, the switches may be located proximate the display to allow the user to view the display while actuating the switches. In touch screen embodiments, the switches may be incorporated into the display.

FIG. 30a-30d illustrate an embodiment of a touchscreen display layout of a generator.

Figure 30A:
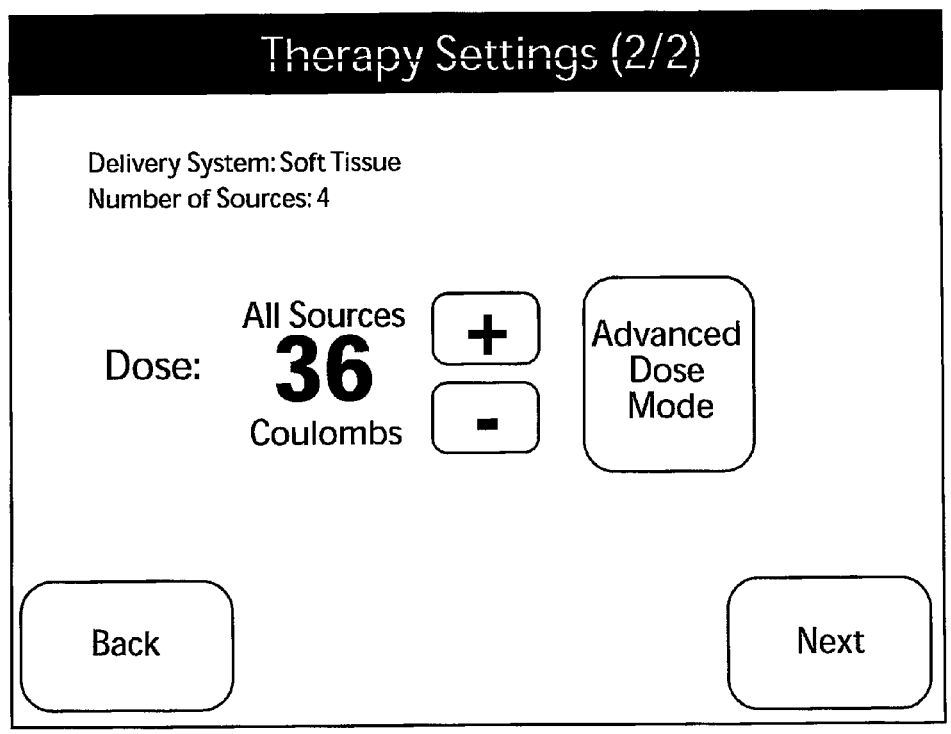
FIG. 30a illustrates a Therapy Settings screen of a generator display, in accordance with one embodiment.

FIG. 30a illustrates a Therapy Settings screen, where the dose (charge) setting for all current sources can be adjusted at the same time using the '+' and '−' buttons. Pressing the 'Advanced Dose Mode' button allows for adjusting the dose (charge) of each individual current source. When the 'Next' button is pressed, the display goes to the screen shown in FIG. 30b.

Figure 30B:
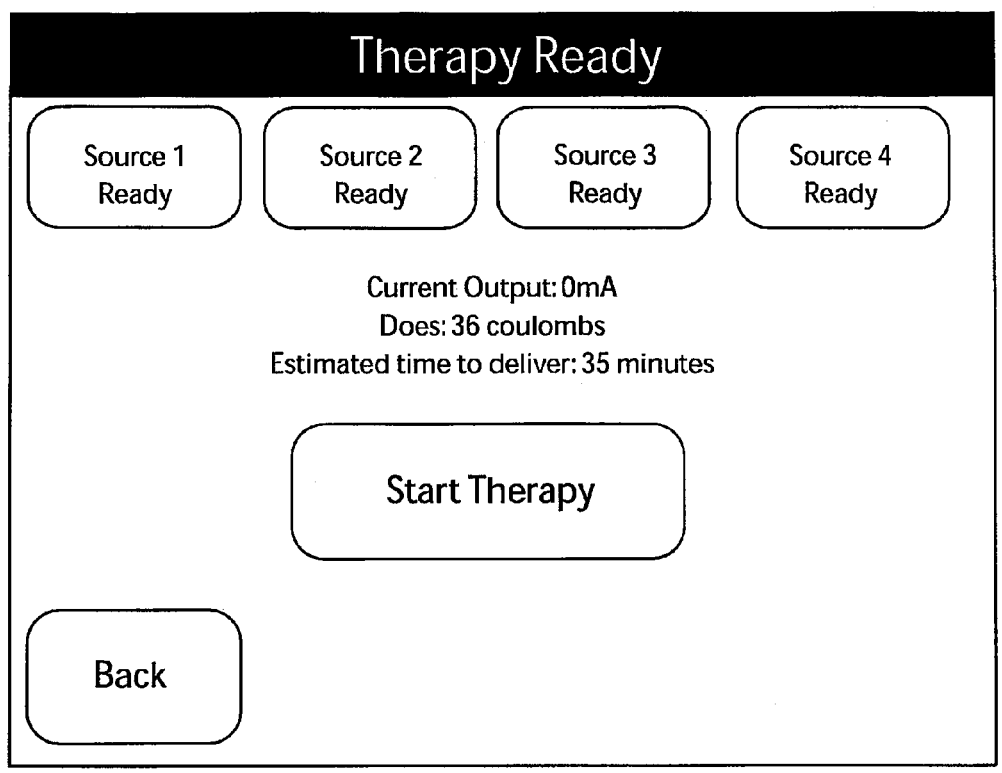
FIG. 30b illustrates a Therapy Ready screen of a generator display, in accordance with one embodiment.

FIG. 30b illustrates a Therapy Ready screen. The selected dose (charge) setting is shown along with an estimated treatment time. Treatment can be started by pressing the 'Start Therapy' button. When the 'Back' button is pressed, the display goes to the screen shown in FIG. 30a.

Figure 30C:
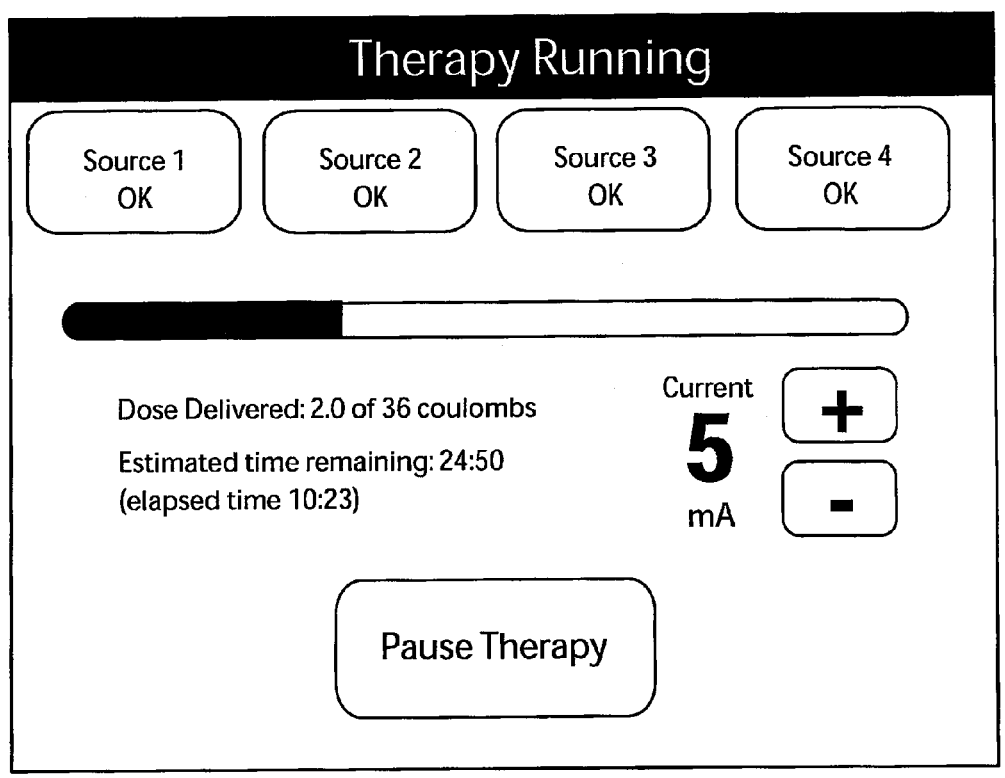
FIG. 30c illustrates a Therapy Running screen of a generator display, in accordance with one embodiment.

FIG. 30c illustrates a Therapy Running screen. The amount of dose (charge) delivered, estimated treatment time, and elapsed time are updated at approximately once per second while therapy is running. Pressing the 'Source X' button causes additional therapy information for current source #X to be shown, including measurements of current and impedance. The current magnitude may be increased or decreased by pressing the '+' button or '−' button. Treatment may be paused by pressing the 'Pause Therapy' button.

Figure 30D:
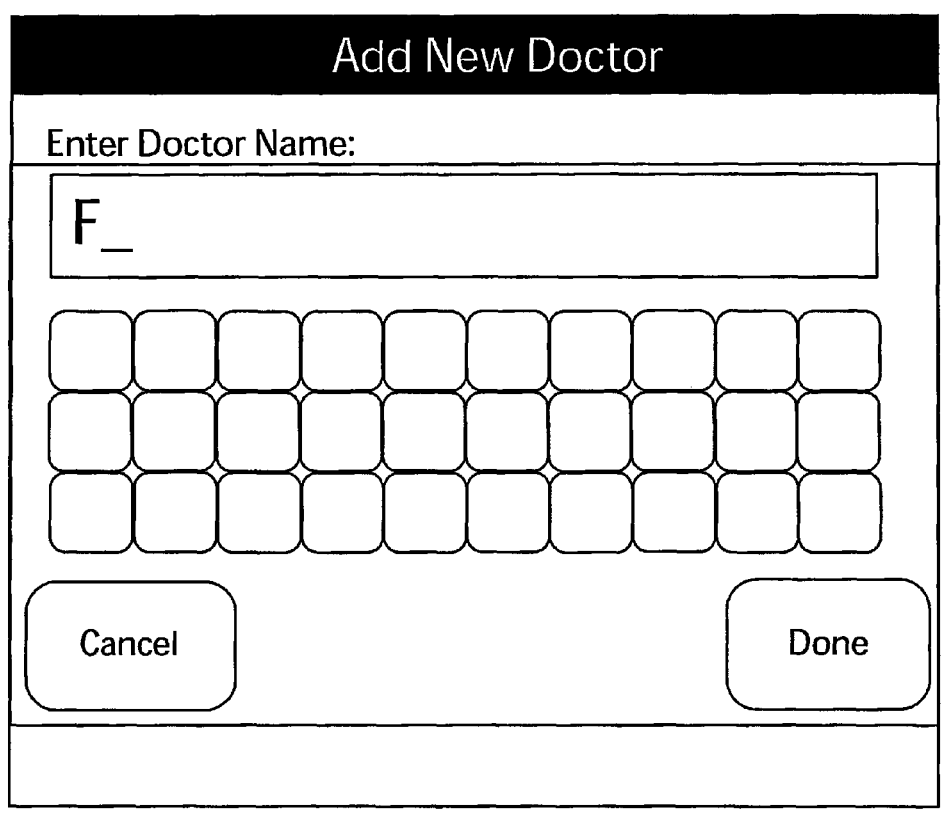
FIG. 30d illustrates an Add New Doctor screen of a generator display, in accordance with one embodiment.

FIG. 30d illustrates an Add New Doctor screen, including a QWERTY keyboard which may be used to enter a doctor's name. The user may cancel the entry of the doctor's name by pressing the 'Cancel' button or may accept the name by pressing the 'Done' button.

Figure 30E:
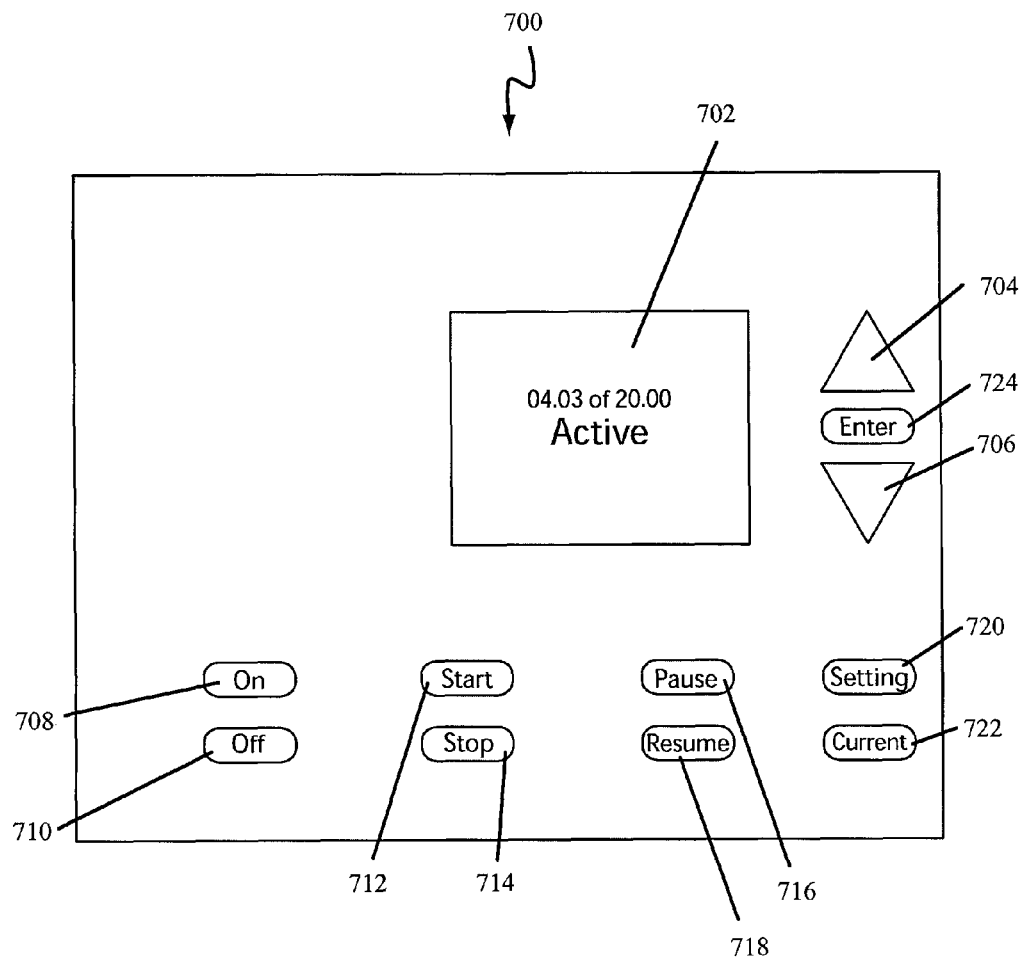
FIG. 30e illustrates a switch and display layout of a generator, in accordance with one embodiment.

FIG. 30e illustrates an alternative display for a generator. The generator 700 includes a display 702, an increase switch 704, and a decrease switch 706. The switches 704, 706 may provide feedback via switch detent or audible beep and, in some embodiments, visual feedback via the display. To turn the generator power on and off, the generator may provide separate On and Off switches 708, 710 or a single On/Off switch that may be actuated between positions. To start and stop treatment, the generator 700 may provide separate Start and Stop switches 712, 714 or a single Start/Stop switch. The generator 700 may provide a means for pausing treatment allowing treatment to be resumed instead of re-started from the beginning. To pause and resume treatment, the generator 700 may provide separate Pause and Resume switches 716, 718 or a single Pause/Resume switch, or a pause position on the On/Off switch.

A mechanism for adjusting the current level while treatment is in progress may be provided. A single switch for increasing and decreasing current may be provided. In an alternative embodiment, separate switches for increasing current and decreasing current may be shown. In yet an alternative embodiment, the generator may have a current switch, such as 722 of FIG. 30e, along with up and down switches 704, 706. In such an embodiment, the setting may be changed by pressing the current switch 722 followed by either the up switch 704 or the down switch 706, or by pressing either the up switch 704 or down switch 706 at the same time as the current switch 722.

The generator further may comprise a means for entering a treatment setting or settings. Such mechanism may comprise switches such as those described with respect to current. Thus, a single switch may be provided for increasing and decreasing setting. In an alternative embodiment, separate switches may be provided for increasing setting and decreasing setting. In yet an alternative embodiment, the generator may have a setting switch, such as 720 of FIG. 30e, along with an up switch 704 and a down switch 706. In such an embodiment, the setting may be changed by pressing the setting switch 720 followed by either the up switch 704 or the down switch 706, or by pressing either the up switch 704 or the down switch 706 at the same time as the setting switch 720.

In some embodiments, when entering the generator setting, the display 702 may show the entered setting. If the setting is being changed, the display may show the proposed new setting. Proposed new settings may be shown differently from settings that have been entered, such as by showing proposed new settings in a blinking or flashing manner while showing entered settings without blinking or flashing. Accordingly, an enter switch 724 may be provided to confirm proposed settings or currents.

During treatment, the display 702 may show the treatment time remaining, the total expected treatment time, and the status of the generator. The status may be, for example, Starting, Active, Pausing, Resuming, Changing Current Level, or Stopping. Showing the status provides feedback to the user after a switch has been pressed.

The generator may incorporate different display modes, for example, User Mode and Clinician Mode. In Clinician Mode, the display may show more information than shown in User Mode. Items that may be shown in Clinician Mode may include, for example, the setting, current measurement, impedance measurement, current level setting, and charge setting.

The treatment parameters may be determined by settings entered by the user. Generally, treatment parameters may include current level, charge, or time. Setting information may be shown on the display. Settings may be entered by setting the parameters for each current source individually or by using switches to select a current source and then to select a parameter and a setting. Settings may be entered by setting the parameters for current sources at the same time by using switches to select a parameter and a setting. In some embodiments, settings may be entered by selecting a setting from a settings table stored in the generator memory. A separate settings table may exist for each current source, allowing for setting up each current source individually. A single settings table can contain parameter settings for all current sources, allowing for all current sources to be set up using one setting.

In another embodiment the generator would allow the physician to enter the dimensions of the structure to be treated into the generator and the generator automatically sets up the correct parameters for charge and/or current. One example is the physician inputs the transverse width, sagital length, anterior-posterior height and/or volume of the prostate and the generator sets itself up for the optimal treatment.

In various embodiments, settings may be different for each source or all sources may be set with the same parameters. A source may be set to not turn on by setting current and charge to zero. The settings in the table may be programmable via a serial port included in the generator, as previously described. Settings in the table may have names or numbers that correspond to a prostate size or dimension, allowing the setting to be selected based, for example, on a prostate measurement. Settings in the table may be provided on a label on the generator or in an instruction manual, showing which setting to use for different prostate sizes or dimensions.

In some embodiments, the generator may have stored, unalterable, settings. These settings may be referred to as Factory Settings. The settings may be stored in non-volatile memory to prevent them from being lost if power is disconnected. In some embodiments, the factory settings may be alterable by a user under certain conditions. The Factory Settings may include:

(1) Ramp Up Rate—determines the rate that the current level increases when starting or resuming treatment, 0.1-10.0 mA/second, default of 1.0 mA/second;

(2) Ramp Down Rate—determines the rate that the current level decreases when pausing or stopping treatment, 1-100 mA/second, default of 10 mA/second;
(3) Ramp Up Step Size—determines the increment in current level during ramp up, 1-1000 microamps, default of 10 microamps;
(4) Ramp Down Step Size—determines the increment in current level during ramp down, 1-5000 microamps, default of 100 microamps;
(5) Maximum Current—sets the maximum current level that can be set for each current source via the generator switches, 30-100 mA, default of 50 mA;
(6) Maximum Charge—sets the maximum charge level that can be set for each current source via the generator switches, 36-180 coulombs, default of 44 coulombs;
(7) Calibration constants—used by the generator software to improve the accuracy of current level settings, current measurements, and voltage measurements, slope and intercept constants for linear fit calibration;
(8) Increase Current Step Size—determines the increment in the current level setting when the Increase Current switch is pressed, 1-10 mA, default of 5 mA;
(9) Decrease Current Step Size—determines the decrement in the current level setting when the Decrease Current switch is pressed, 1-10 mA, default of 5 mA;
(10) Settings table—contains the current level and charge settings for each current source;
(11) Current level for detection of a low current fault, 75%-95% of current setting, default of 90%;
(12) Current level for detection of a high current fault, 105%-125% of current setting, default of 110%;
(13) Impedance level for detection of a low impedance fault, 10-200 ohms, default of 100 ohms;
(14) Impedance level for detection of a high impedance fault, 1500-5000 ohms, default of 2000 ohms;
(15) Storage Interval—determines timing for storing data to memory, 1-1800 seconds, default of 60 seconds;
(16) Model number;
(17) Serial number;
(18) Date of manufacturing;
(19) Minimum number of current sources, 1-4, default of 1;
(20) Maximum number of current sources, 1-4, default of 4; and
(21) Allow user selection of number of current sources, yes/no, default of yes.

Accordingly, a system and method for DC ablation of tissue is provided. In some embodiments, the system and method may be used with a transurethral approach for treating BPH by creating large lesions in less than 45 minutes. The procedure is minimally invasive and the patient can be fully awake during the procedure and only remains uncomfortable for a short period of time. In addition, the apparatus and method makes it possible for the physician to reduce his time required for the procedure. The apparatus and method also has an advantage in that it substantially eliminates multiple deployments of a device for treating a single prostate. This avoids difficulties associated with precise positioning of individual deployments in a treatment for single prostate. Using systems and methods as provided herein, a single deployment in the prostate relieves symptoms of BPH. In various embodiments, the system may operate in a mode where not all electrodes deployed into the prostate have charge delivered to them or have unequal charge delivered to them. It is possible to reconfigure the electrode pairs so that large lesions can be created without the necessity of redeployment of the device. During the procedure, a scope may be deployed to permit viewing of either or both pairs of needles. pH controls may be employed for monitoring and controlling the ablation procedure. pH sensors may be placed in various places including on the catheter, on a rectal probe, or on a percutaneous needle to monitor, control, or plan the treatment.

Although the invention has been described with reference to specific embodiments, persons skilled in the art will recognize that changes may be made in form and detail without departing from the spirit and scope of the invention.

EXAMPLES

The following examples are for illustrative purposes only and are not intended to be limiting.

Example 1

A study was performed to evaluate the chronic effects of DC ablation in canine prostates. Eight chronic canine subjects were treated to evaluate the healing cascade, dose response, prostate shrinkage, and the duration of time before necrotic tissues were reabsorbed into the body.

Treatment was performed on the subjects by performing a laparotomy and inserting electrodes through the prostate capsule. Treatment was performed at 40 mA and with a dose of between 4 and 70 C. The subjects' blood, urine, general health, and behavior patterns were monitored before sacrificing them at time intervals of 1, 3, 20, 40, and 60 days after treatment. The prostate and surrounding tissues were dissected and examined after sacrifice. Ultrasound and CT scans were used throughout the study to identify the necrotic lesions and identify any changes that took place to the lesion.

Figure 31A:
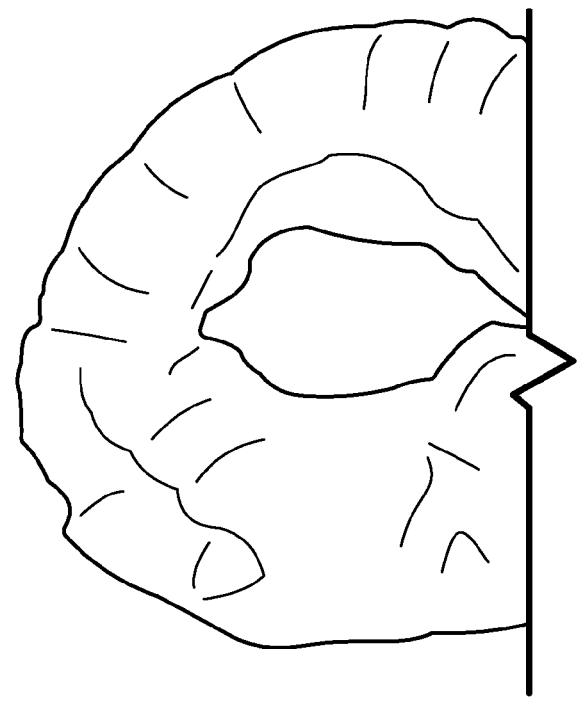
FIG. 31a illustrates a slice of prostate 20 days after treatment, in accordance with one embodiment.
Figure 31B:
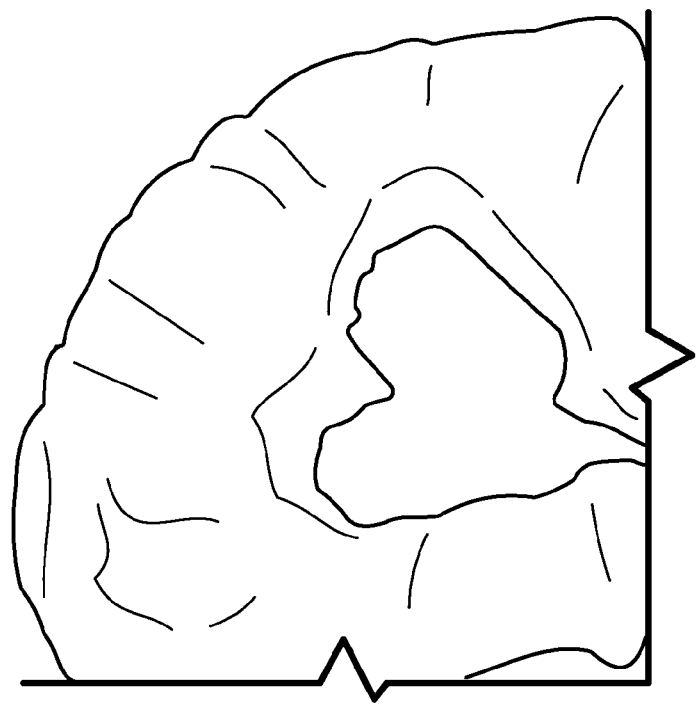
FIG. 31b illustrates a slide of prostate 40 days after treatment, in accordance with one embodiment.

Ultrasound, CT imaging, and visual verification during histology showed that voids or cavities were created in the prostate tissue in the necrotic areas induced by DC ablation. FIGS. 31a and 31b illustrate slices of prostate at 2 times of sacrifice through the center of treatment zones. FIG. 31a illustrates a slice of prostate 20 days after treatment. FIG. 31b illustrates a slice of prostate 40 days after treatment. The necrotic tissue was substantially absorbed into the body by the first screening date, 20 days after treatment. Reabsorption resulted in voids, shown in FIGS. 31a and 31b.

The voiding within the prostates caused the overall shape and size of the prostate to shrink. In one subject the prostate had a measured width of 40 mm prior to treatment. Twenty days after treatment, the prostate had a measured width of 28 mm.

The results of Example 1 show substantially complete absorption of the necrotic tissue with little or no fibrotic scarring. The tissue around the voids created by DC ablation remains soft and pliable without surrounding hardened scar tissue.

Sacrifice of the subjects and examination of the prostate showed that the necrotic tissue was contained within the capsule and all tissues in the pelvic cavity remained healthy. Within the prostate itself, tissue immediately adjacent to the necrotic zones remained healthy, illustrating a sharp diffusion gradient. The size of the voids created coincided with dose response algorithms previously developed. The studies thus confirmed that the treatment has a sharp diffusion gradient and a predictable dose response All subjects remained healthy throughout the study and maintained normal urination and defecation patterns without signs of straining or discomfort.

Histology Results: Following treatment, all animals were terminated and subjected to necropsy examinations. Representative prostate samples fixed in 10% neutral buffered formalin were trimmed in the coronal plane perpendicular to the urethra, and 1.5 to 2.5 mm sequential slices were photographed.

Bilateral coagulation to liquefaction necrosis was observed in both acute animals (Animals 7C161 and 7C163). There was minimal associated inflammation and mild hemorrhage. Bilateral multifocal to coalescing inflammation was observed in the subcapsular parenchyma in all six chronic animals (Animals 7C201, 7C206, 7C197, 7C199, 7C202 and 7C204). There were cellular infiltrates (primarily lymphocytes and macrophages) expanding the interacinar mesenchyme. Moderate to marked such reaction was observed in Animal 7C202 while the response was minimal to mild in the multiple sections from the remaining animals from the three chronic observation periods.

Acinar atrophy characterized by reduction of lobular and sublobular clusters of glands with reduction of lumen and lining with attenuated cells was a consistent finding in all chronic animals. The intensity ranged from minimal to moderate. Moderate acinar atrophy was observed in multiple sections of all chronic animals except Animal 7C204 from the 60 day group, in which the reaction was minimal in four of the five sections studied.

Bilateral loss of parenchyma leading to formation of cavities was present in multiple sections from all six chronic prostate samples. These cavities were variable in size and often coalesced with the adjacent urethra. In most sections, a unilateral cavity merged with the urethra. In a few sections the urethra merged with bilateral cavities on either side of the prostate. The cavities often were lined by urothelium, possibly a regenerative and reparative response from the communicating urethral epithelium. Presence of cavities that represented loss of tissue mass from DC ablation in all the specimens from three treatment groups suggest the lasting effect of reducing prostate mass by DC ablation over a period of 60 days. Also, there was no significant inflammatory reaction in the tissue surrounding the cavities, suggesting such union of necrotic tissue cavity and urethra either did not incite inflammatory response or the inflammation had receded and resolved completely at the time points of observation. Additionally, the urethra had one or many of the changes that included epithelial discontinuity in the form of erosion and ulceration, focal subepithelial inflammation and minimal hemorrhage, intracytoplasmic vacuolation of urothelium over a segment of urethra, focal aggregate of luminal necrotic cellular debris, patchy granulation tissue in the adjacent stroma and a marginal increase in periurethral mesenchyme.

Cystic dilation of glandular acini of variable degrees, ranging from isolated focal area to a substantial proportion of the remaining prostate gland, was observed in all the animals. These changes were present in multiple sections in the same animal. The changes were minimal in Animal 7C202. The dilated acini were lined by cuboidal to attenuated cells and occasionally contained sloughed cells, cellular debris and secretory product. Within the atrophic acini, multifocal expanding islands of regenerating glands were observed in a few animals. The foci of regeneration impinged the adjoining atrophic gland and were comprised of arborizing acini lined by tall columnar cells with abundant eosinophilic cytoplasm, vesicular nuclei with rare mitotic figures.

The study showed a reduction in the prostatic tissue mass using DC ablation as evidenced by loss of tissue surrounding the electrode insertion sites and atrophic changes incited elsewhere within the gland. The effects were persistent and observed in multiple sections of prostates at 20, 40 and 60 days following the treatment procedure. The merging of device-induced cavities and the urethra is likely a portal of drainage for the necrotic tissue mass contributing to the minimization of the inflammatory reaction in the remaining tissue.

Example 2

A study was performed to determine comparative size of the treatment region of a volume of tissue treated with a cathode and a volume of tissue treated with an anode. Beef round samples and in-vitro canine prostates were treated.

The following protocol were used to examine the amount of treated volume in beef round samples and in prostate at both the anode and the cathode:

1a. Treat beef samples with the following currents: 20, 40, and 60 mA.

1b. Treat in-vitro prostates with 40 mA current.

2a. Treat beef samples with the following doses: 36, 72, 108, and 144 C.

2b. Treat in-vitro prostates with 4 and 13 C of dose.

3. Soak samples in formalin solution for a minimum of approximately 48 hours.

4. Slice samples with meat cutter into approximately 3 mm slices.

5. Measure thickness of each sample at anode and cathode treatment.

6. Photograph each slice.

7. Measure area of treatment in each sample using Microsoft Visio™ software.

8. Calculate volume treated (post-fixation) for anode and cathode.

9. Compare data.

Beef round samples were tested with 12 mm simple Pt Ir pin electrodes. Prostate samples were tested with various pin and coil sizes. Results are shown in Tables 7 and 8, below.

TABLE 7

Beef Round Results

| Dose (C) | Current (mA) | Cathode Volume (cc) | Cathode Std Dev (cc) | N (Samples Tested) | Anode Volume (cc) | Anode Std Dev (cc) | N (Samples Tested) |
| --- | --- | --- | --- | --- | --- | --- | --- |
| 4 | 20 to 60 | 0.22 | 0.04 | 3 | 0.15 | 0.00 | 3 |
| 36 | 20 to 60 | 1.18 | 0.26 | 9 | 1.24 | 0.18 | 9 |
| 72 | 20 to 60 | 2.45 | 0.47 | 9 | 2.33 | 0.23 | 9 |
| 108 | 20 to 60 | 3.09 | 0.64 | 22 | 3.23 | 0.93 | 22 |
| 144 | 20 to 60 | 3.95 | 0.29 | 9 | 4.23 | 0.66 | 9 |

TABLE 8

| Dose (C) | Current (mA) | Cathode Volume (cc) | Cathode Std Dev (cc) | N (Samples Tested) | Anode Volume (cc) | Anode Std Dev (cc) | N (Samples Tested) |
|---|---|---|---|---|---|---|---|
| 4 | 40 | 0.29 | 0.24 | 3 | 0.24 | 0.06 | 3 |
| 13 | 40 | 0.76 | 0.17 | 3 | 0.86 | 0.19 | 3 |

Figure 32:
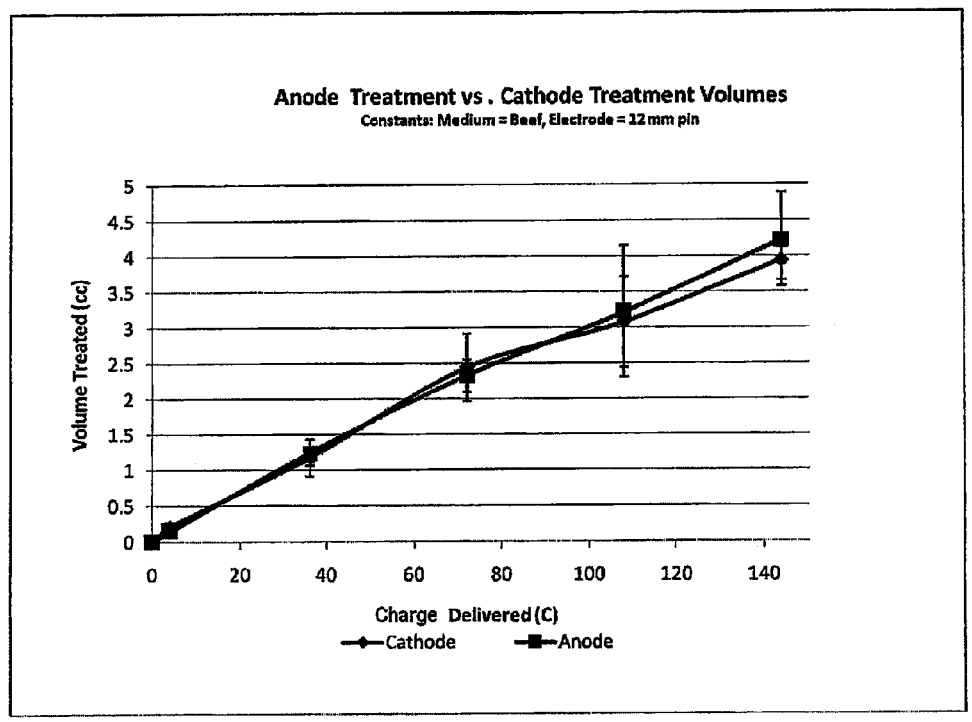
FIG. 32 illustrates treatment volume against charge delivered for anode treatment and cathode treatment for beef rounds, in accordance with one embodiment.

FIG. 32 illustrates treatment volume against dose delivered for both anode treatment and cathode treatment for beef rounds. As shown in FIG. 32 there is no significant difference in treatment volumes between the anode and the cathode.

Example 3

A study was performed to determine the effects of delivering a dose at different currents on the amount of treated volume. Beef round samples were treated. Protocol used for Example 3 followed the protocol of Example 2 for beef round samples.

The results of the study indicated that in the range of current between 20 and 60 mA, there is substantially no appreciable difference in the results of treatment.

Results are shown in Tables 9 and 10, below.

TABLE 9

Cathode Results

| Dose (C) | Current (mA) | Cathode Volume (cc) | Cathode Std Dev (cc) | N (Samples Tested) |
|---|---|---|---|---|
| 4 | 40 | 0.22 | 0.04 | 3 |
| 36 | 20 | 1.04 | 0.22 | 2 |
| 36 | 40 | 1.08 | 0.15 | 4 |
| 36 | 60 | 1.40 | 0.33 | 3 |
| 72 | 20 | 2.33 | 0.13 | 2 |
| 72 | 40 | 2.36 | 0.42 | 4 |
| 72 | 60 | 2.65 | 0.73 | 3 |
| 108 | 20 | 2.50 | 0.37 | 3 |
| 108 | 40 | 3.27 | 0.62 | 15 |
| 108 | 60 | 2.85 | 0.62 | 4 |
| 144 | 20 | 3.98 | 0.24 | 2 |
| 144 | 40 | 3.86 | 0.33 | 4 |
| 144 | 60 | 4.05 | 0.33 | 3 |

TABLE 10

Anode results

| Dose (C) | Current (mA) | Anode Volume (cc) | Anode Std Dev (cc) | N (Samples Tested) |
|---|---|---|---|---|
| 0 | | 0 | 0 | 0 |
| 4 | 40 | 0.15 | 0.00 | 3 |
| 36 | 20 | 1.23 | 0.01 | 2 |
| 36 | 40 | 1.32 | 0.21 | 4 |
| 36 | 60 | 1.15 | 0.18 | 3 |
| 72 | 20 | 2.08 | 0.00 | 2 |
| 72 | 40 | 2.53 | 0.17 | 4 |
| 72 | 60 | 2.23 | 0.11 | 3 |
| 108 | 20 | 3.03 | 0.95 | 3 |
| 108 | 40 | 3.31 | 0.92 | 15 |
| 108 | 60 | 3.04 | 1.15 | 4 |
| 144 | 20 | 4.10 | 0.13 | 2 |
| 144 | 40 | 4.49 | 0.42 | 4 |
| 144 | 60 | 3.97 | 1.09 | 3 |

Figure 33:
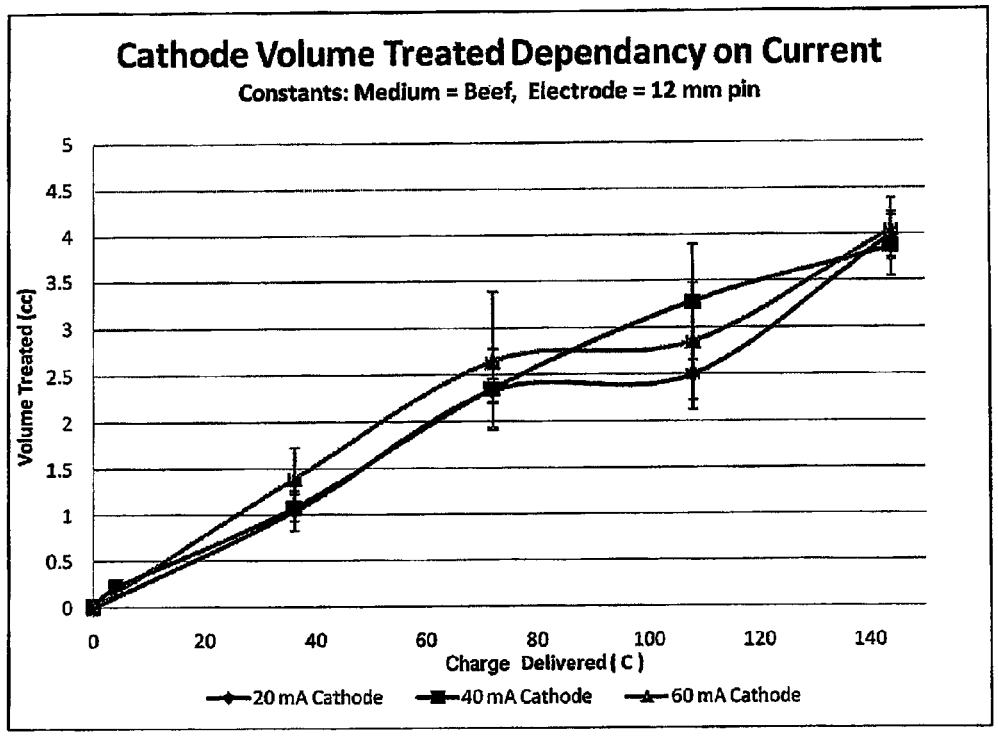
FIG. 33 illustrates cathode results for treatment volume against charge delivered for a 20 mA cathode, a 40 mA cathode, and a 60 mA cathode, in accordance with one embodiment.

FIG. 33 illustrates the data in Tables 9 and 10. FIG. 33 illustrates cathode results for treatment volume against dose delivered for a 20 mA cathode, a 40 mA cathode, and a 60 mA cathode.

As shown in FIG. 33, the dose to volume relationship is not influenced by the magnitude of current delivered to the electrodes up to 144 C and with a current between 20 and 60 mA. The relationship between dose and volume treated is linear. The variation between dose and volume increases with dose, presumably due to the sensitivity of the radius of treatment zone on the volume.

Example 4

A study was performed to determine the margin of safety that the capsule provides from causing damage external to the prostate. Canine subjects were treated.

Two canines were treated with doses that were expected to interact with the capsule. The following parameters were looked at to determine whether the dose delivered caused harm to the patient by causing necrosis to tissues outside of the capsule:
1. Comparison of the ratio between actual treatment and the expected efficacious treatment.
2. Visual observation of blackened tissue outside of the capsule due to treatment.
3. Visual observation of blackened tissue visible on the capsule.
4. Histological evidence of capsule remaining.

The two canine prostates had transverse widths of approximately 33 mm and 20 mm respectively and were treated with 16 mm coil electrodes. Using these transverse widths and assumptions listed below, a Targeted Prescribed Dose was determined for each prostate.

Assumptions:
a. Treatment diffuses equally from electrode.
b. Tissue dose response is in the range of 18 to 30 C/cc for canine prostatic tissue.
c. Targeted Prescribed Dose incorporates a 10% radius safety margin to the capsule while preserving a 6 mm diameter in the center of the prostate for the urethra.
d. Targeted Prescribed Dose is the midpoint between the dose resulting in a treatment radius following the above assumptions.

Targeted and Actual Doses delivered to the two subjects are shown in Table 11, below.

Resulting Target and Actual Doses Delivered to the Two Subjects in this Study

TABLE 11

| Subject | Targeted Prescribed Dose | Actual Delivered Dose | Over Dose |
|---|---|---|---|
| Subject 1 | 64 C # | 70 C | 1.1:1 |
| | 42 C ## | | 1.6:1 |
| Subject 2 | 16 C # | 24 C | 1.5:1* |
| | 16 C # | | 1.5:1* |

*Indicates a dose was delivered that was 50% over recommended aggressive dosing.
Indicates dosing if placement of electrode is absolute with a 10% safety margin from interaction with capsule tissues
Indicates dosing if placement error of electrode is known and no safety margin accounted for in dosing Tissues adjacent to the prostate were affected at the right caudal end. This lobe was treated by the anode. Based on the position and length of the anode electrode, and taper of this prostate anatomy, it was determined that the electrode was no further than approximately 2 mm from the capsule. If it is assumed that the electrode is 2.5 mm from the capsule, the predicted target dose may be about 9 C. This calculates to a 2.6 to 1 Over Dose ratio in the right caudal portion of this prostate with 16 mm electrodes.

After treatment in both subjects, a blackened treatment zone was visible on the left lateral side of the prostate in Subject 1. Tissue adjacent to this zone appeared healthy. This illustrates that the treatment zone did diffuse far enough that it interacted with the capsule. The fact that no necrotic tissues were observed in adjacent tissue indicates that the hydrogen and hydroxyl ions were contained within the capsule.

The capsule of Subject 2 saw extensive treated tissue up to the capsule boundary at the cathode, presumably due to both the overtreatment of the capsule and the electrodes being placed closer to the outer capsule than the urethra. This biased the treatment towards the capsule more than would be expected with a 10% overdose. The overdose ratio was recalculated using the actual distance from the capsule and it was found that the cathode in Subject 2 was overdosed by 60%.

Examining the histology in areas where the treatment visually was adjacent to the capsule was not definitively conclusive due to the fact that the slide preparation process can be destructive to these boundary tissues. Histological evidence and the pathologist's conclusions indicated that the cellular structures making up the capsule showed necrosis but the capsule's structural integrity was maintained. This assessment agrees with the visual observations seen during the procedure and necropsy with the exception of the right caudal portion of the prostate of Subject 2.

In this acute animal study, prostates were nominally overdosed by 50 to 60%. No treatment was observed outside of the prostate capsule except in the localized area where the electrode was very close to the capsule. The estimated overdosing in this localized area was 160%. This indicates that, in a small sample size, the canine prostate capsule allows overdosing somewhere between 50% and 160% without allowing the treatment to affect adjacent tissues outside of the capsule. Anecdotal evidence indicates that the human capsule is more substantial than the canine capsule.

Example 5

A study was performed to assess various impedance parameters including dose to failure, effect of length, effect of electrode type, effect of electrode diameter, effect of pin diameter, effect of insulation, effect of current and parallel paths, The Dose to Failure evaluation showed that dose to failure is inversely proportional to length and diameter of the electrode and is proportional to the amount of venting. The following equation was determined:

$$DTF=(\text{Gas Formation}-\text{Venting})*\text{current}$$

$$DTF=(1/(d*L)-(n^2*\Delta p/I))*I$$

where:
DTF=Dose Time to Failure
d=diameter of electrode
L=length of electrode
n=number of electrodes
$\Delta p$=pressure drop across vent
I=length of insulation
I=current at electrode Through empirical testing it was shown that as pin length and diameter increases the impedance stability of the system increases. Furthermore as the electrode surface area of the active section increases the impedance stability increases. With a constant electrode surface area of the active sections impedance stability increases with a lower magnitude of direct current or running multiple electrodes in parallel. With a constant current and electrode surface area of the active section the impedance stability increases by decreasing the insulation length from the active area back to catheter by allowing the gases to vent out of the active area.

Example 6

A study was performed to assess the corrosive properties of nitinol and platinum-iridium-coated nitinol wires. The study further observed the effects of parylene-coated electrodes on electrode corrosion and tissue treatment zones.

Nitinol is commonly used in medicine and is known to corrode at the anode with applied direct current. Platinum is resistant to corrosion. Accordingly, for testing the invention disclosed herein, platinium iridium coated nitinol wires have been employed.

Parylene-C coating has high electroresistivity, is corrosion resistant, has high electrical impedance, and is impermeable to moisture. In this study, parylene-C coating was applied to both nitinol and platinum iridium electrodes.

Two tests were performed. One test used nitinol wires for both cathode and anode. The other test used platinium iridium-coated nitinol wires for both cathode and anode. The electrodes were inserted into two separate gels and run for 120 coulombs at 25 mA. To confirm no corrosion of the platinium ridium-coated nitinol electrodes, a further test was performed that was run for 500 coulombs at 25 mA. Pictures of each electrode were taken before and after the tests in order to see changes in the appearance of the electrodes. Observations and results were documented.

Figure 34A:
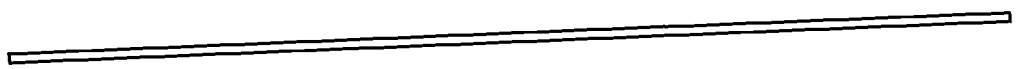
FIG. 34a illustrates a nitinol anode before starting a test.
Figure 34B:
FIG. 34b illustrates the nitinol anode of FIG. 36b after the test was stopped.

FIGS. 34$a$ and 34$b$ illustrate the nitinol anode before starting the test and after the test was stopped, respectively. The tests were to carry on for 120 coulombs at 25 mA. After approximately 20 minutes, the current for the nitinol electrodes dropped to 0 (zero). This was presumably due to corrosion of the anode, as illustrated in FIG. 34$b$.

The nitinol cathode had no apparent corrosion, nor did the platinum iridium-coated electrodes. The confirmation test of 500 coulombs at 25 mA also resulted in no observable corrosion of either the anode or the cathode.

The parylene-C coating also was found to be a dependable insulator. The portion of the electrodes that were coated with parylene-C were not active. No ion exchange occurred in these regions. This was observed at the start of the tests when the treatment sizes were not so big that they overlapped the coated regions. This coating also appeared to have a positive effect on impedance. It appeared that the microscopic insulation facilitated gas escape, resulting in a lower impedance.

The results showed that the nitinol anode had significant corrosion but the cathode did not. The platinum iridium-coated nitinol wires had no corrosion, even after further testing with 500 coulombs.

Example 7

A study was performed to determine the relationship between ease of electrode insertion and electrode diameter. Electrodes were inserted through the prostate capsule and into the urethra. Pig prostates were used.

Two pig prostates and urethras were inserted with various diameter pin electrodes. The resulting ease of piercing through the capsule and into the urethra was subjectively judged by the individuals inserting the pins into the urethras.

Pins were approximately 8 mm in length. Other methods of introducing the pin into the tissue were tried and judged relative to the initial insertion method. These methods include using a 0.5 mm diameter needle to pierce through the capsule and into the swine urethra and using a pair of tweezers to pierce and pull the tissues apart. The ease of insertion was then subjectively ranked by two individuals, each of whom did the trials independently, with a rank of 10 being the easiest to insert and a rank of 1 indicating nearly impossible to insert.

be inserted. Using a needle or tweezers to create a pilot hole was only incrementally better as it was difficult to find the hole.

Example 8

Initial human feasibility studies using DC ablation in the prostate with the Neuflo™ System (a transurethral DC Ablation system) have been conducted in Santiago, Chile. A summary of the studies conducted is given in Table 13.

TABLE 13

Table: Human Feasibility Studies Summary

| Study | Objectives | Subjects | Method | Findings |
|---|---|---|---|---|
| Stage 1: Ex Vivo post Radical Prostatectomy (RP) study of electrodes | 1. Validate tissue response in human prostate tissue. | 3 Prostates | Treat with DC ablation using pin electrodes inserted through the capsule immediately post RP | 1. Histological evidence of liquifactive and coagulative necrosis 2. Obtained a initial charge setting |
| Stage 2: In Vivo study of electrodes during RP | 1. Evaluate Treatment charge setting 2. Evaluate Impedance | 5 Subjects with Prostate Cancer | Treat with DC ablation using pin electrodes inserted through the capsule during RP | 1. Histological evidence of liquifactive and coagulative necrosis 2. Necrosis stayed within the capsule 3. Verified acceptable impedance |
| Stage 3: Transurethral Ex Vivo study of DC Ablation post RP | 1. Verify electrode placement and urethral puncture with Neuflo catheter 2. Determine optimal prostate size | 4 Prostates | Treat with TU Catheter immediately post RP | 1. Histological evidence of liquifactive and coagulative necrosis 2. Urethral puncture method was successful 3. Prostate size 30-65 $cm^3$ and sizing inc/exc criteria |
| Stage 4: Transurethral acute study of DC Ablation during RP | 1. Verify electrode placement and urethral puncture with Neuflo catheter 2. Determine optimal prostate size | 3 Prostate Cancer Subjects | Treat with TU Catheter during RP | 1. Histological evidence of liquifactive and coagulative necrosis 2. Urethral puncture method was successful 3. Prostate size 30-65 $cm^3$ and sizing inc/exc criteria |
| Feasibility Study of the TU DC Ablation System in BPH subjects | 1. Optimize treatment parameters 2. Obtain preliminary safety and efficacy data 3. Assess Discomfort | Up to 25 BPH subjects | Treat BPH with TU Catheter. Follow subjects for 1 year | 1. Obtained treatment parameters for US study 2. Obtained preliminary safety and efficacy data to utilized for hypothesis tests for the US study 3. Procedure was well tolerated |

Results are shown in Table 12, below.

TABLE 12

| Insertion Method | 0.5 mm Ptlr Pin | 0.8 mm Ptlr Pin | 0.3 mm Ptlr Coated NiTi |
|---|---|---|---|
| Normal | 6, 8 | 4, 6 | 1, 1 |
| Needle Pierced | 8, 7 | 6, 6 | 8, 1 |
| Tweezers | 8, 9 | 8, 9 | 2, 7 |

Test Subject: Subject 1 (First Number); Subject 2 (Second Number)

Both subjects ranked the diameter of electrodes in the following order: Best—0.5 mm Ptlr Pin, 0.8 mm Ptlr Pin, Worst—0.3 mm Ptlr Coated pin.

The 0.5 mm diameter pin provided substantial stiffness such that the electrode did not buckle. The 0.8 mm pin did not insert as easily as the 0.5 mm pin, presumably because the created hole is larger. It is hypothesized that if the tip of the 0.8 mm pin was sharpened or tapered, it could perform as well as the 0.5 mm pin. The 0.3 mm pin provided very little stiffness or mechanical advantage and buckled. This pin was unable to Stage 1 of the DC Ablation human studies involved treating three (3) human prostates with pin electrodes immediately post-radical prostatectomy (RP) for prostate cancer. Results showed the ability of DC ablation to induce consistent necrotic lesions within both malignant and benign prostate tissue.

Stage 2 of the human studies (in vivo) was conducted by treating patients prior to radical prostatectomy with pin electrodes to examine tissue response in living human prostate tissue. Immediately following DC ablation treatment, the prostates were removed as RP commenced following treatment completion.

Figure 35:
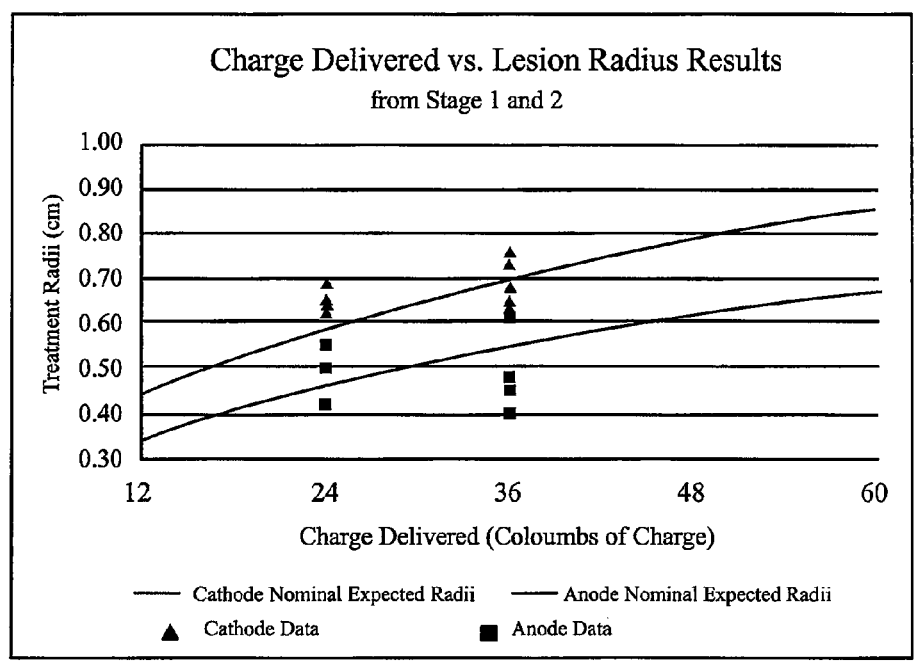
FIG. 35 illustrates results from the first two stages of human prostate tissue study.

Results from the first two stages of human prostate tissue study are shown in FIG. 35 with the upper trend line representing the cathode nominal expected radii and the lower trend line representing the anode nominal expected radii.

Human prostates were treated ex vivo (Stage 3) and in vivo during radical prostatectomy (Stage 4) with a Transurethral DC Ablation Catheter to more accurately represent future treatments; and to optimize electrode placement and monitor the safety of the placement of needles near the bladder and urethra.

Figure 36:
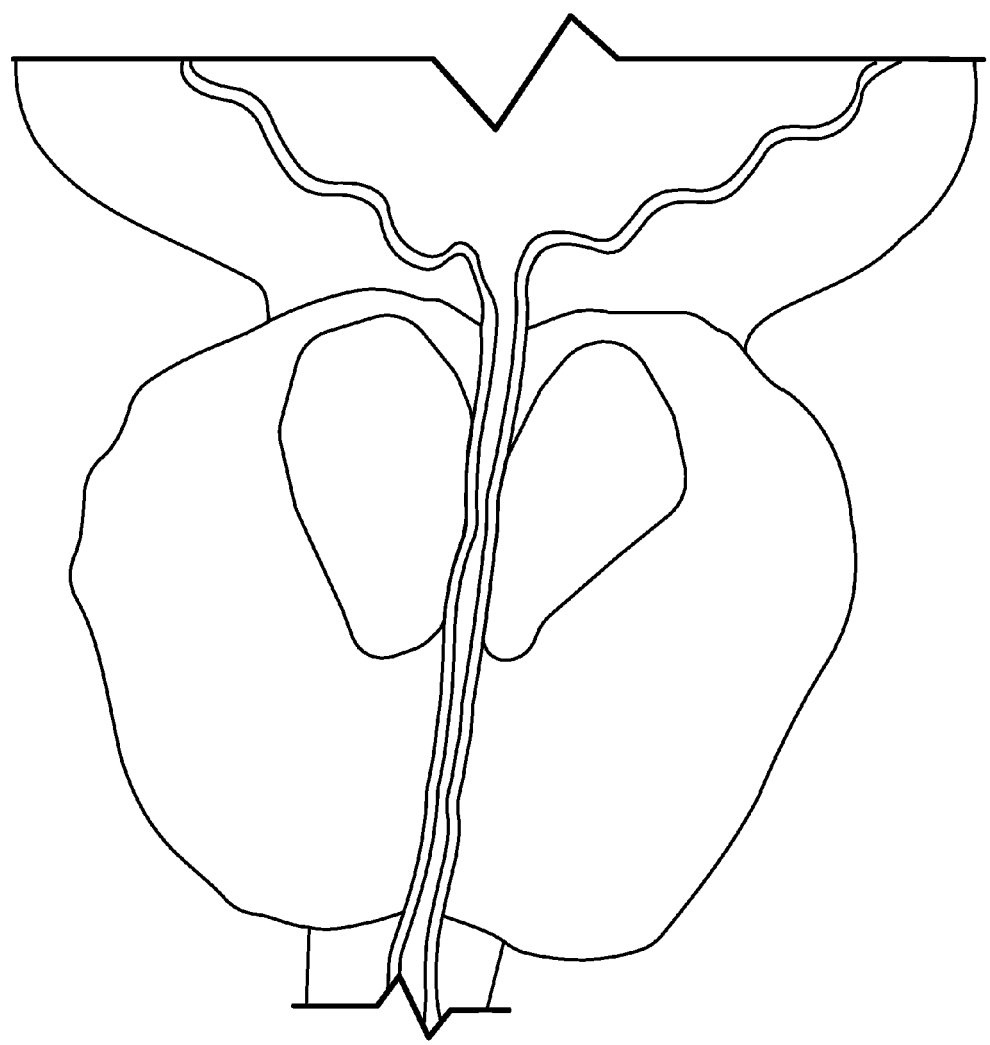
FIG. 36 is an in vivo image illustrating the necrosis volume achieved by the transurethrally ablating tissue with DC ablation.

FIG. 36 is an in vivo image illustrating the necrosis volume achieved by the transurethrally ablating tissue with DC ablation.

Sixteen BPH patients were treated with a transurethral DC ablation system to investigate the safety and efficacy of using a TU DC ablation system as a treatment for BPH. Prostate sizes ranged from 30 to 90 cm$^3$. The procedure was administered in an office setting using a topical lidocaine gel in the urethra. No oral sedative or local nerve block was required. Patients reported mild to no pain during the treatment.

Preliminary symptomatic relief data, as shown in Table 14, suggests that patients experienced symptomatic relief one week after treatment.

TABLE 14

BPH Feasibility Study Initial Efficacy Data
(Treatment Rate = 25 mA)

| Parameter | Baseline (n = 13) Mean ± SD | 1 week (n = 13) Mean ± SD (Paired % improvement) | 1 month (n = 10) Mean ± SD (Paired % improvement) | 3 month (n = 3) Mean ± SD (Paired % improvement) |
|---|---|---|---|---|
| AUA Symptom Score | 24.1 ± 4.8 | 14.3 ± 5.6 (38%) | 14.3 ± 5.6 (37%) | 7.7 ± 5.0 (65%) |
| QOL | 5.0 ± 0.8 | 2.8 ± 1.5 (44%) | 2.3 ± 1.7 (54%) | 0.7 ± 0.6 (86%) |
| Qmax | 9.6 ± 3.5 | 12.1 ± 2.5 (26%) | 13.7 ± 4.3 (43%) | 9.7 ± 5.0 (1%) |

In addition, 3 subjects were treated within the OUS study in which the treatment rate was 40 mA. Based on the subject's transient (1 week) increase in symptoms, quality of life and their diminished ability to urinate, a decision was made to utilize a treatment rate of 25 mA. Initial safety data revealed no severe adverse events in the first 16 patients treated at 25 mA and 40 mA. Urological adverse events are listed in the Table 15.

TABLE 15

Table: Urological Adverse Event Frequency
(Treatment Rate = 25 mA and 40 mA)

| Adverse Event | Timepoints* | | |
|---|---|---|---|
| | 1 week (n = 12) (mild/mod/severe) | 1 month (n = 12) (mild/mod/severe) | 3 month (n = 6) (mild/mod/severe) |
| Hematuria | 17%/0%/0% | 0%/0%/0% | 0%/0%/0% |
| Dysuria | 55%/23%/8% | 40%/20%/8% | 17%/0%/0% |
| Pelvic Pain | 31%/0%/0% | 20%/0%/0% | 0%/0%/0% |
| Bladder Spasms | 23%/23%/0% | 0%/0%/0% | 0%/0%/0% |
| Urgency Incontinence | 8%/15%/0% | 8%/0%/8% | 17%/0%/0% |
| Incontinence | 0%/0%/0% | 0%/0%/0% | 0%/0%/0% |
| Urinary Infection | 0%/0%/0% | 0%/0%/0% | 0%/0%/0% |
| Acute Retention | 0% | 0% | 0% |

*includes monitored data only

The invention claimed is:

1. A minimally invasive method for treating prostate tissue of a prostate in a body via direct current ablation from a urethra transecting the prostate, comprising:

inserting a catheter into the urethra, wherein a portion of the catheter remains outside of the body when the catheter is in a treatment position proximate the prostate;

deploying a fixation element associated with the catheter to fix the catheter in the treatment position;

deploying a plurality of electrodes through the catheter into the prostate, wherein at least one of the plurality of electrodes is deployed into at least one of a lateral posterior quadrant of the prostate tissue relative to the urethra, a lateral anterior quadrant of the prostate tissue relative to the urethra, or combinations of the prostate tissue relative to the urethra thereof, and wherein the electrodes are separated by an angular spacing;

determining input treatment parameters, wherein the input treatment parameters include a quantity of charge to the prostate tissue;

inputting the input treatment parameters into at least one of a power source and a processor;

using a power source to apply direct current between approximately 10 and 50 mA and a power of less than 3200 mW to each of the plurality of electrodes to deliver the quantity of charge, wherein the direct current applied is based on the input treatment parameters;

wherein upon application of the direct current, at least one of the plurality of electrodes imparts at least one of a high pH and a low pH in a treatment zone proximate to each electrode of the plurality of electrodes to create a necrotic zone in the treatment zone, wherein the application of the direct current is substantially non-thermal;

comparing a measured treatment parameter with at least one of the input treatment parameters; and stopping the application of direct current to the treatment zone once the measured treatment parameter reaches the at least one input treatment parameter, wherein the at least one input treatment parameter is reached and the application of direct current to the plurality of electrodes is stopped between approximately 15 and 45 minutes with the catheter in the treatment position.

2. The minimally invasive method of claim 1, wherein the plurality of electrodes are the fixation element and deploying the fixation element and deploying the plurality of electrodes comprises one step of deploying the plurality of electrodes.

3. The minimally invasive method of claim 1, wherein the treatment zone is created between a bladder neck and a verumontanum of the prostate and wherein the minimally invasive method treats benign prostatic hyperplasia.

4. The minimally invasive method of claim 1, further comprising determining a prostate size to determine the input treatment parameters.

5. The minimally invasive method of claim 4, wherein an ultrasound, a cystoscopy, an MRI, a PET, or a CT is used to determine the prostate size.

6. The minimally invasive method of claim 4, further comprising determining a transverse width of the prostate to determine the input treatment parameters.

7. The minimally invasive method of claim 4, wherein the input treatment parameters include at least one of electrode insertion length, charge delivered, direct current magnitude, and treatment duration, and wherein determining the input treatment parameters comprises comparing information gathered from determining the prostate size against tabulated data.

8. The minimally invasive method of claim 1, wherein the input treatment parameters include at least one of electrode insertion length, charge delivered, direct current magnitude, and treatment duration.

9. The minimally invasive method of claim 1, wherein the fixation element is deployed in a urinary bladder and further comprising using ultrasound to verify positioning of the fixation element in the urinary bladder.

10. The minimally invasive method of claim 1, further comprising examining the body by cystoscopy or ultrasound to determine a number of electrodes of the plurality of electrodes to be deployed.

11. The minimally invasive method of claim 1, wherein the plurality of electrodes are deployed a distance of 14 to 22 mm into the prostate.

12. The minimally invasive method of claim 1, wherein the plurality of electrodes comprises between 2 and 12 electrodes.

13. The minimally invasive method of claim 1, wherein the plurality of electrodes comprises between 4 and 8 electrodes.

14. The minimally invasive method of claim 1, further comprising visualizing at least one of the catheter, the plurality of electrodes, and the fixation element during deployment or treatment and wherein visualizing is done by at least one of magnetic resonance, fluoroscopy, and ultrasound imaging.

15. The minimally invasive method of claim 1, further comprising increasing or decreasing the direct current delivered by the plurality of electrodes at a controlled ramp rate.

16. The minimally invasive method of claim 15, wherein the controlled ramp rate is between approximately 0.1 mA/sec and 10 mA/sec.

17. The minimally invasive method of claim 1, wherein the direct current is kept constant throughout the application of direct current by using voltage compliance to adjust for changing impedance between the plurality of electrodes during treatment.

18. The minimally invasive method of claim 1, wherein deploying the fixation element comprises inflating a balloon.

19. The minimally invasive method of claim 18, wherein inflating the balloon comprises inflating the balloon in a bladder.

20. The minimally invasive method of claim 1, wherein the necrotic zone is created with a temperature increase in the prostate of less than 8 degrees.

21. The minimally invasive method of claim 1, wherein the necrotic zone is created with a temperature increase in the prostate of less than that required to cause thermal damage to the prostate tissue.

22. The minimally invasive method of claim 1, further comprising using an indifferent electrode outside the body to complete a treatment circuit with the plurality of electrodes.

23. The minimally invasive method of claim 1, wherein the quantity of charge is between approximately 15 and 72 coulombs to each electrode of the plurality of electrodes.

24. The minimally invasive method of claim 1, wherein the quantity of charge is between approximately 24 and 48 coulombs to each electrode of the plurality of electrodes.

25. The minimally invasive method of claim 1, further comprising testing impedance of the plurality of electrodes in the prostate tissue to verify adequate contact.

26. A minimally invasive method for treating at least one treatment zone of prostate tissue of a prostate in a body via direct current ablation from a urethra transecting the prostate, comprising:
    inserting a catheter into the urethra, wherein a portion of the catheter remains outside of the body when the catheter is in a treatment position proximate the prostate;
    deploying a fixation element in a urinary bladder, the fixation element being operably coupled to the catheter and operating to fix the catheter in the treatment position;
    deploying between approximately 4 and 8 electrodes a distance of approximately 14 to 22 mm into both lateral lobes of the prostate, wherein at least one of the between approximately 4 and 8 electrodes is deployed into at least one of a lateral posterior quadrant of the prostate tissue relative to the urethra, a lateral anterior quadrant of the prostate tissue relative to the urethra, or combinations of the prostate tissue relative to the urethra thereof, and wherein electrode pairs each consist of a subset of the between approximately 4 and 8 electrodes are separated from one another by an angular spacing;
    determining input treatment parameters including a quantity of charge to be delivered to the at least one treatment zone;
    inputting the input treatment parameters into at least one of a power source and a processor;
    using a power source to apply a direct current between approximately 10 and 50 mA, a power of less than 3200 mW and the quantity of charge of between approximately 15 and 72 coulombs to each of the electrode pairs of the between 4 and 7 electrodes, wherein the direct current applied is based on the input treatment parameters;
    wherein upon application of the direct current, at least one electrode of the between approximately 4 and 8 electrodes imparts at least one of a high pH and a low pH in a treatment zone proximate to the at least one electrode of the between approximately 4 and 8 electrodes to create a necrotic zone in the treatment zone, wherein the application of the direct current is substantially non-thermal;
    comparing a measured treatment parameter with at least one of the input treatment parameters; and
    stopping the application of the direct current to the treatment zone once the measured treatment parameter reaches the at least one input treatment parameter, wherein the at least one input treatment parameter is reached and the application of the direct current to the between approximately 4 and 8 of electrodes is done in approximately 15 to approximately 45 minutes with the catheter in the treatment position.

27. The minimally invasive method of claim 26, wherein Benign Prostatic Hyperplasia is treated between a bladder neck and a verumontanum of the prostate.

28. The minimally invasive method of claim 26, wherein determining the input treatment parameters includes determining prostate size.

29. The minimally invasive method of claim 26, wherein the method imparts a temperature increase in the prostate of less than 8 degrees.

* * * * *